US012774497B2

(12) United States Patent
West

(10) Patent No.: US 12,774,497 B2
(45) **Date of Patent: *Oct. 27, 2026**

(54) METHODS FOR USING MOSAICISM IN NUCLEIC ACIDS SAMPLED DISTAL TO THEIR ORIGIN

(71) Applicant: Personalis, Inc., Fremont, CA (US)

(72) Inventor: John West, Cupertino, CA (US)

(73) Assignee: Personalis, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/404,644

(22) Filed: Dec. 1, 2025

(65) Prior Publication Data

US 2026/0085363 A1 Mar. 26, 2026

Related U.S. Application Data

(60) Continuation of application No. 19/073,665, filed on Mar. 7, 2025, now Pat. No. 12,516,385, which is a continuation of application No. 18/613,618, filed on Mar. 22, 2024, now Pat. No. 12,270,083, which is a continuation of application No. 17/828,572, filed on May 31, 2022, now Pat. No. 11,965,214, which is a continuation of application No. 17/748,200, filed on May 19, 2022, now Pat. No. 11,649,507, which is a continuation of application No. 17/494,513, filed on Oct. 5, 2021, now Pat. No. 11,584,968, which is a division of application No. 16/132,123, filed on Sep. 14, 2018, now Pat. No. 11,142,802, which is a continuation of application No. 14/929,075, filed on Oct. 30, 2015, now Pat. No. 10,125,399.

(60) Provisional application No. 62/072,936, filed on Oct. 30, 2014.

(51) Int. Cl.

| | |
|---|---|
| ***C12Q 1/6886*** | (2018.01) |
| ***A61K 31/7068*** | (2006.01) |
| ***C12Q 1/6809*** | (2018.01) |
| ***C12Q 1/6827*** | (2018.01) |
| ***G16B 45/00*** | (2019.01) |

(52) U.S. Cl.

CPC ........ *C12Q 1/6886* (2013.01); *A61K 31/7068* (2013.01); *G16B 45/00* (2019.02); *C12Q 1/6809* (2013.01); *C12Q 1/6827* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 4,458,066 | A | 7/1984 | Caruthers et al. |
| 4,683,202 | A | 7/1987 | Mullis |
| 4,988,617 | A | 1/1991 | Landegren et al. |
| 5,143,854 | A | 9/1992 | Pirrung et al. |
| 5,242,794 | A | 9/1993 | Whiteley et al. |
| 5,299,491 | A | 4/1994 | Kawada |
| 5,382,510 | A | 1/1995 | Levine et al. |
| 5,403,708 | A | 4/1995 | Brennan et al. |
| 5,412,087 | A | 5/1995 | Mcgall et al. |
| 5,432,065 | A | 7/1995 | Fuller |
| 5,472,672 | A | 12/1995 | Brennan |
| 5,494,810 | A | 2/1996 | Barany et al. |
| 5,641,658 | A | 6/1997 | Adams et al. |
| 5,928,907 | A | 7/1999 | Woudenberg et al. |
| 6,015,674 | A | 1/2000 | Woudenberg et al. |
| 6,045,996 | A | 4/2000 | Cronin et al. |
| 6,156,504 | A | 12/2000 | Gocke et al. |
| 6,420,117 | B1 | 7/2002 | Wessler et al. |
| 6,582,938 | B1 | 6/2003 | Su et al. |
| 6,754,655 | B1 | 6/2004 | Segal |
| 6,818,395 | B1 | 11/2004 | Quake et al. |
| 7,169,560 | B2 | 1/2007 | Lapidus et al. |
| 7,211,390 | B2 | 5/2007 | Rothberg et al. |
| 7,211,654 | B2 | 5/2007 | Gao et al. |
| 7,244,559 | B2 | 7/2007 | Rothberg et al. |
| 7,264,929 | B2 | 9/2007 | Rothberg et al. |
| 7,280,922 | B2 | 10/2007 | Mei et al. |
| 7,282,337 | B1 | 10/2007 | Harris |
| 7,300,788 | B2 | 11/2007 | Matsuzaki et al. |
| 7,323,305 | B2 | 1/2008 | Leamon et al. |
| 7,335,762 | B2 | 2/2008 | Rothberg et al. |
| 7,361,488 | B2 | 4/2008 | Fan et al. |
| 7,534,561 | B2 | 5/2009 | Sana et al. |
| 7,582,420 | B2 | 9/2009 | Oliphant et al. |

(Continued)

FOREIGN PATENT DOCUMENTS

| | | | |
|---|---|---|---|
| CN | 105044108 | A | 11/2015 |
| CN | 109903811 | A | 6/2019 |

(Continued)

OTHER PUBLICATIONS

Dawson et al. "Analysis of circulating tumor DNA to monitor metastatic breast cancer." New England Journal of Medicine 368.13 (2013): 1199-1209.

(Continued)

*Primary Examiner* — Joseph Woitach

(74) *Attorney, Agent, or Firm* — Orrick, Herrington & Sutcliffe, LLP

(57) ABSTRACT

Disclosed herein are methods for improving detection and monitoring of human diseases. The methods can be used to provide spatial and/or developmental localization of the source of each differential mutation within the body. The methods can also be used to generate a mutation map of a subject. And the mutation map can be used to monitoring state(s) of health of one or more tissues of a subject.

30 Claims, 6 Drawing Sheets

(56) References Cited

U.S. PATENT DOCUMENTS 7,785,783 B2 8/2010 Morley et al.
7,803,550 B2 9/2010 Makarov et al.
8,026,094 B2 9/2011 Green et al.
8,133,719 B2 3/2012 Drmanac et al.
8,140,270 B2 3/2012 Kingsmore et al.
8,296,076 B2 10/2012 Fan et al.
8,318,430 B2 11/2012 Chuu et al.
8,323,897 B2 12/2012 Andersen et al.
8,415,101 B2 4/2013 Garner
8,417,459 B2 4/2013 Reese et al.
8,532,930 B2 9/2013 Rabinowitz et al.
8,589,175 B2 11/2013 Glauser et al.
8,785,353 B2 7/2014 Van Eijk et al.
8,862,410 B2 10/2014 Hatchwell et al.
9,051,602 B2 6/2015 Oliphant et al.
9,109,256 B2 8/2015 Shuber
9,128,861 B2 9/2015 Bartha et al.
9,183,496 B2 11/2015 Harris et al.
9,228,232 B2 1/2016 Faham et al.
9,329,170 B2 5/2016 Clarke et al.
9,416,422 B2 8/2016 Cheung
9,453,257 B2 9/2016 Hoyal-Wrightson et al.
9,512,485 B2 12/2016 Richardson et al.
9,523,121 B2 12/2016 Spier et al.
9,725,755 B2 8/2017 Poole et al.
9,727,692 B2 8/2017 Harris et al.
9,745,626 B2 8/2017 Bartha et al.
9,909,186 B2 3/2018 Schuetz et al.
10,017,810 B2 7/2018 Iafrate et al.
10,032,000 B1 7/2018 Harris et al.
10,125,399 B2 11/2018 West
10,174,375 B2 1/2019 Lo et al.
10,255,330 B2 4/2019 Chandratillake et al.
10,262,103 B2 4/2019 Lehrer et al.
10,266,890 B2 4/2019 Bartha et al.
10,344,318 B2 7/2019 May et al.
10,415,091 B2 9/2019 Bartha et al.
10,450,611 B2 10/2019 West et al.
10,590,468 B2 3/2020 Pedersen et al.
10,597,717 B2 3/2020 Maguire et al.
10,711,306 B2 7/2020 Shiina et al.
10,738,355 B2 8/2020 Sahin et al.
10,741,269 B2 8/2020 Chudova et al.
10,801,064 B2 10/2020 West et al.
10,801,070 B2 10/2020 Clement et al.
10,900,088 B2 1/2021 Volgelstein et al.
11,047,006 B2 6/2021 Salk et al.
11,062,789 B2 7/2021 Chiu et al.
11,124,824 B2 9/2021 Sarwal et al.
11,142,797 B2 10/2021 Moynahan et al.
11,155,867 B2 10/2021 Bartha et al.
11,286,530 B2 3/2022 Rabinowitz et al.
11,345,968 B2 5/2022 Mortimer et al.
11,840,730 B1 12/2023 Porreca et al.
12,203,142 B2 1/2025 Babiarz et al.
2002/0006615 A1 1/2002 Goldsborough et al.
2002/0164629 A1 11/2002 Quake et al.
2003/0022200 A1 1/2003 Vissing et al.
2003/0096011 A1 5/2003 Tracy et al.
2003/0099964 A1 5/2003 Patil et al.
2003/0100995 A1 5/2003 Loraine et al.
2003/0220777 A1 11/2003 Kitchen et al.
2005/0042668 A1 2/2005 Perlin
2005/0086035 A1 4/2005 Peccoud et al.
2005/0125474 A1 6/2005 Pednault
2005/0250125 A1 11/2005 Novakoff
2005/0260645 A1 11/2005 Green et al.
2006/0184489 A1 8/2006 Weiner et al.
2006/0278241 A1 12/2006 Ruano
2007/0111247 A1 5/2007 Stephens et al.
2007/0184436 A1 8/2007 Myerson et al.
2008/0096766 A1 4/2008 Lee
2008/0305473 A1 12/2008 Chowdary et al.
2009/0026082 A1 1/2009 Rothberg et al.
2009/0029364 A1 1/2009 Zirwes et al.
2009/0127589 A1 5/2009 Rothberg et al.
2009/0183268 A1 7/2009 Kingsmore
2009/0191565 A1 7/2009 Lapidus et al.
2009/0326832 A1 12/2009 Heckerman et al.
2010/0029498 A1 2/2010 Gnirke et al.
2010/0035252 A1 2/2010 Rothberg et al.
2010/0042438 A1 2/2010 Moore et al.
2010/0137143 A1 6/2010 Rothberg et al.
2010/0188073 A1 7/2010 Rothberg et al.
2010/0197507 A1 8/2010 Rothberg et al.
2010/0282617 A1 11/2010 Rothberg et al.
2010/0300559 A1 12/2010 Schultz et al.
2010/0300895 A1 12/2010 Nobile et al.
2010/0301398 A1 12/2010 Rothberg et al.
2010/0304982 A1 12/2010 Hinz et al.
2011/0004413 A1 1/2011 Carnevali et al.
2011/0009296 A1 1/2011 Kain et al.
2011/0105353 A1 5/2011 Lo et al.
2011/0184896 A1 7/2011 Guyon
2012/0015050 A1 1/2012 Abkevich et al.
2012/0058480 A1 3/2012 Lewis et al.
2012/0077682 A1 3/2012 Bowcock et al.
2012/0116688 A1 5/2012 Mishra et al.
2012/0143512 A1 6/2012 Reese et al.
2012/0208706 A1 8/2012 Downing et al.
2012/0270206 A1 10/2012 Ginns et al.
2012/0270212 A1 10/2012 Rabinowitz et al.
2012/0295810 A1 11/2012 Quake et al.
2013/0073217 A1 3/2013 Dewey et al.
2013/0090908 A1 4/2013 Dewey et al.
2013/0096011 A1 4/2013 Rava et al.
2013/0102477 A1 4/2013 Morin et al.
2013/0124100 A1 5/2013 Drmanac et al.
2013/0173177 A1 7/2013 Pelleymounter
2013/0178389 A1 7/2013 Lapidus et al.
2013/0261196 A1 10/2013 Diamond et al.
2013/0296535 A1 11/2013 Church et al.
2013/0311448 A1 11/2013 Thompson
2013/0332081 A1 12/2013 Reese et al.
2014/0186827 A1 7/2014 Pieprzyk et al.
2014/0200147 A1 7/2014 Bartha et al.
2015/0051087 A1 2/2015 Rabinowitz et al.
2015/0057160 A1 2/2015 Breuer et al.
2015/0066824 A1 3/2015 Harris et al.
2016/0019341 A1 1/2016 Harris et al.
2016/0032396 A1 2/2016 Diehn et al.
2016/0041987 A1 2/2016 Lapir et al.
2016/0092631 A1 3/2016 Yandell et al.
2016/0122831 A1 5/2016 West
2016/0283484 A1 9/2016 Chandratillake et al.
2017/0166981 A1 6/2017 Craig et al.
2017/0199961 A1 7/2017 Yelensky et al.
2017/0253921 A1 9/2017 Liu et al.
2017/0316150 A1 11/2017 Deciu et al.
2017/0356053 A1 12/2017 Otto et al.
2018/0051338 A1 2/2018 West et al.
2018/0127807 A1 5/2018 Stahl et al.
2018/0203974 A1 7/2018 Venn
2018/0258489 A1 9/2018 Danenberg
2018/0282801 A1 10/2018 Zhao et al.
2018/0363066 A1 12/2018 Chalmers et al.
2019/0127803 A1 5/2019 Hacohen et al.
2019/0153541 A1 5/2019 Lo et al.
2019/0189242 A1 6/2019 Angiuoli et al.
2019/0211406 A1 7/2019 Babiarz et al.
2019/0285518 A1 9/2019 Lu et al.
2019/0346442 A1 11/2019 Carr et al.
2020/0024669 A1 1/2020 Spetzler et al.
2020/0048711 A1 2/2020 Snyder
2020/0058377 A1 2/2020 Bagaev et al.
2020/0105378 A1 4/2020 Abelin et al.
2020/0149097 A1 5/2020 Otto et al.
2020/0157604 A1 5/2020 Plagnol et al.
2020/0202224 A1 6/2020 Lanman et al.
2020/0258597 A1 8/2020 Perera
2020/0258601 A1 8/2020 Lau
2020/0392584 A1 12/2020 Almogy et al.
2021/0054452 A1 2/2021 West et al.
2021/0062258 A1 3/2021 Bartha et al.

(56) References Cited

U.S. PATENT DOCUMENTS

| | | | |
|---|---|---|---|
| 2021/0062276 A1 | 3/2021 | West |
| 2021/0210205 A1 | 7/2021 | Drake et al. |
| 2021/0238677 A1 | 8/2021 | Bartha et al. |
| 2021/0363586 A1 | 11/2021 | Artsiomenka et al. |
| 2021/0398609 A1 | 12/2021 | Sigurjonsson et al. |
| 2022/0064733 A1 | 3/2022 | Alexander et al. |
| 2022/0073985 A1 | 3/2022 | Nerenberg et al. |
| 2022/0081716 A1 | 3/2022 | West et al. |
| 2022/0195530 A1 | 6/2022 | Diehn et al. |

FOREIGN PATENT DOCUMENTS

| | | |
|---|---|---|
| EP | 0 281 927 B1 | 6/1995 |
| EP | 1 342 794 B1 | 12/2005 |
| EP | 2 861 788 B1 | 10/2018 |
| EP | 3 212 808 B1 | 3/2022 |
| WO | 2000/18957 A1 | 4/2000 |
| WO | 2005/098046 A2 | 10/2005 |
| WO | 2007/055244 A1 | 5/2007 |
| WO | 2010/054589 A1 | 5/2010 |
| WO | 2011/050341 A1 | 4/2011 |
| WO | 2011/057061 A1 | 5/2011 |
| WO | 2011/057094 A1 | 5/2011 |
| WO | 2011/091046 A1 | 7/2011 |
| WO | 2011/149534 A2 | 12/2011 |
| WO | 2011/160063 A2 | 12/2011 |
| WO | 2011/160206 A1 | 12/2011 |
| WO | 2012/142611 A2 | 10/2012 |
| WO | 2014/053295 A1 | 4/2014 |
| WO | 2014/062717 A1 | 4/2014 |
| WO | 2014/113204 A1 | 7/2014 |
| WO | 2014/207245 A1 | 12/2014 |
| WO | 2015/051275 A1 | 4/2015 |
| WO | 2015/095889 A2 | 6/2015 |
| WO | 2016/070131 A1 | 5/2016 |
| WO | 2017/205823 A1 | 11/2017 |
| WO | 2018/053365 A1 | 3/2018 |
| WO | 2018/064547 A1 | 4/2018 |
| WO | 2018/144782 A1 | 8/2018 |
| WO | 2018/195357 A1 | 10/2018 |
| WO | 2018/222883 A1 | 12/2018 |
| WO | 2019/168984 A1 | 9/2019 |
| WO | 2019/226939 A1 | 11/2019 |
| WO | 2019/231856 A1 | 12/2019 |
| WO | 2020/132586 A1 | 6/2020 |
| WO | 2020/168008 A1 | 8/2020 |
| WO | 2020/252721 A1 | 12/2020 |
| WO | 2021/016089 A1 | 1/2021 |
| WO | 2022/046947 A1 | 3/2022 |

OTHER PUBLICATIONS

De La Chapelle, A. "The incidence of Lynch syndrome." Familial cancer 4 (2005): 233-237.

De Mattos-Arruda et al. "Capturing intra-tumor genetic heterogeneity by de novo mutation profiling of circulating cell-free tumor DNA: a proof-of-principle." Annals of oncology 25.9 (2014): 1729-1735.

De Mattos-Arruda et al. "Circulating tumour cells and cell-free DNA as tools for managing breast cancer." Nature reviews Clinical oncology 10.7 (2013): 377-389.

Decathelineau et al. "The final step in programmed cell death: phagocytes carry apoptotic cells to the grave." Essays in biochemistry 39 (2003): 105-117.

Dewey et al. "Phased whole-genome genetic risk in a family quartet using a major allele reference sequence." PLoS genetics 7.9 (2011): 1-15.

Diaz et al. "Insights into therapeutic resistance from whole-genome analyses of circulating tumor DNA." Oncotarget 4.10 (2013): 1856-1857.

Diaz et al. "Liquid biopsies: genotyping circulating tumor DNA." Journal of clinical oncology 32.6 (2014): 579-586.

Diehl et al. "Detection and quantification of mutations in the plasma of patients with colorectal tumors." Proceedings of the National Academy of Sciences 102.45 (2005): 16368-16373.

Ding et al. "Genome remodelling in a basal-like breast cancer metastasis and xenograft." Nature 464.7291 (2010): 999-1005.

Dressman et al. "Transforming single DNA molecules into fluorescent magnetic particles for detection and enumeration of genetic variations." Proceedings of the National Academy of Sciences 100.15 (2003): 8817-8822.

Drmanac et al. "Human genome sequencing using unchained base reads on self-assembling DNA nanoarrays." Science 327.5961 (2010): 78-81.

Ecseq, "How to calculate the coverage for a NGS experiment." ecSeq Bioinformatics, 2019 [retrieved on Jul. 5, 2022]. Retrieved from the Internet: <URL:https://www.ecseq.com/support/ngs/how-to-calculate-the-coverage-for-a-sequencing-experiment>, 3 pages.

Ellinger et al. "The role of cell-free circulating DNA in the diagnosis and prognosis of prostate cancer." Urologic Oncology: Seminars and Original Investigations. vol. 29. No. 2. Elsevier, 2011: 124-129.

Elsharawy et al. "Accurate variant detection across non-amplified and whole genome amplified DNA using targeted next generation sequencing." BMC genomics 13 (2012): 1-14.

Elshimali et al. "The clinical utilization of circulating cell free DNA (CCFDNA) in blood of cancer patients." International journal of molecular sciences 14.9 (2013): 18925-18958.

Esplin et al. "Personalized sequencing and the future of medicine: discovery, diagnosis and defeat of disease." Pharmacogenomics 15.14 (2014): 1771-1790.

Extended European Search Report in EP22153028.0, mailed Jun. 9, 2022, 9 pages.

Human Genome Overview, "GRCh37," Genome Reference Consortium, Feb. 27, 2009. Retrieved from the Internet: <URL:https://www.ncbi.nlm.nih.gov/grc/human>, 2 pages.

Fahy et al. "Self-sustained sequence replication (3SR): an isothermal transcription-based amplification system alternative to PCR." Genome Research 1.1 (1991): 25-33.

Fairbrother et al. "Rescue-ESE identifies candidate exonic splicing enhancers in vertebrate exons." Nucleic acids research 32 (2004): W187-W190.

Fishel et al. "Meta-analysis of gene expression data: a predictor-based approach." Bioinformatics 23.13 (2007): 1599-1606.

Forshew et al. "Noninvasive identification and monitoring of cancer mutations by targeted deep sequencing of plasma DNA." Science translational medicine 4.136 (2012): 1-13.

Forshew et al. "Noninvasive identification and monitoring of cancer mutations by targeted deep sequencing of plasma DNA." Supplementary Materials. Science translational medicine 4.136 (2012): 1-20.

Fox et al. "Accuracy of next generation sequencing platforms." Next generation, sequencing & applications 1 (2014): 1-9.

Freed et al. "Somatic mosaicism in the human genome." Genes 5.4 (2014): 1064-1094.

Freshney, R. "Culture of Animal Cells: A Manual of Basic Technique and Specialized Applications Sixth Edition." Hoboken, New Jersey, John Wiley & Sons (2010): 1-42.

Frumkin et al. "Genomic variability within an organism exposes its cell lineage tree." PLoS computational biology 1.5 (2005): 382-394.

GATK. "Genome Analysis Toolkit: Variant Discovery in High-Throughput Sequencing Data." Broad Institute, 2019 [retrieved on Apr. 29, 2019]. Retrieved from the Internet: <URL: https://software.broadinstitute.org/gatk>, 2 pages.

Gilbert, S. "Developmental Biology Tenth Edition." Sunderland, MA, Sinauer Associates, Inc. (2014): 1-12.

Gnirke et al. "Solution hybrid selection with ultra-long oligonucleotides for massively parallel targeted sequencing." Nature biotechnology 27.2 (2009): 182-189.

Golob, J. "Mechanisms of cell fate acquisition in the differentiation of pluripotent stem cells." University of Washington (2009): 1-126.

Goris et al. "The immunogenetic architecture of autoimmune disease." Cold Spring Harbor perspectives in biology 4.3 (2012): 1-15.

(56) References Cited

OTHER PUBLICATIONS

Gottlieb et al. "The DiGeorge syndrome minimal critical region contains a goosecoid-like (GSCL) homeobox gene that is expressed early in human development." American journal of human genetics 60.5 (1997): 1194-1201.
Griewank et al. "Genetic alterations and personalized medicine in melanoma: progress and future prospects." Journal of the National Cancer Institute 106.2 (2014): 1-17.
Guan et al. "Application of next-generation sequencing in clinical oncology to advance personalized treatment of cancer." Chinese journal of cancer 31.10 (2012): 463-470.
Guo et al. "Exome sequencing generates high quality data in non-target regions." BMC genomics 13 (2012): 1-10.
Guo et al. "Exome sequencing generates high quality data in non-target regions." BMC genomics 13, Supplementary Tables, (2012): 1-803.
Guo et al. "Whole-genome and whole-exome sequencing of bladder cancer identifies frequent alterations in genes involved in sister chromatid cohesion and segregation." Nature genetics 45.12 (2013): 1459-1463.
Haferlach et al. "Mutations of the TP53 gene in acute myeloid leukemia are strongly associated with a complex aberrant karyotype." Leukemia 22.8 (2008): 1539-1541.
Hamfjord et al. "Differential expression of miRNAs in colorectal cancer: comparison of paired tumor tissue and adjacent normal mucosa using high-throughput sequencing." PloS one 7.4 (2012): 1-9.
Hiratani et al. "Replication timing and transcriptional control: beyond cause and effect—part II." Current opinion in genetics & development 19.2 (2009): 142-149.
Hirschhorn et al. "Human intersex with chromosome mosaicism of type XY/XO: Report of a case." New England Journal of Medicine 263.21 (1960): 1044-1048.
Hohaus et al. "Cell-free circulating DNA in Hodgkin's and non-Hodgkin's lymphomas." Annals of oncology 20.8 (2009): 1408-1413.
Holstege et al. "Somatic mutations found in the healthy blood compartment of a 115-yr-old woman demonstrate oligoclonal hematopoiesis." Genome research 24.5 (2014): 733-742.
Hong et al. "Tracking the origins and drivers of subclonal metastatic expansion in prostate cancer." Nature communications 6.1 (2015): 1-12.
Huang et al. "Characterization of human plasma-derived exosomal RNAs by deep sequencing." BMC genomics 14 (2013): 1-14.
Huang et al. "Machine learning predicts individual cancer patient responses to therapeutic drugs with high accuracy." Scientific reports 8.1 (2018): 1-8.
Huang et al. "Smurf: portable and accurate ensemble prediction of somatic mutations." Bioinformatics 35.17 (2019): 3157-3159.
Sulston et al. "The embryonic cell lineage of the nematode Caenorhabditis elegans." Developmental biology 100.1 (1983): 64-119.
Summerer et al. "Targeted high throughput sequencing of a cancer-related exome subset by specific sequence capture with a fully automated microarray platform." Genomics 95.4 (2010): 241-246.
Sun et al. "Optimized data representation and convolutional neural network model for predicting tumor purity." bioRxiv (2019): 1-9.
Sung et al. "Assessment of intratumoral heterogeneity with mutations and gene expression profiles." PLoS One 14.7 (2019): 1-15.
Supplementary European Search Report in EP15853674, mailed May 25, 2018, 2 pages.
SV Bio Current Services, SV Bio, 2014 [retrieved on Sep. 12, 2022]. Retrieved from the Internet: <URL:http:www.svbio.com/service-offerings/current-services>, 1 page.
Swanton, C. "Plasma-derived tumor DNA analysis at whole-genome resolution." Clinical Chemistry 59.1 (2013): 6-8.
Technical Note: DNA Analysis, "Interpreting Infinium Assay Data for Whole-Genome Structural Variation," Illumina, 2010, 8 pages.
Teer et al. "Exome sequencing: the sweet spot before whole genomes." Human molecular genetics 19.R2 (2010): R145-R151.
Tests and Procedures, "Urine cytology," Mayo Clinic, Nov. 15, 2014 [retrieved on Dec. 1, 2015]. Retrieved from the Internet: <URL:http://www.mayoclinic.org/tests-procedures/urine-cytology/basics/definition/prc-20020408>, 3 pages.
Tewhey et al. "Microdroplet-based PCR enrichment for large-scale targeted sequencing." Nature biotechnology 27.11 (2009): 1025-1031.
The Human Cell Lineage Flagship Initiative, Human Cell Lineage Tree, 2010, [retrieved on Dec. 1, 2015]. Retrieved from the Internet: <URL:http://www.lineage-flagship.eu/>, 1 page.
Tug et al. "Exercise-induced increases in cell free DNA in human plasma originate predominantly from cells of the haematopoietic lineage." Exercise immunology review 21 (2015): 164-173.
Turajlic et al. "Whole genome sequencing of matched primary and metastatic acral melanomas." Genome research 22.2 (2012): 196-207.
Turajlic et al. "Whole genome sequencing of matched primary and metastatic acral melanomas." Supplementary Figures. Genome research 22.2 (2012): 1-43.
Turajlic et al. "Whole genome sequencing of matched primary and metastatic acral melanomas." Supplementary Tables. Genome research 22.2 (2012): 1-532.
Vaisvila et al. "EM-seq: detection of DNA methylation at single base resolution from picograms of DNA." BioRxiv (2019): 1-38.
Valadi et al. "Exosome-mediated transfer of mRNAs and microRNAs is a novel mechanism of genetic exchange between cells." Nature cell biology 9.6 (2007): 654-659.
Vale et al. "Does anti-EGFR therapy improve outcome in advanced colorectal cancer? A systematic review and meta-analysis." Cancer treatment reviews 38.6 (2012): 618-625.
Van Driel et al. "A text-mining analysis of the human phenome." European journal of human genetics 14.5 (2006): 535-542.
Variant Detection in Massively Parallel Sequencing Data, VarScan, 2009, [retrieved on Apr. 29, 2019]. Retrieved from the Internet: <URL:www.varscan.sourceforge.net.>, 4 pages.
Vasan, R. "Biomarkers of cardiovascular disease: molecular basis and practical considerations." Circulation 113.19 (2006): 2335-2362.
Velculescu et al. "Characterization of the yeast transcriptome." Cell 88.2 (1997): 243-251.
Velculescu et al. "Serial analysis of gene expression." Science 270.5235 (1995): 484-487.
Vietsch et al. "Circulating DNA and micro-RNA in patients with pancreatic cancer." Pancreatic disorders & therapy 5.2 (2015): 1-17.
Vinay et al. "Immune evasion in cancer: Mechanistic basis and therapeutic strategies." Seminars in cancer biology. vol. 35. Academic Press (2015): S185-S198.
Vincent et al. "Helicase-dependent isothermal DNA amplification." EMBO reports 5.8 (2004): 795-800.
Vos et al. "AFLP: a new technique for DNA fingerprinting." Nucleic acids research 23.21 (1995): 4407-4414.
Wagle et al. "High-throughput detection of actionable genomic alterations in clinical tumor samples by targeted, massively parallel sequencing." Cancer discovery 2.1 (2012): 82-93.
Walker et al. "Strand displacement amplification-an isothermal, in vitro DNA amplification technique." Nucleic acids research 20.7 (1992): 1691-1696.
Wang et al. "Clonal evolution in breast cancer revealed by single nucleus genome sequencing." Nature 512.7513 (2014): 155-160.
Wang, K. "Annovar Documentation," Annovar, 2010 [retrieved on Apr. 29, 2019]. Retrieved from the Internet: <URL:annovar.openbioinformatics.org/en/latest>, 7 pages.
Warren et al. "Targeted assembly of short sequence reads." PloS one 6.5 (2011): 1-6.
Wasserstrom et al. "Reconstruction of cell lineage trees in mice." PloS one 3.4 (2008): 1-11.
Westin et al. "Anchored multiplex amplification on a microelectronic chip array." Nature Biotechnology 18.2 (2000): 199-204.
Wikipedia "Gradient boosting," Wikipedia, 2020. Retrieved from the Internet: <URL:https://en.wikipedia.org/w/index.php?title=Gradient_boosting&oldid=957594903>, 8 pages.

(56) References Cited

OTHER PUBLICATIONS

Wright et al. "The use of cell-free fetal nucleic acids in maternal blood for non-invasive prenatal diagnosis." Human reproduction update 15.1 (2009): 139-151.
Xiao et al. "Identifying mRNA, microRNA and protein profiles of melanoma exosomes." PLoS One 7.10 (2012): 1-15.
Yang et al. "Clinical whole-exome sequencing for the diagnosis of mendelian disorders." New England Journal of Medicine 369.16 (2013): 1502-1511.
Yeung et al. "LOH in the HLA class I region at 6p21 is associated with shorter survival in newly diagnosed adult glioblastoma." Clinical Cancer Research 19.7 (2013): 1816-1826.
Yi et al. "Sequencing of fifty human exomes reveals adaptation to high altitude." Science 329.5987 (2010): 75-78.
Yu et al. "Chapter 3 MarkDuplicates: A practical introduction to GATK 4 on Biowulf." 2021 [retrieved on Apr. 7, 2022]. Retrieved from the Internet: <URL:https://hpc.nih.gov/training/gatk_tutorial/markdup.html>, 6 pages.
Yu et al. "Mung bean nuclease treatment increases capture specificity of microdroplet-PCR based targeted DNA enrichment." Plos one 9.7 (2014): 1-7.
Zeerleder, S. "The struggle to detect circulating DNA." Critical Care 10 (2006): 1-3.
Zheng et al. "Estimating and accounting for tumor purity in the analysis of DNA methylation data from cancer studies." Genome biology 18 (2017): 1-14.
Pasaniuc et al. "Extremely low-coverage sequencing and imputation increases power for genome-wide association studies." Nature genetics 44.6 (2012): 631-635.
Pathak et al. "Circulating cell-free DNA in plasma/serum of lung cancer patients as a potential screening and prognostic tool." Clinical chemistry 52.10 (2006): 1833-1842.
Petition for Inter-Partes Review of U.S. Pat. No. 11,584,968, IPR2024-00170, Nov. 30, 2023, 6 pages.
Pierce et al. "Linear-after-the-exponential polymerase chain reaction and allied technologies: Real-time detection strategies for rapid, reliable diagnosis from single cells." Single Cell Diagnostics: Methods and Protocols (2007): 65-85.
Podlaha et al. "Evolution of the cancer genome." Trends in Genetics 28.4 (2012): 155-163.
Pritchard et al. "ColoSeq provides comprehensive lynch and polyposis syndrome mutational analysis using massively parallel sequencing." The Journal of Molecular Diagnostics 14.4 (2012): 357-366.
Punnoose et al. "Molecular biomarker analyses using circulating tumor cells." PloS one 5.9 (2010): 1-12.
Pyke et al. "Precision neoantigen discovery using large-scale immunopeptidomes and composite modeling of MHC peptide presentation." bioRxiv (2021): 1-37.
Pyke et al. "Precision neoantigen discovery using large-scale immunopeptidomes and composite modeling of MHC peptide presentation." Molecular & Cellular Proteomics 20 (2021): 1-19.
QIAamp® DNA Mini Kit and QIAamp DNA Blood Mini Kit Handbook, QIAGEN, Feb. 2003, 68 pages.
Ralph et al. "Consistency of VDJ rearrangement and substitution parameters enables accurate B cell receptor sequence annotation." PLoS computational biology 12.1 (2016): 1-25.
Riaz et al. "Tumor and microenvironment evolution during immunotherapy with nivolumab." Cell 171.4 (2017): 934-949.
Richter, S. "Fecal DNA screening in colorectal cancer." Canadian Journal of Gastroenterology and Hepatology 22.7 (2008): 631-633.
Riester et al. "PureCN: copy number calling and SNV classification using targeted short read sequencing." Source Code for Biology and Medicine 11.13 (2016): 1-13.
Roberts et al. "The predictive capacity of personal genome sequencing." Science translational medicine 4.133 (2012): 1-9.
Robinson et al. "Strategies for exome and genome sequence data analysis in disease-gene discovery projects." Clinical genetics 80.2 (2011): 127-132.
Robinson et al. "The Human Phenotype Ontology: a tool for annotating and analyzing human hereditary disease." The American Journal of Human Genetics 83.5 (2008): 610-615.
Rogozin et al. "Somatic mutation hotspots correlate with DNA polymerase η error spectrum." Nature immunology 2.6 (2001): 530-536.
Rosenfeld et al. "Novel multi-nucleotide polymorphisms in the human genome characterized by whole genome and exome sequencing." Nucleic acids research 38.18 (2010): 6102-6111.
Ross et al. "Characterizing and measuring bias in sequence data." Genome biology 14 (2013): 1-20.
Ross et al. "Whole cancer genome sequencing by next-generation methods." American journal of clinical pathology 136.4 (2011): 527-539.
Ross, D. "Introduction to oncogenes and molecular cancer medicine." Springer Science & Business Media (1998): 1-10.
Saeys et al. "A review of feature selection techniques in bioinformatics." Bioinformatics 23.19 (2007): 2507-2517.
Sahraeian et al. "Deep convolutional neural networks for accurate somatic mutation detection." Nature communications 10.1 (2019): 1-10.
Saiki et al. "Analysis of enzymatically amplified beta-globin and HLA-DQ alpha DNA with allele-specific oligonucleotide probes." Nature 324.6093 (1986): 163-166.
Sambrook et al. "Molecular cloning: A Laboratory Manual, 4th Edition." 448 (2012): 1-26.
Samuels et al. "Genetic mosaics and the germ line lineage." Genes 6.2 (2015): 216-237.
Sandri et al. "Apoptosis, DNA damage and ubiquitin expression in normal and mdx muscle fibers after exercise." FEBS letters 373.3 (1995): 291-295.
Saunders et al. "Strelka: accurate somatic small-variant calling from sequenced tumor-normal sample pairs." Bioinformatics 28.14 (2012): 1811-1817.
Schmitt et al. "Detection of ultra-rare mutations by next-generation sequencing." Proceedings of the National Academy of Sciences 109.36 (2012): 14508-14513.
Schwarzenbach et al. "Detection and monitoring of cell-free DNA in blood of patients with colorectal cancer." Annals of the New York Academy of Sciences 1137.1 (2008): 190-196.
Scitable, "Mendelian Trait," Scitable by Nature Education, 2014, [retrieved on Sep. 12, 2022]. Retrieved from the Internet: <URL:https://web.archive.org/web/20140825124707/https://www.nature.com/scitable/definition/mendelian-trait-174/>, 2 pages.
Shaw et al. "Genomic analysis of circulating cell-free DNA infers breast cancer dormancy." Genome research 22.2 (2012): 220-231.
Shen et al. "A hidden Markov model for copy number variant prediction from whole genome resequencing data." BMC bioinformatics 12.Suppl 6 (2011): 1-7.
Shendure et al. "Next-generation DNA sequencing." Nature biotechnology 26.10 (2008): 1135-1145.
Shigemizu et al. "A practical method to detect SNVs and indels from whole genome and exome sequencing data." Scientific reports 3.1 (2013): 1-6.
Shigemizu et al. "A practical method to detect SNVs and indels from whole genome and exome sequencing data." Supplementary Information. Scientific reports 3.1 (2013): 1-3.
Shim et al. "HLA-corrected tumor mutation burden and homologous recombination deficiency for the prediction of response to PD-(L) 1 blockade in advanced non-small-cell lung cancer patients." Annals of Oncology 31.7 (2020): 902-911.
Sims et al. "Sequencing depth and coverage: key considerations in genomic analyses." Nature Reviews Genetics 15.2 (2014): 121-132.
Singleton et al. "Phevor combines multiple biomedical ontologies for accurate identification of disease-causing alleles in single individuals and small nuclear families." The American Journal of Human Genetics 94.4 (2014): 599-610.
Smyth, G. "Limma: linear models for microarray data." Bioinformatics and computational biology solutions using R and Bioconductor. New York, NY: Springer New York (2005): 397-420.
Snyder et al. "Genetic Basis for Clinical Response to CTLA-4 Blockade in Melanoma." New England Journal of Medicine (2014): 1-11.

(56) References Cited

OTHER PUBLICATIONS

Song et al. "A reference methylome database and analysis pipeline to facilitate integrative and comparative epigenomics." PloS one 8.12 (2013): 1-9.
Soni et al. "Progress toward ultrafast DNA sequencing using solid-state nanopores." Clinical chemistry 53.11 (2007): 1996-2001.
Spalding et al. "Retrospective birth dating of cells in humans." Cell 122.1 (2005): 133-143.
Specification Sheet for Access Array™ System, Fluidigm, 2012, 4 pages.
Stemmer et al. "Single-step assembly of a gene and entire plasmid from large numbers of oligodeoxyribonucleotides." Gene 164.1 (1995): 49-53.
Stevanovic et al. "Landscape of immunogenic tumor antigens in successful immunotherapy of virally induced epithelial cancer." Science 356.6334 (2017): 200-205.
Sudhakar et al. "Characterization of clonal immunoglobulin heavy (IGH) VDJ gene rearrangements and the complementarity-determining region in South Indian patients with precursor B-cell acute lymphoblastic leukemia." Blood research 52.1 (2017): 55-61.
Sulston et al. "Post-embryonic cell lineages of the nematode, Caenorhabditis elegans." Developmental biology 56.1 (1977): 110-156.
Adessi et al. "Solid phase DNA amplification: characterisation of primer attachment and amplification mechanisms." Nucleic acids research 28.20 (2000): 1-8.
Agilent, "SureSelectXT Target Enrichment System for the Illumina Platform," Agilent Technologies, 2021, 102 pages.
Akey et al. "Haplotypes vs single marker linkage disequilibrium tests: what do we gain?" European Journal of Human Genetics 9.4 (2001): 291-300.
Albert et al. "Direct selection of human genomic loci by microarray hybridization." Nature methods 4.11 (2007): 903-905.
Alter et al. "Clinical and molecular features associated with biallelic mutations in FANCD1/BRCA2." Journal of medical genetics 44.1 (2007): 1-9.
Anderson et al. "Next generation DNA sequencing and the future of genomic medicine." Genes 1.1 (2010): 38-69.
Anzar et al. "NeoMutate: an ensemble machine learning framework for the prediction of somatic mutations in cancer." BMC medical genomics 12 (2019): 1-14.
ARUP Laboratories, "Exome Sequencing with Symptom-Guided Analysis," 2013, 2 pages.
Asan et al. "Comprehensive comparison of three commercial human whole-exome capture platforms." Genome biology 12 (2011): 1-12.
Ausubel et al. "Current Protocols in Molecular Biology." New York, Greene Publishing Associates and Wiley-Interscience (1987): 1-8.
Bainbridge et al. "Whole exome capture in solution with 3 Gbp of data." Genome biology 11 (2010): 1-8.
Baird et al. "Developing recombinant antibodies for biomarker detection." Cancer Biomarkers 6.5-6 (2010): 271-279.
Bamshad et al. "Exome sequencing as a tool for Mendelian disease gene discovery." Nature Reviews Genetics 12.11 (2011): 745-755.
Beck et al. "Profile of the circulating DNA in apparently healthy individuals." Clinical chemistry 55.4 (2009): 730-738.
Behjati et al. "Genome sequencing of normal cells reveals developmental lineages and mutational processes." Nature 513.7518 (2014): 422-425.
Benesova et al. "Mutation-based detection and monitoring of cell-free tumor DNA in peripheral blood of cancer patients." Analytical biochemistry 433.2 (2013): 227-234.
Bent et al. "Enriching pathogen transcripts from infected samples: a capture-based approach to enhanced host-pathogen RNA sequencing." Analytical Biochemistry 438.1 (2013): 90-96.
Bentley et al. "Accurate whole human genome sequencing using reversible terminator chemistry." Nature 456.7218 (2008): 53-59.
Biesecker et al. "A genomic view of mosaicism and human disease." Nature Reviews Genetics 14.5 (2013): 307-320.
Bischoff et al. "Cell-free fetal DNA and intact fetal cells in maternal blood circulation: implications for first and second trimester non-invasive prenatal diagnosis." Human reproduction update 8.6 (2002): 493-500.
Blanco et al. "Highly efficient DNA synthesis by the phage ϕ 29 DNA polymerase: Symmetrical mode of DNA replication." Journal of Biological Chemistry 264.15 (1989): 8935-8940.
Blaschko, A. "The nerve distribution in the skin in their relation to the diseases of the skin: a report to the VII Congress of the German Society of Dermatology, held at Wroclaw May 28-30, 1901." Leipzig, W. Braumeuller, 1901, 60 pages.
Blomquist et al. "Targeted RNA-sequencing with competitive multiplex-PCR amplicon libraries." PloS one 8.11 (2013): 1-14.
Boers et al. "High-throughput multilocus sequence typing: bringing molecular typing to the next level." PloS one 7.7 (2012): 1-8.
Bonadona et al. "Cancer risks associated with germline mutations in MLH1, MSH2, and MSH6 genes in Lynch syndrome." Jama 305.22 (2011): 2304-2310.
Boulesteix et al. "Evaluating microarray-based classifiers: an overview." Cancer informatics 6 (2008): 77-97.
Braslavsky et al. "Sequence information can be obtained from single DNA molecules." Proceedings of the National Academy of Sciences 100.7 (2003): 3960-3964.
Browne et al. "Increased promoter methylation in exfoliated breast epithelial cells in women with a previous breast biopsy." Epigenetics 6.12 (2011): 1425-1435.
Brunstein, J. "In-depth coverage: some useful NGS terms." Medical Laboratory Observer (MLO) 46.11 (2014): 1-5.
Bryzgunova et al. "Isolation and comparative study of cell-free nucleic acids from human urine." Annals of the New York Academy of Sciences 1075.1 (2006): 334-340.
Burrell et al. "The causes and consequences of genetic heterogeneity in cancer evolution." Nature 501.7467 (2013): 338-345.
Carlson et al. "Decoding cell lineage from acquired mutations using arbitrary deep sequencing." Nature methods 9.1 (2012): 78-80.
Cell fate map adapted from the Gilberts Developmental Biology, Fourth edition, Figure 9.1, Apr. 16, 2014, [retrieved on Sep. 27, 2022]. Retrieved from the Internet: <URL:http://biology.stackexchange.com/questions/16555/where-does-the-fate-map-of-a-human-embryo-end>, 3 pages.
Chan et al. "Cancer genome scanning in plasma: detection of tumor-associated copy number aberrations, single-nucleotide variants, and tumoral heterogeneity by massively parallel sequencing." Clinical chemistry 59.1 (2013): 211-224.
Chang et al. "Role of bacteria in oncogenesis." Clinical microbiology reviews 23.4 (2010): 837-857.
Chapman et al. "Initial genome sequencing and analysis of multiple myeloma." Nature 471.7339 (2011): 467-472.
Chen et al. "A comprehensive, highly accurate genomics platform for precision immunotherapy: Simultaneously characterize tumors and the TME from a single FFPE sample." Personalis (2019): 1.
Chiu et al. "Cell-free DNA fragmentomics: the new "Omics" on the block." Clinical chemistry 66.12 (2020): 1480-1484.
Chiu et al. "Effects of blood-processing protocols on fetal and total DNA quantification in maternal plasma." Clinical chemistry 47.9 (2001): 1607-1613.
Choi et al. "Genetic diagnosis by whole exome capture and massively parallel DNA sequencing." Proceedings of the National Academy of Sciences 106.45 (2009): 19096-19101.
Chu et al. "Statistical model for whole genome sequencing and its application to minimally invasive diagnosis of fetal genetic disease." Bioinformatics 25.10 (2009): 1244-1250.
Clark et al. "Performance comparison of exome DNA sequencing technologies." Nature biotechnology 29.10 (2011): 908-914.
Colella et al. "QuantiSNP: an Objective Bayes Hidden-Markov Model to detect and accurately map copy number variation using SNP genotyping data." Nucleic acids research 35.6 (2007): 2013-2025.
Craig et al. "Identification of genetic variants using bar-coded multiplexed sequencing." Nature methods 5.10 (2008): 887-893.
Cronn et al. "Multiplex sequencing of plant chloroplast genomes using Solexa sequencing-by-synthesis technology." Nucleic acids research 36.19 (2008): 1-11.

(56) References Cited

OTHER PUBLICATIONS

Cruz et al. "Applications of machine learning in cancer prediction and prognosis." Cancer informatics 2 (2006): 59-77.
Damani et al. "Characterization of circulating endothelial cells in acute myocardial infarction." Science translational medicine 4.126 (2012): 1-20.
Danovi, S. "A sequencing revolution in cancer." Milestones, Milestone 6, Nature, (2021): 1 page.
Davies et al. "Indications for hematopoietic cell transplantation in acute leukemia." Biology of Blood and Marrow Transplantation 14.1 (2008): 154-164.
Dawe et al. "Cell migration from baby to mother." Cell adhesion & migration 1.1 (2007): 19-27.
Human Genome Overview, "GRCh37.p13." Genome Reference Consortium, Jun. 28, 2013, [retrieved on Sep. 12, 2022]. Retrieved from the Internet: <URL:https://www.ncbi.nlm.nih.gov/grc/human>, 2 pages.
Human Genome Overview, "GRCh38.p12." Genome Reference Consortium, Dec. 21, 2017 [retrieved on Sep. 12, 2022]. Retrieved from the Internet: <URL:https://www.ncbi.nlm.nih.gov/assembly/GCF_000001405.38/>, 4 pages.
Illumina Technical Note: Informatics, "Sequencing Coverage Calculation Methods for Human Whole-Genome Sequencing: An overview of Illumina coverage calculation methods using BaseSpace or third-party analysis tools," Illumina, 2014, 3 pages.
Illumina Technical Note: Sequencing, "Estimating Sequencing Coverage: Before starting a sequencing experiment, you should know the depth of sequencing you want to achieve. This technical note helps you estimate that coverage." Illumina, 2014, 2 pages.
Illumina, "Sequencing Coverage for NGS Experiments: Coverage Depth Recommendations." Illumina, 2024. Retrieved from the Internet: <URL:https://www.illumina.com/science/technology/next-generation-sequencing/plan-experiments/coverage.html>, 3 pages.
Illumina.org "AmpliSeq for Illumina." Oct. 28, 2020, retrieved from the Internet: https://web.archive.org/web/20201021103737/https://www.illumina.com/products/by-brand/ampliseq/custom-panels.html>, 3 pages.
International Search Report and Written Opinion in PCT/US2015/058483, mailed Mar. 7, 2016, 12 pages.
Ishii et al. "Optimization of annealing temperature to reduce bias caused by a primer mismatch in multitemplate PCR." Applied and environmental microbiology 67.8 (2001): 3753-3755.
Ito et al. "Cancer neoantigens: a promising source of immunogens for cancer immunotherapy." J Clin Cell Immunol 6.322 (2015): 1-7.
Jang et al. "Tumor mutation burden, immune checkpoint crosstalk and radiosensitivity in single-cell RNA sequencing data of breast cancer." Radiotherapy and Oncology 142 (2020): 202-209.
Jenjaroenpun et al. "Characterization of RNA in exosomes secreted by human breast cancer cell lines using next-generation sequencing." PeerJ 1 (2013): 1-24.
Jiang et al. "Plasma DNA end-motif profiling as a fragmentomic marker in cancer, pregnancy, and transplantation." Cancer Discovery 10.5 (2020): 664-673.
Jung et al. "Cell-free DNA in the blood as a solid tumor biomarker-a critical appraisal of the literature." Clinica chimica acta 411.21-22 (2010): 1611-1624.
Kalatskaya et al. "ISOWN: accurate somatic mutation identification in the absence of normal tissue controls." Genome medicine 9 (2017): 1-18.
Kaper et al. "Parallel preparation of targeted resequencing libraries from 480 genomic regions using multiplex PCR on the Access Array system." Cancer Research 70.8 (2010): 1164.
Karam et al. "Apoptosis in carcinogenesis and chemotherapy." Netherlands: Springer (2009): 1-18.
Karolchik et al. "The UCSC Table Browser data retrieval tool." Nucleic acids research 32 (2004): D493-D496.
Khurana et al. "Integrative annotation of variants from 1092 humans: application to cancer genomics." Science 342.6154 (2013): 1-11.
Khurana et al. "Integrative annotation of variants from 1092 humans: application to cancer genomics." Supplementary Materials. Science 342.6154 (2013): 1-97.
Kiialainen et al. "Performance of microarray and liquid based capture methods for target enrichment for massively parallel sequencing and SNP discovery." PLoS One 6.2 (2011): 1-10.
Kinde et al. "Detection and quantification of rare mutations with massively parallel sequencing." Proceedings of the National Academy of Sciences 108.23 (2011): 9530-9535.
Koboldt et al. "VarScan: variant detection in massively parallel sequencing of individual and pooled samples." Bioinformatics 25.17 (2009): 2283-2285.
Kokawa et al. "Apoptosis in the human uterine endometrium during the menstrual cycle." The Journal of Clinical Endocrinology & Metabolism 81.11 (1996): 4144-4147.
Koren et al. "Differential relationship of DNA replication timing to different forms of human mutation and variation." The American Journal of Human Genetics 91.6 (2012): 1033-1040.
Kosuri et al. "Large-scale de novo DNA synthesis: technologies and applications." Nature methods 11.5 (2014): 499-507.
Kothari et al. "Emerging technologies for rapid identification of bloodstream pathogens." Clinical Infectious Diseases 59.2 (2014): 272-278.
Krumm et al. "Copy number variation detection and genotyping from exome sequence data." Genome research 22.8 (2012): 1525-1532.
Kuchler et al. "Buccal cells DNA extraction to obtain high quality human genomic DNA suitable for polymorphism genotyping by PCR-RFLP and Real-Time PCR." Journal of Applied Oral Science 20 (2012): 467-471.
Laktionov et al. "Cell-surface-bound nucleic acids: Free and cell-surface-bound nucleic acids in blood of healthy donors and breast cancer patients." Ann. NY Acad. Sci 1022 (2004): 221-227.
Lam et al. "Performance comparison of whole-genome sequencing platforms." Nature biotechnology 30.1 (2012): 78-82.
Lam et al. "Time course of early and late changes in plasma DNA in trauma patients." Clinical Chemistry 49.8 (2003): 1286-1291.
Larson et al. "SomaticSniper: identification of somatic point mutations in whole genome sequencing data." Bioinformatics 28.3 (2012): 311-317.
Lathe, R. "Synthetic oligonucleotide probes deduced from amino acid sequence data: theoretical and practical considerations." Journal of Molecular Biology 183.1 (1985): 1-14.
Leamon et al. "A massively parallel PicoTiterPlate™ based platform for discrete picoliter-scale polymerase chain reactions." Electrophoresis 24.21 (2003): 3769-3777.
Leary et al. "Detection of chromosomal alterations in the circulation of cancer patients with whole-genome sequencing." Science translational medicine 4.162 (2012): 1-21.
Leary et al. "Development of personalized tumor biomarkers using massively parallel sequencing." Science translational medicine 2.20 (2010): 1-15.
Lee et al. "Performance evaluation method for read mapping tool in clinical panel sequencing." Genes & genomics 40 (2018): 189-197.
Lee et al. "Simultaneous profiling of chromatin accessibility and methylation on human cell lines with nanopore sequencing." Nature methods 17.12 (2020): 1191-1199.
Lee et al. "The mutation spectrum revealed by paired genome sequences from a lung cancer patient." Nature 465.7297 (2010): 473-477.
Levin et al. "Targeted next-generation sequencing of a cancer transcriptome enhances detection of sequence variants and novel fusion transcripts." Genome biology 10 (2009): 1-8.
Ley et al. "DNA sequencing of a cytogenetically normal acute myeloid leukaemia genome." Nature 456.7218 (2008): 66-72.
Li et al. "Novel computational methods for increasing PCR primer design effectiveness in directed sequencing." BMC bioinformatics 9 (2008): 1-12.
Li et al. "The Sequence Alignment/MAP format and SAMtools." Bioinformatics 25.16 (2009): 2078-2079.
Liao et al. "Targeted massively parallel sequencing of maternal plasma DNA permits efficient and unbiased detection of fetal alleles." Clinical chemistry 57.1 (2011): 92-101.

(56) References Cited

OTHER PUBLICATIONS

Liu et al. "Computational approaches for characterizing the tumor immune microenvironment." Immunology 158.2 (2019): 70-84.
Liu et al. "Integrative molecular and clinical modeling of clinical outcomes to PD1 blockade in patients with metastatic melanoma." Nature medicine 25.12 (2019): 1916-1927.
Liu et al. "Placental mosaicism for trisomy 13: a challenge in providing the cell-free fetal DNA testing." Journal of assisted reproduction and genetics 31 (2014): 589-594.
Lizardi et al. "Mutation detection and single-molecule counting using isothermal rolling-circle amplification." Nature genetics 19.3 (1998): 225-232.
Lo et al. "Presence of fetal DNA in maternal plasma and serum." The lancet 350.9076 (1997): 485-487.
Lo et al. "Rapid clearance of fetal DNA from maternal plasma." The American Journal of Human Genetics 64.1 (1999): 218-224.
Lou et al. "High-throughput DNA sequencing errors are reduced by orders of magnitude using circle sequencing." Proceedings of the National Academy of Sciences 110.49 (2013): 19872-19877.
Lu et al. "A synthetic biology approach identifies the mammalian UPR RNA ligase RtcB." Molecular cell 55.5 (2014): 758-770.
Lu et al. "Cancer immunotherapy targeting neoantigens." Seminars in immunology 28.1 (2016): 22-27.
Lysov et al. "Efficiency of sequencing by hybridization on oligonucleotide matrix supplemented by measurement of the distance between DNA segments." DNA Sequence 6.2 (1996): 65-73.
Madeleine et al. "Comprehensive analysis of HLA-A, HLA-B, HLA-C, HLA-DRB1, and HLA-DQB1 loci and squamous cell cervical cancer risk." Cancer research 68.9 (2008): 3532-3539.
Maluf et al. "The urine microRNA profile may help monitor post-transplant renal graft function." Kidney international 85.2 (2014): 439-449.
Mamanova et al. "Target-enrichment strategies for next-generation sequencing." Nature methods 7.2 (2010): 111-118.
Marguerat et al. "RNA-seq: from technology to biology." Cellular and molecular life sciences 67 (2010): 569-579.
Margulies et al. "Genome sequencing in microfabricated high-density picolitre reactors." Nature 437.7057 (2005): 376-380.
Market et al. "V(D)J recombination and the evolution of the adaptive immune system." PLoS biology 1.1 (2003): 624-627.
Marsh, S. "Pyrosequencing applications." Methods Mol Biol. (2007): 15-24.
Marusyk et al. "Tumor heterogeneity: causes and consequences." Biochimica et Biophysica Acta (BBA)-Reviews on Cancer 1805.1 (2010): 105-117.
Masuzaki et al. "Detection of cell free placental DNA in maternal plasma: direct evidence from three cases of confined placental mosaicism." Journal of medical genetics 41.4 (2004): 289-292.
Mcbride et al. "Use of cancer-specific genomic rearrangements to quantify disease burden in plasma from patients with solid tumors." Genes, Chromosomes and Cancer 49.11 (2010): 1062-1069.
Mercer et al. "Targeted sequencing for gene discovery and quantification using RNA CaptureSeq." Nature protocols 9.5 (2014): 989-1009.
Mertes et al. "Targeted enrichment of genomic DNA regions for next-generation sequencing." Briefings in functional genomics 10.6 (2011): 374-386.
Meyerson et al. "Advances in understanding cancer genomes through second-generation sequencing." Nature Reviews Genetics 11.10 (2010): 685-696.
Michaelson et al. "Whole-genome sequencing in autism identifies hot spots for de novo germline mutation." Cell 151.7 (2012): 1431-1442.
Miller et al. "Basic concepts of microarrays and potential applications in clinical microbiology." Clinical microbiology reviews 22.4 (2009): 611-633.
Misawa et al. "Significance of chromosomal alterations and mutations of the N-RAS and TP53 genes in relation to leukemogenesis of acute myeloid leukemia." Leukemia research 22.7 (1998): 631-637.
Mitra et al. "In situ localized amplification and contact replication of many individual DNA molecules." Nucleic Acids Research 27.24 (1999): e34-e39.
Moore et al. "Direct screening of blood by PCR and pyrosequencing for a 16S rRNA gene target from emergency department and intensive care unit patients being evaluated for bloodstream infection." Journal of clinical microbiology 54.1 (2016): 99-105.
Moss et al. "Comprehensive human cell-type methylation atlas reveals origins of circulating cell-free DNA in health and disease." Nature communications 9.1 (2018): 1-12.
Moudrianakis et al. "Base sequence determination in nucleic acids with the electron microscope, III. Chemistry and microscopy of guanine-labeled DNA." Proceedings of the National Academy of Sciences 53.3 (1965): 564-571.
Muniappan et al. "The DNA polymerase β replication error spectrum in the adenomatous polyposis coli gene contains human colon tumor mutational hotspots." Cancer research 62.11 (2002): 3271-3275.
Murray et al. "Improved double-stranded DNA sequencing using the linear polymerase chain reaction." Nucleic Acids Research 17.21 (1989): 8889.
Murtaza et al. "Non-invasive analysis of acquired resistance to cancer therapy by sequencing of plasma DNA." Nature 497.7447 (2013): 108-112.
Naxerova et al. "Hypermutable DNA chronicles the evolution of human colon cancer." Proceedings of the National Academy of Sciences 111.18 (2014): E1889-E1898.
Naxerova et al. "Using tumour phylogenetics to identify the roots of metastasis in humans." Nature reviews Clinical oncology 12.5 (2015): 258-272.
Newman et al. "An ultrasensitive method for quantitating circulating tumor DNA with broad patient coverage." Nature medicine 20.5 (2014): 548-554.
Newman et al. "An ultrasensitive method for quantitating circulating tumor DNA with broad patient coverage." Supplementary Tables. Nature medicine 20.5 (2014): 1-151.
Newman et al. "Integrated digital error suppression for improved detection of circulating tumor DNA." Nature biotechnology 34.5 (2016): 547-555.
Ng et al. "Exome sequencing identifies the cause of a mendelian disorder." Nature genetics 42.1 (2010): 30-35.
Ng et al. "Targeted capture and massively parallel sequencing of 12 human exomes." Nature 461.7261 (2009): 272-276.
Notice of Allowance in U.S. Appl. No. 14/929,075, mailed Jul. 25, 2018, 13 pages.
Novocraft Technologies SDN BHD, 2014, [retrieved on Apr. 29, 2019]. Retrieved from the Internet: <URL:http://www.novocraft.com/>, 2 pages.
Nucleosome Position by MNase-seq from Encode-Stanford-BYU, 2011-2012 [retrieved on Dec. 1, 2015]. Retrieved from the Internet: <URL:http://hgdownload.cse.ucsc.edu/goldenPath/hg19/encodeDCC/wgEncodeSydhNsome/>, 2 pages.
Ochman et al. "Genetic applications of an inverse polymerase chain reaction." Genetics 120.3 (1988): 621-623.
Oesper et al. "Quantifying tumor heterogeneity in whole-genome and whole-exome sequencing data." Bioinformatics 30.24 (2014): 3532-3540.
Park, A. "Scientists Devise a Blood Test to Predict Heart Attack." Time Magazine. (2012): 1-2.
Ozsolak et al. "Direct RNA sequencing." Nature 461.7265 (2009): 814-818.
Office Action in U.S. Appl. No. 14/929,075, mailed May 27, 2016, 19 pages.
Office Action in U.S. Appl. No. 14/929,075, mailed Nov. 18, 2016, 10 pages.
Office Action in U.S. Appl. No. 14/929,075, mailed Oct. 5, 2017, 11 pages.
Office Action in U.S. Appl. No. 17/065,406, mailed Dec. 14, 2020, 16 pages.
Office Action in U.S. Appl. No. 17/065,406, mailed Mar. 23, 2021, 14 pages.

(56) References Cited

OTHER PUBLICATIONS

Okosun et al. "Integrated genomic analysis identifies recurrent mutations and evolution patterns driving the initiation and progression of follicular lymphoma." Nature genetics 46.2 (2014): 176-181.
Okosun et al. "Whole Genome Sequencing in Sequential Biopsies Reveals the Genetic Evolution of Follicular Lymphoma to Transformed Follicular Lymphoma." (2012): 1-3.
Ju et al. "Extensive genomic and transcriptional diversity identified through massively parallel DNA and RNA sequencing of eighteen Korean individuals." Nature genetics, 43(8), pp. 745-752. Available at: https://doi.org/10.1038/ng.872. (2011).
Ju et al. "A transforming KIF5B and RET gene fusion in lung adenocarcinoma revealed from whole-genome and transcriptome sequencing," Genome Research, 22(3), pp. 436-445. Available at: https://doi.org/10.1101/gr.133645.111. (2011).
Seo et al. "The transcriptional landscape and mutational profile of lung adenocarcinoma." Genome Research, 22(11), pp. 2109-2119. Available at: https://doi.org/10.1101/gr.145144.112. (2012).
Shah et al. "Mutational evolution in a lobular breast tumour profiled at single nucleotide resolution." Nature, 461(7265), pp. 809-813. Available at: https://doi.org/10.1038/nature08489. (2009).

METHODS FOR USING MOSAICISM IN NUCLEIC ACIDS SAMPLED DISTAL TO THEIR ORIGIN

CROSS-REFERENCE

This application is a continuation of U.S. patent application Ser. No. 19/073,665, filed Mar. 7, 2025, which is a continuation of U.S. patent application Ser. No. 18/613,618, filed Mar. 22, 2024, now U.S. Pat. No. 12,270,083, which is a continuation of U.S. patent application Ser. No. 17/828,572, filed May 31, 2022, now U.S. Pat. No. 11,965,214, which is a continuation of U.S. patent application Ser. No. 17/748,200, filed May 19, 2022, now U.S. Pat. No. 11,649,507, which is a continuation of U.S. patent application Ser. No. 17/494,513, filed Oct. 5, 2021, now U.S. Pat. No. 11,584,968, which is a divisional application of U.S. patent application Ser. No. 16/132,123, filed Sep. 14, 2018, now U.S. Pat. No. 11,142,802, which is a continuation of U.S. patent application Ser. No. 14/929,075, filed Oct. 30, 2015, now U.S. Pat. No. 10,125,399, which claims priority to U.S. Provisional Patent Application No. 62/072,936, filed Oct. 30, 2014, each of which is entirely incorporated herein by reference.

BACKGROUND

Many diseases may occur in locations of the body which are difficult to access without surgery or similarly invasive procedures. Thus it can be difficult to detect these diseases early, when a medical response may be most effective, and it can be difficult to monitor the progression of disease after it has been detected, especially if it requires screens which are expensive and/or invasive. In an attempt to respond to this challenge, many diagnostic tests in routine clinical use sample bodily fluids such as blood and urine which are easier to access, and analyze them for constituents reflective of the health status of the individual. In particular, the fluids may contain molecular or biological constituents which can be derived from multiple bodily locations (see, for example, Yahya et al., "The Clinical Utilization of Circulating Cell-Free DNA (CCFDNA) in Blood of Cancer Patients", International Journal of Molecular Sciences, 2013; Leary et al., "Detection of Chromosomal Alterations in the Circulation of Cancer Patients with Whole-Genome Sequencing", Science Translational Medicine, 2012; each of which is entirely incorporated herein by reference). However, when nucleic acids are detected in the body, distal from their source, there is no general method to know what the source tissue was. Thus if the quantity or other characteristic of the nucleic acids is indicative of disease, a physician may not know where the disease is located. In addition, because nucleic acids may have combined from many sources in the body, the sensitivity to detect a nucleic acid signal from any one part of the body may be limited by the presence of other nucleic acid signals from other parts of the body.

SUMMARY

The present disclosure provides methods for generating a mutation map for a subject and using the mutation map to determine the source of a given nucleic acid sequence or portion thereof in the subject. This may be used to determine, for example, the source of a disease in the subject, such as cancer. The source of the nucleic acid sequence or portion thereof may be determined by comparing the sequence to the mutation map. Examples of mutations maps include a spatial mutation map and a developmental mutation map.

Methods of the present disclosure can be used to detect and monitor a disease in a subject. For example, when nucleic acid molecules (also "nucleic acids" herein) are sampled distal from their sources in the body of a subject, the "nucleic acid signals" from many sources can be combined. Provided herein are methods to discriminate between these combined signals, so that they can be detected concurrently without mutual interference and without loss of information with respect to the source(s). This improves sensitivity and provides spatial localization of the source of each signal within the body.

An aspect provides a method for detecting differential mutations in a blood sample of a subject, comprising: a) separating the blood sample into at least a first component that includes cell-free or surface-bound nucleic acid molecules and a second component that includes leukocytes; b) extracting nucleic acid molecules from the first and second components; c) independently sequencing extracted nucleic molecules from the first and second components; and d) comparing with a programmed computer processor nucleic acid sequences of nucleic acid molecules of the first and second components to identify differential mutations.

In some embodiments, the method further comprises (e) identifying a source of the cell-free or surface-bound nucleic acid molecules based on the differential mutations. In some embodiments, the method further comprises providing a report. In some embodiments, the method further comprises providing a therapeutic intervention based on an identification of the source. In some embodiments, the report is provided on an electronic display having a user interface. In some embodiments, the source is identified as a tissue or group of tissues of the subject. In some embodiments, the method further comprises comparing the differential mutation(s) to a mutation map of the subject to identify the source. In some embodiments, the mutation map is a developmental mutation map. In some embodiments, the mutation map is a spatial mutation map. In some embodiments, the nucleic acid sequences of the extracted nucleic molecules from the first and second components are stored in computer memory.

In some embodiments, the method comprises identifying variants in nucleic acid molecules of the first component with respect to nucleic acid molecules of the second component. In some embodiments, the nucleic acid molecules of the second component are extracted by disrupting the leukocytes. In some embodiments, the nucleic acid molecules comprise deoxyribonucleic acid (DNA). In some embodiments, the cell-free or surface-bound nucleic acid molecules are cell-free DNA. In some embodiments, the cell-free or surface-bound nucleic acid molecules are surface-bound DNA. In some embodiments, the nucleic acid molecules comprise ribonucleic acid (RNA). In some embodiments, the nucleic molecules extracted from the first and second components are sequenced in a combined pool.

Another aspect provides a method for generating a mutation map of a subject that relates a mutation to a source of the mutation, comprising: a) obtaining nucleic acid samples from different tissues of the subject; b) sequencing nucleic molecules in the nucleic acid samples; c) identifying with a programmed computer processor differential mutations in nucleic acid sequences of nucleic acid molecules sequenced in (b); and d) generating in computer memory a relationship between the differential mutations and the different tissues to provide the mutation map of the subject.

In some embodiments, the mutation map is a developmental mutation map. In some embodiments, (d) of the method comprises (i) assigning the differential mutations on a developmental tree and (ii) generating the developmental mutation map from the developmental tree. In some embodiments, the developmental mutation map is generated using a hierarchical tree clustering algorithm.

In some embodiments, the mutation map is a spatial mutation map. In some embodiments, (d) of the method comprises (i) assigning the differential mutations on a spatial tree and (ii) generating the spatial mutation map from the body spatial map. In some embodiments, the spatial mutation map is generated using a hierarchical tree clustering algorithm.

In some embodiments, the method further comprises providing a report with the mutation map (e.g., developmental mutation map and/or spatial mutation map). In some embodiments, the report is provided on an electronic display having a user interface. In some embodiments, the nucleic acid sequences of the nucleic acid molecules sequenced in (c) are stored in computer memory. In some embodiments, (c) in the method comprises identifying variants in the nucleic acid sequences. In some embodiments, the blood sample is a whole blood sample. In some embodiments, the nucleic acid molecules comprise deoxyribonucleic acid (DNA). In some embodiments, the nucleic acid molecules comprise ribonucleic acid (RNA). In some embodiments, the nucleic molecules extracted from the biological samples are sequenced in a combined pool. In some embodiments, the nucleic acid samples are obtained from a blood sample of the subject.

In some embodiments, the sequencing comprises whole genome sequencing. In some embodiments, the sequencing comprises targeted genome sequencing. In some embodiments, the sequencing comprises untargeted genome sequencing. In some embodiments, the untargeted genome sequencing comprises whole genome sequencing. In some embodiments, the targeted sequencing includes at least one mutational hotspot. In some embodiments, the sequencing comprises redundant sequencing. The redundant sequencing can be duplex sequencing, Safe-SeqS or circular sequencing.

In some embodiments, the nucleic acid samples are obtained from at least one tissue with increased apoptosis. In some embodiments, the method further comprises inducing the increased apoptosis by one or more conditions selected from the group consisting of physical stress, targeted drugs, radiation and heat. In some embodiments, at least a subset of the nucleic acid samples are obtained from a blood sample, saliva sample, buccal swab, urine sample, semen sample, spinal fluid sample, skin shave biopsy, colon needle biopsy, nasal mucosal biopsy, testicular needle biopsy, endometrial biopsy, nerve biopsy by root canal, gastric endoscopic biopsy, metastatic tumor or breast milk of the subject. In some embodiments, (a) of the method comprises obtaining a nucleic acid sample from blood drawn at a first location of the subject having relatively high concentrations of cell-free nucleic acid molecules from a given tissue and a second location having low concentrations of cell-free nucleic acid molecules from the given tissue. In some embodiments, the method further comprises identifying mutations specific to the given tissue through differential analysis of nucleic acid sequences generated at the first location and second location. In some embodiments, the different tissues are non-cancerous tissues. In some embodiments, at least a subset of the nucleic acid samples is obtained from a blood sample of the subject.

Another aspect provides a method for monitoring state(s) of health of one or more tissues of a subject, comprising: a) at least one nucleic acid molecule from a blood sample of the subject; b) sequencing the nucleic acid molecule to generate a nucleic acid sequence of the nucleic acid molecule; c) identifying one or more mutations in the nucleic acid sequence; and d) using a mutation map of the subject in computer memory, identifying with a programmed computer processor a tissue of the subject associated with the nucleic acid molecule based on the one or more mutations identified in (c).

In some embodiments, the method further comprises providing a report with the tissue identified in (d). In some embodiments, the report is provided on an electronic display having a user interface. In some embodiments, (c) of the method comprises identifying variants in the nucleic acid sequences. In some embodiments, the blood sample is a whole blood sample. In some embodiments, the nucleic acid molecules comprise deoxyribonucleic acid (DNA). In some embodiments, the nucleic acid molecules comprise ribonucleic acid (RNA). In some embodiments, the nucleic acid molecule is a cell-free nucleic acid molecule. In some embodiments, the nucleic acid molecule is a surface-bound nucleic acid molecule.

In some embodiments, the method further comprises determining a state of health of the tissue. In some embodiments, the state is determined by comparing a quantity of the nucleic acid molecule against a reference to identify a relative abundance of the nucleic acid molecule. In some embodiments, the reference is a reference quantity. In some embodiments, the state is determined by aligning the nucleic acid sequence or portion thereof to a genome of the subject to identify a location of the nucleic acid sequence or portion thereof, which location is indicative of the state. In some embodiments, the state is determined by comparing a nucleic acid sequence or portion thereof to a reference to determine an apoptotic pattern, necrotic pattern, or predetermined mutations. In some embodiments, the reference is a genome of the subject. In some embodiments, the method further comprises providing a report and/or a therapeutic intervention based on a determination of the state of health.

In some embodiments, the sequencing comprises whole genome sequencing. In some embodiments, the sequencing comprises targeted genome sequencing. In some embodiments, the sequencing comprises untargeted genome sequencing. In some embodiments, the untargeted genome sequencing comprises whole genome sequencing. In some embodiments, the targeted sequencing includes at least one mutational hotspot. In some embodiments, the sequencing comprises redundant sequencing. The redundant sequencing can be duplex sequencing, Safe-SeqS or circular sequencing. In some embodiments, the sequencing is with the aid of one or more primers selected for the one or more mutations. In some embodiments, the mutation map is a developmental mutation map. In some embodiments, the mutation map is a spatial mutation map.

In another aspect, a method is provided for identifying a tissue of origin of a tumor metastasis in a subject. The method comprises: a) sequencing at least one nucleic acid molecule from a tumor metastasis of the subject to generate a nucleic acid sequence of the at least one nucleic acid molecule; b) identifying one or more mutations in the nucleic acid sequence; and c) using a mutation map of the subject in computer memory, identifying with a programmed computer processor a tissue of the subject associated with the nucleic acid molecule based on the one or more mutations identified in (b), thereby identifying the tissue of origin. In some embodiments, the method may further comprise treating the subject. In some embodiments, the treating may comprise administering an anti-cancer agent to the subject that is selected based on the tissue of origin. In some embodiments, the mutation map may be a developmental mutation map. In some embodiments, the mutation map may be a spatial mutation map. In some embodiments, the at least one nucleic acid molecule may include deoxyribonucleic acid (DNA). In some embodiments, the at least one nucleic acid molecule may comprise ribonucleic acid (RNA).

Another aspect of the present disclosure provides a non-transitory computer-readable medium comprising machine-executable code that, upon execution by one or more computer processors, implements any of the methods above or elsewhere herein.

Another aspect of the present disclosure provides a computer system comprising one or more computer processors and a non-transitory computer-readable medium coupled thereto. The non-transitory computer-readable medium comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "FIGs." herein), of which:

DETAILED DESCRIPTION

Figure 1:
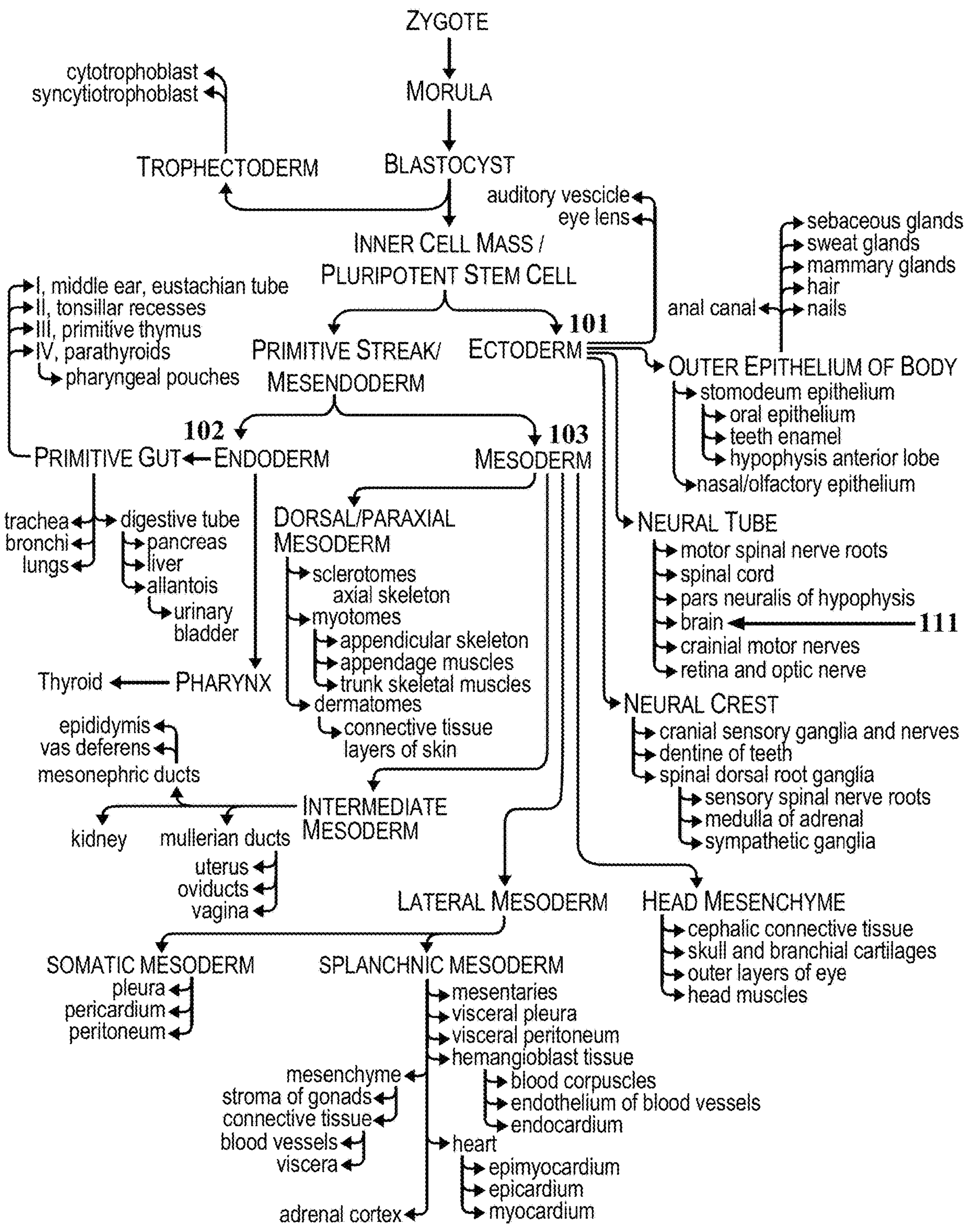
FIG. 1 shows an exemplary developmental tree.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein, generally refers to an individual having at least one biological sample that is undergoing analysis. The subject can be undergoing analysis to diagnose, predict or monitor a health, health condition, or well-being of the subject, such as, for example, identify or monitor a disease condition (e.g., cancer) in the subject. The subject can have a sample that is undergoing analysis by a researcher or a service provider, such as a healthcare professional or other individual or entity that employs methods of the present disclosure to analyze the sample.

The term "nucleic acid" as used herein generally refers to a polymeric form of nucleotides of any length. Nucleic acids can include ribonucleotides, deoxyribonucleotides or peptide nucleic acids (PNAs), that comprise purine and pyrimidine bases, or other natural, chemically or biochemically modified, non-natural, or derivatized nucleotide bases. A nucleic acid can be single or double stranded. The backbone of the polynucleotide can comprise sugars and phosphate groups, as may typically be found in deoxyribonucleic acid (DNA) or ribonucleic acid (RNA), or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleotide sequence, they allow hybridization with a naturally occurring nucleic acid sequence in solution. Typically, these analogs are derived from naturally occurring nucleosides and nucleotides by replacing and/or modifying the base, the ribose, or the phosphodiester moiety. The changes can be tailor made to stabilize or destabilize hybrid formation or enhance the specificity of hybridization with a complementary nucleic acid sequence as desired. The nucleic acid molecule may be a DNA molecule. The nucleic acid molecule may be an RNA molecule. The nucleic acid molecule may be a synthetic molecule.

The term "mutation map," as used herein, generally refers to a representation that relates a mutation to a source (e.g., tissue) in the subject. For example, a mutation can be related to a source in a developmental tree, and thus the mutation map is a developmental mutation map. In some cases, the developmental mutation map can be a cell lineage map. As another example, a mutation can be related to a body spatial map, and thus the mutation map is a spatial mutation map.

The terms "variant or derivative of a nucleic acid molecule" and "derivative or variant of a nucleic acid molecule," as used herein, generally refer to a nucleic acid molecule comprising a polymorphism. The terms "variant or derivative of a nucleic acid molecule" or "derivative or variant of a nucleic acid molecule" may also refer to a nucleic acid product that is produced from one or more assays conducted on the nucleic acid molecule. For example, a fragmented nucleic acid molecule, hybridized nucleic acid molecule (e.g., capture probe hybridized nucleic acid molecule, bead bound nucleic acid molecule), amplified nucleic acid molecule, isolated nucleic acid molecule, eluted nucleic acid molecule, and enriched nucleic acid molecule are variants or derivatives of the nucleic acid molecule.

The terms "detectable label" or "label," as used herein, generally refer to any chemical moiety attached to a nucleotide, nucleotide polymer, or nucleic acid binding factor, wherein the attachment may be covalent or non-covalent. The label can be detectable and render the nucleotide or nucleotide polymer detectable to a user or a system operated by the user. The terms "detectable label" or "label" may be used interchangeably. Detectable labels that may be used in combination with the methods disclosed herein include, for example, a fluorescent label, a chemiluminescent label, a quencher, a radioactive label, biotin, quantum dot, gold, or a combination thereof. Detectable labels include luminescent molecules, fluorochromes, fluorescent quenching agents, colored molecules, radioisotopes or scintillants. Detectable labels also include any useful linker molecule (such as biotin, avidin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase and luciferase), electron donors/acceptors, acridinium esters, dyes and calorimetric substrates. It is also envisioned that a change in mass may be considered a detectable label, as is the case of surface plasmon resonance detection.

The terms "bound", "hybridized", "conjugated", "attached", and "linked" can be used interchangeably and generally refer to the association of an object to another object. The association of the two objects to each other may be from a covalent or non-covalent interaction. For example, a capture probe hybridized nucleic acid molecule refers to a capture probe associated with a nucleic acid molecule. The capture probe and the nucleic acid molecule are in contact with each other. In another example, a bead bound nucleic acid molecule refers to a bead associated with a nucleic acid molecule.

The terms "target-specific", "targeted," and "specific" can be used interchangeably and generally refer to a subset of the genome that is a region of interest, or a subset of the genome that comprises specific genes or genomic regions. For example, the specific genomic regions can be a region that is guanine and cytosine (GC) rich. Targeted sequencing methods can allow one to selectively capture genomic regions of interest from a nucleic acid sample prior to sequencing.

Targeted sequencing involves alternate methods of sample preparation that produce libraries that represent a desired subset of the genome or to enrich the desired subset of the genome. The terms "untargeted sequencing" or "non-targeted sequencing" can be used interchangeably and generally refer to a sequencing method that does not target or enrich a region of interest in a nucleic acid sample. The terms "untargeted sequence", "non-targeted sequence," or "non-specific sequence" generally refer to the nucleic acid sequences that are not in a region of interest or to sequence data that is generated by a sequencing method that does not target or enrich a region of interest in a nucleic acid sample. The terms "untargeted sequence", "non-targeted sequence" or "non-specific sequence" can also refer to sequence that is outside of a region of interest. In some cases, sequencing data that is generated by a targeted sequencing method can comprise not only targeted sequences but also untargeted sequences.

The term "cell-free," as used herein, generally refers to a material that is present in an environment external to a cell. Such environment can include blood, plasma, serum, urine, saliva, mucosal excretions, semen, sputum, stool and tears. For example, a cell-free nucleic acid molecule (e.g., a DNA or RNA molecule) can be a nucleic acid molecule that is circulating freely in a blood stream of a subject. Examples of cell-free nucleic acid molecules include cell-free DNA (cfDNA) and cell-free RNA (cfRNA), which can include single or double stranded DNA and RNA, respectively. Cell-free nucleic acids can be found in, without limitation, blood, serum, cerebrospinal fluid (CSF), breast milk, urine, semen, and saliva.

The term "surface-bound" generally refers to a molecule that is bound, either specifically or non-specifically, to a surface. In some cases, "cell-bound" may be used interchangeably and may refer to a molecule that is bound, specifically or non-specifically, to the surface of a cell. In some cases, what is bound to the surface of the cell is a nucleic acid molecule. The surface of a cell may be "sticky" and may non-specifically bind nucleic acid molecules. In some cases, the cell in which the nucleic acid molecule is bound is also the cell in which the nucleic acid molecule was produced. In other cases, the cell in which the nucleic acid molecule is bound is not the cell in which the nucleic acid molecule was produced. "Surface-bound" or "cell-bound" nucleic acids can be isolated from the surface of which they are bound. "Cell-bound" nucleic acids can be bound to essentially any cell. In particular, cell-bound nucleic acids can be bound to blood cells (erythrocytes, leukocytes), circulating fetal cells, circulating endothelial cells, circulating tumor cells, and the like.

Genetic Mosaicism and Mutation Maps

This present disclosure provides the methods for monitoring, diagnosing, and/or detecting diseases in a subject, such as a human subject, by detecting genetic variations in the subject. In some cases, the genetic variations may include many types of genetic variation, such as aneuploidy (e.g. full or partial trisomy), uniparental disomy at the level of entire or parts of chromosomes, chromosomal abnormalities (e.g., ring chromosomes), structural variation (e.g., large deletions, duplications, translocations, inversions, etc.), small insertions and deletions (e.g., inDels), and single and multiple nucleotide polymorphisms (SNP and MNP).

This disclosure also provides the methods for detecting genetic mosaicism. In some cases, a subject may be diagnosed with a disease if one or more mosaic variants are detected (see, for example, Biesecker et al., "A genomic view of mosaicism and human disease", Nature Reviews Genetics, 2013; which is entirely incorporated herein by reference). For example, the technologies used for detecting genetic mosaicism may include karyotyping, fluorescent in-situ hybridization (FISH), chromosome painting, Sanger sequencing, array comparative genomic hybridization (aCGH), SNP arrays, next generation DNA sequencing and redundant sequencing (e.g., Duplex sequencing, Safe-SeqS, Circle sequencing).

The methods may comprise constructing a mutation map unique for each individual. In some cases, constructing the mutation map comprise mapping the genetic variations (e.g. mutations) to one or more organs and/or tissues. The mutation map may relate a mutation to a tissue and/or an organ in the subject. The mutation map can be a spatial mutation map, a developmental mutation map, or a variant or combination thereof.

In some cases, the methods disclosed herein may include generating a developmental mutation map. The developmental mutation map may be specific for an individual subject. The developmental mutation map may be generated by sampling various tissues of a subject, identifying differential mutations that occur within those various tissues, and mapping the identified mutations onto a developmental tree. As shown in the developmental tree of FIG. 1, each cell in the adult human body is derived from the original zygote by a series of cell divisions. Like a tree diagram, the development of an embryo starts with the zygote as the trunk, and then advances from branch point to branch point. Along the path each cell becomes increasingly differentiated in multiple stages.

Early on, cells separate off from the main cell mass to become the germ line and the extra-embryonic tissues (e.g. the placenta). Later, after expansion to about 200 cells, an event called gastrulation divides the cell mass into three germ layers: Ectoderm (101), Endoderm (102) and Mesoderm (103). As the process continues, further differentiation and branching occurs. For example, the Ectoderm is the source for the neurons of the brain (111), the epidermal cells of the skin, and the pigment cells (melanocytes), among others.

Figure 2:
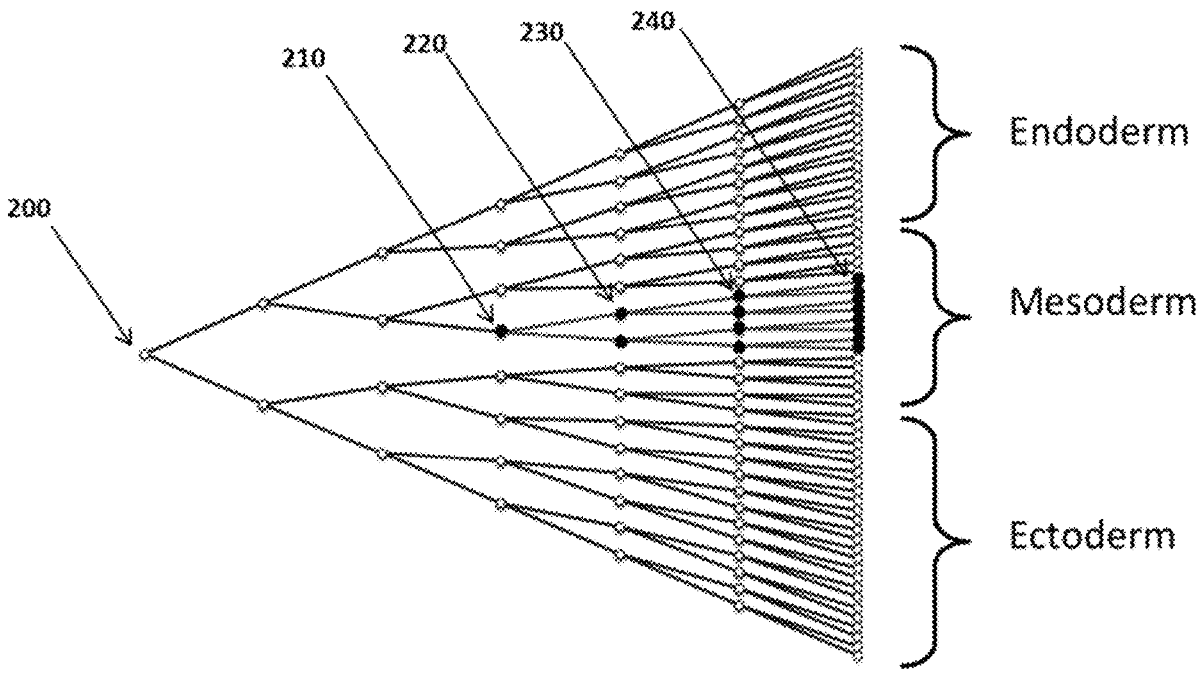
FIG. 2 shows a diagram of binary tree of cell division starting with the zygote, but with a mutation that only affects one germ layer (in this case the mesoderm)

When a post-zygotic mutation occurs, it is inherited by all of the cells "downstream" along the developmental tree. Depending on how far along that is, the affected downstream tissues may be localized, both spatially and in terms of cell type. On the other hand, a mutation which is post-zygotic, but prior to gastrulation, can have downstream progeny in all three germ layers and ultimately in all tissues of the body. They may be present there in equal fractions, or in very different fractions, depending on how many variant cells progressed down each branch of the developmental tree. In another example, when a mutation occurs in a cell post-gastrulation (i.e., after formation of the three germ layers), this mutation may exist in all of the downstream cells, but may be restricted to the germ layer of the cell from which the mutation originated. For example, FIG. 2 depicts the development of a zygote 200 from a single cell to multiple progeny cells. A mutation that occurs in a cell post-gastrulation 210 will be present in all of the downstream cells 220, 230, 240. As the originating cell is a mesoderm cell, the mutation will only occur in cells derived from the mesoderm (e.g., heart, muscle) and will not occur in cells derived from the ectoderm or the endoderm.

The methods disclosed herein may comprise taking one or more samples from one or more organs developed from one of the three germ layers. The methods disclosed herein may comprise monitoring tissues of one or more organs developed from one of the three germ layers. The methods disclosed herein may comprise predicting the origin of distal nucleic acids from one or more organs developed from one of the three germ layers. In some cases, the organs developed from the ectoderm may include epidermis, hair, nails, lens of the eye, sebaceous glands, cornea, tooth enamel, the epithelium of the mouth and nose, peripheral nervous system, adrenal medulla, melanocytes, facial cartilage, dentin of teeth, brain, spinal cord, posterior pituitary, motor neurons, retina, and neural crest. In other cases, the organs developed from the endoderm may include stomach, colon, liver, pancreas, urinary bladder, epithelial parts of trachea, lungs, pharynx, thyroid, parathyroid, and intestines. In some cases, the organs developed from the mesoderm include muscle (smooth and striated), bone, cartilage, connective tissue, adipose tissue, circulatory system, lymphatic system, dermis, genitourinary system, serous membranes, and notochord. In some cases, the mutation map is generated by mapping the mutation onto a tissue and/or organ in the developmental tree or cell fate map. For example, the mutation map is generated by mapping a mutation unique to one tissue type onto that tissue.

In some cases, the developmental mutation map can be used to identify the origin of a nucleic acid identified distally to the tissue (e.g., in blood). In some cases, a developmental mutation map, specific for an individual subject, can be used to trace the origin of a nucleic acid identified through sequencing distal nucleic acid molecules. For example, a nucleic acid in the cfDNA of a patient may be identified using the methods described herein. The presence of the nucleic acid may, for example, suggest the presence of a disease, for example, a tumor in the patient's body. However, because the nucleic acid was identified distally, rather than from a biopsy, it can be difficult to identify the tissue of origin. By using the methods described herein, the origin of the nucleic acid can be identified. In this example, the nucleic acid may be screened for one or more mosaic variants. The one or more mosaic variants may be referenced to the developmental mutation map such that the source of the mutation can be identified. It will be appreciated that, depending on when during developmental the mutation occurred, the utility of the developmental mutation map in identifying the originating tissue will vary. A mutation that occurred early in development may exist in multiple tissue types, whereas a mutation that occurred later in development may only exist in one tissue type. For example, a developmental mutation map may identify the originating tissue as endoderm if the developmental mutation occurred shortly after gastrulation. In this scenario, the exact tissue of origin may be unknown, but the number of possible sources may be limited (e.g., endodermal tissue). In another example, a developmental mutation that occurred later in development (i.e., after tissue differentiation), may restrict the tissue of origin to one or two tissues (e.g., the developmental mutation occurred in the primitive gut tube suggests the tumor of origin is pancreas, liver or allantois).

Alternatively, the methods described herein can be used to generate a spatial mutation map. A spatial mutation map can be generated by mapping a mutation onto a spatial map. In some cases, the spatial mutation map may be generated by sampling various tissues of a subject, identifying differential mutations in the various tissues, and mapping the mutations to a spatial map. In this scenario, mutations may be identified that are restricted spatially (e.g., a mutation that is found in cells on the left side of the body but not on the right side of the body). The spatial mutation map may be utilized as a reference to spatially localize mosaic variants identified through distal sampling of a subject. In a similar manner as described above for the developmental mutation map, one or more mosaic variants may be identified on a distal nucleic acid molecule. The one or more mosaic variants can be referenced to a spatial mutation map to spatially restrict a source of the nucleic acid molecule (e.g., left versus right side of the body). In some cases, the spatial map can be a body spatial map. For example, a mutation may only be found in one part (e.g., left hand) of the body but not in the others (e.g., right hand). The mutation map can be generated by mapping the mutation onto that body part (e.g., left hand) in the spatial map.

Figure 3:
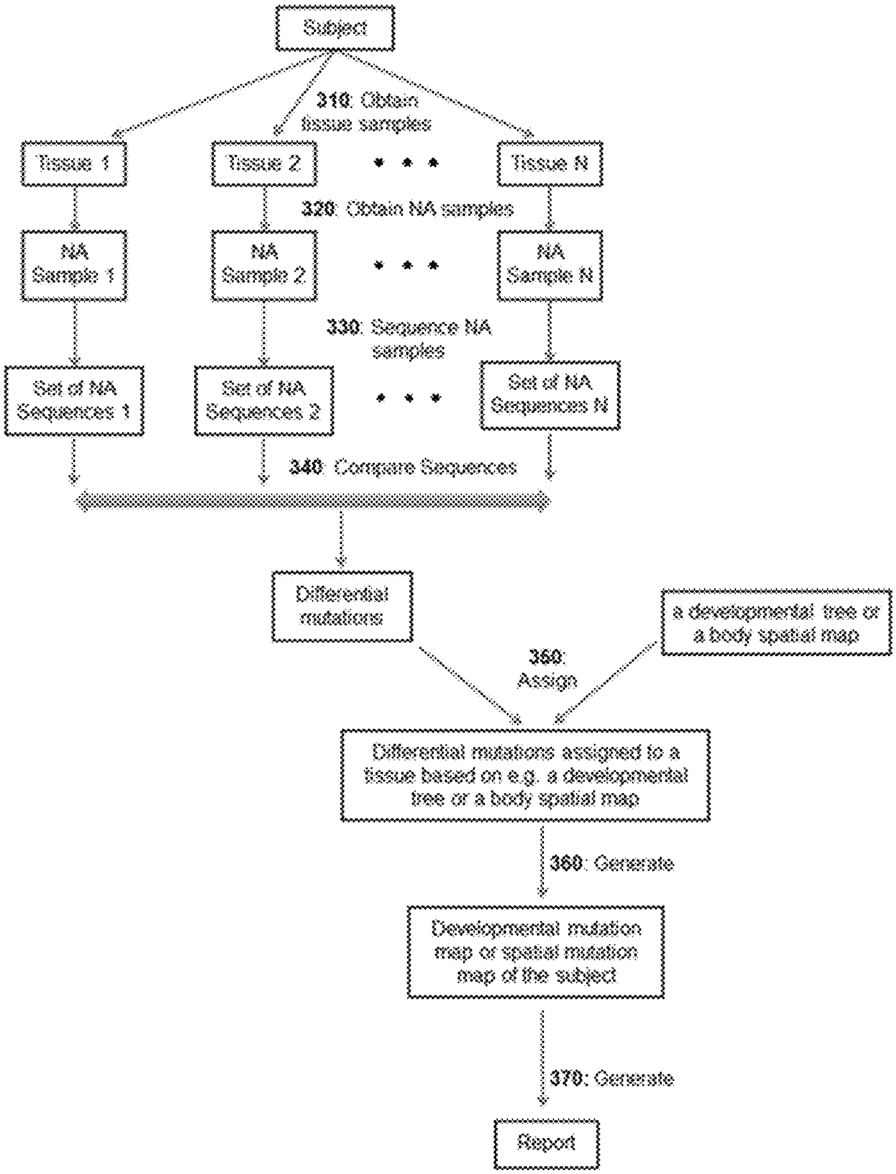
FIG. 3 shows a flowchart of the method for generating a mutation map of a subject.

Disclosed herein is a method for generating a mutation map of a subject that relates a mutation to a source of the mutation. With reference to FIG. 3, a method for generating a mutation map comprises: a) obtaining nucleic acid samples from different tissues of the subject, 310 & 320; b) sequencing nucleic molecules in the nucleic acid samples, 330; c) identifying with a programmed computer processor differential mutations in nucleic acid sequences of nucleic acid molecules sequenced in (b), 340; and d) generating in computer memory a relationship between the differential mutations and the different tissues to provide the mutation map of the subject.

Generating a relationship between the differential mutations and the different tissues may comprise (i) assigning the differential mutations on one or more tissues based on e.g., a developmental tree or a body spatial map, 350 and (ii) generating the developmental mutation map from the developmental tree or a body spatial map, 360. In a case when a developmental tree is used, the mutation map is a developmental mutation map. In a case when a body spatial map is used, the mutation map is a spatial mutation map. The mutation map may be generated using a hierarchical tree clustering algorithm. The method may further comprise providing a report with the developmental mutation map and/or the spatial mutation map.

Figure 4:
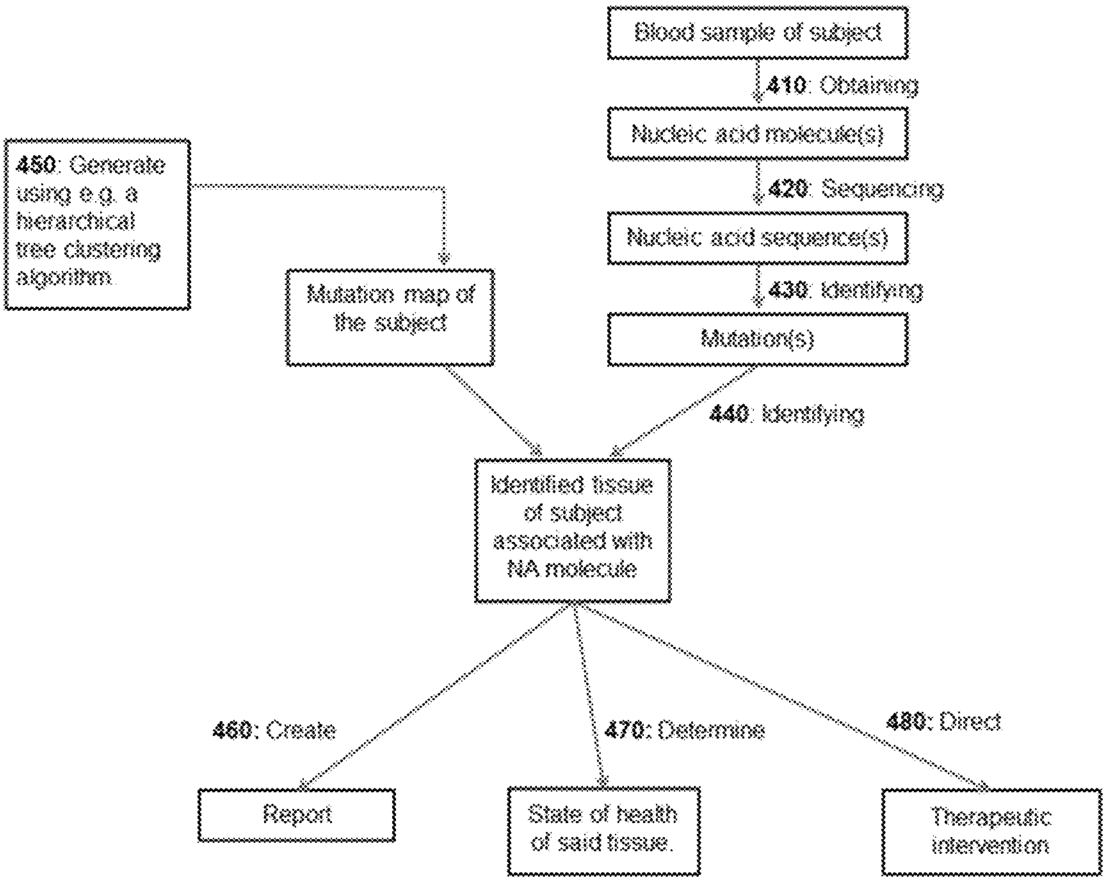
FIG. 4 shows a flowchart of the method for monitoring state(s) of health of one or more tissues of a subject.

Once a mutation map has been obtained, it may be used to determine the source of a nucleic acid molecule or portion thereof in a subject, and/or to monitor the state(s) of health of one or more tissues of a subject. With reference to FIG. 4, a method for monitoring state(s) of health one or more tissues of a subject comprise a) obtaining at least one nucleic acid molecule from a blood sample of the subject, 410; b) sequencing the nucleic acid molecule to generate a nucleic acid sequence of the nucleic acid molecule, 420; c) identifying one or more mutations in the nucleic acid sequence, 430; and d) using a mutation map of the subject 450 in computer memory, identifying with a programmed computer processor a tissue of the subject associated with the nucleic acid molecule based on the one or more mutations identified in (c), 440. The method may further comprise providing a report with the tissue identified in (d), 460. The report may be provided on an electronic display having a user interface. The method may further comprise a determination of the state of health of the subject, 470. The method may further comprise providing a therapeutic intervention based on a determination of the state of health of the subject, 480.

The method of FIG. 4 may be used to classify the one or more tissues as, for example, healthy, unhealthy, or potentially unhealthy. From such classification, a healthcare profession (e.g., a doctor) may diagnose and/or treat the subject.

Figure 5:
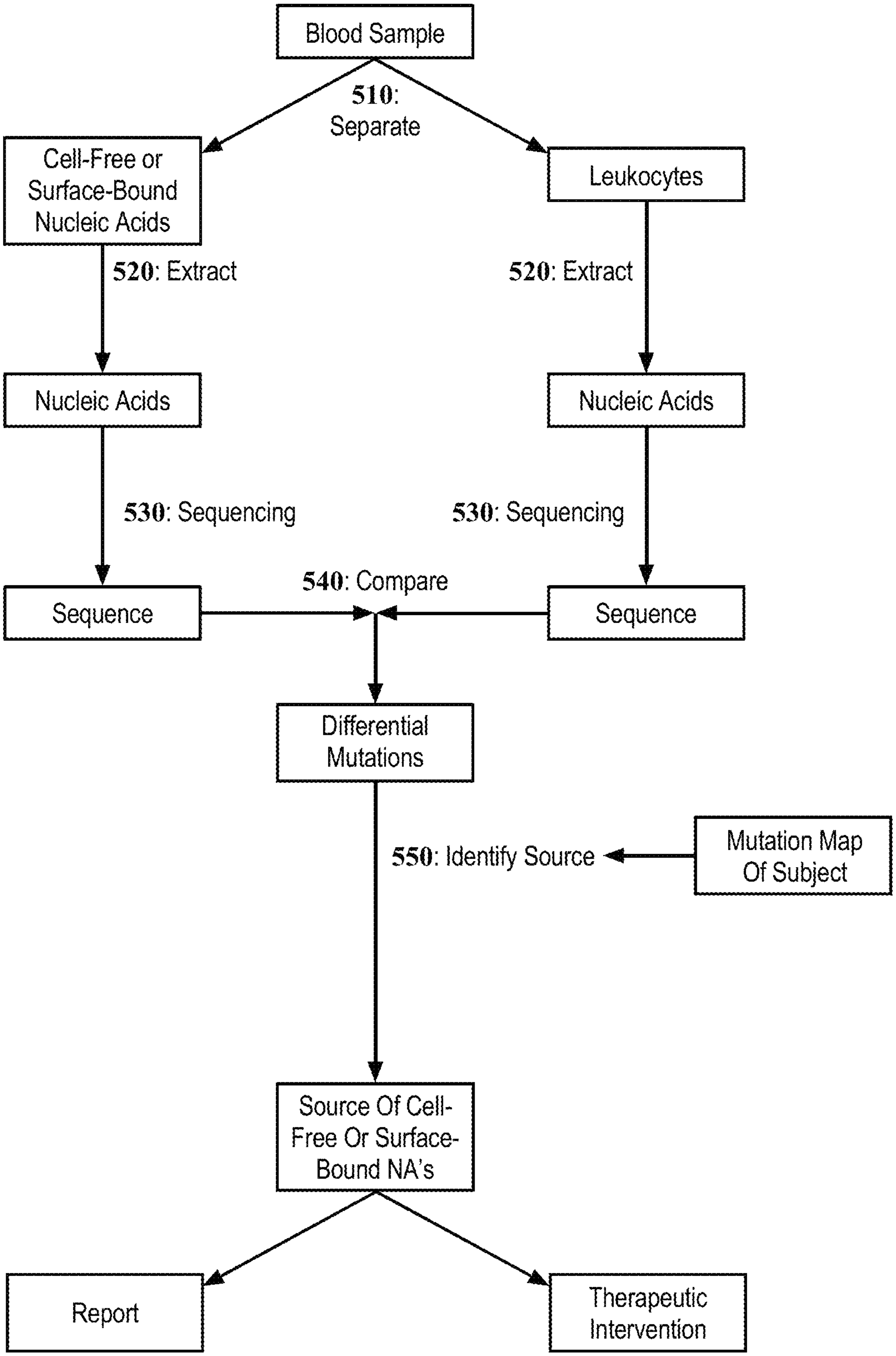
FIG. 5 shows a flowchart of the method for detecting differential mutations in a blood sample of a subject.

Methods provided herein may be used to detect differential mutations in a blood sample of a subject. With reference to FIG. 5, a method for detecting differential mutations in a blood sample of a subject comprises a) separating the blood sample into at least a first component that includes cell-free or surface-bound nucleic acid molecules and a second component that includes leukocytes, 510; b) extracting nucleic acid molecules from the first and second components, 520; c) independently sequencing extracted nucleic molecules from the first and second components, 530; and d) comparing with a programmed computer processor nucleic acid sequences of nucleic acid molecules of the first and second components to identify differential mutations, 540. The method may further comprise (e) identifying a source of the cell-free or surface-bound nucleic acid molecules based on the differential mutations, 550. The identifying the source may comprise comparing the differential mutation(s) to a mutation map (e.g., developmental mutation map or spatial mutation map) of the subject. The source may be identified as a tissue or group of tissues of the subject. The method may further comprise providing a report and/or a therapeutic intervention based on an identification of the source.

The changes in the amount and/or characteristics of cell-free DNA (cfDNA) and cell-bound DNA can be used to detect diseases (e.g., cancer). The half-life of cfDNA in blood can be shorter than that of cell-bound DNA (e.g. about 15 minutes vs several days). In a healthy individual, the amount of cell-bound DNA in a given quantity of blood may be 20× to 100× higher than the amount of cfDNA. Cell-bound DNA may be more sensitive to longer term signals (e.g. tumor growth or other diseases) and cfDNA can be used to detect transient DNA signals from transient events. These transient events may be due to the cycles of healthy physiology (e.g. sleep vs awake, monthly menstrual cycles, meals and digestion, pregnancy, etc), or due to intentional manipulation of specific parts of the body (e.g. exercise, heating/cooling, local administration or uptake of specific drugs, etc). The transient or other time varying characteristics of these distal DNA signals may allow them to be separated out from a combination of such signals.

The mosaic variants of individual parts of the body may be carried with these transient or time varying distal DNA signals. In some cases, the method provides for generating a mutation map using transient or time varying distal DNA signals. A method of generating a mutation map may involve sampling distal nucleic acid molecules of a subject during one or more transient events as described above. By observing the signals under these conditions, specific mosaic variants may be mapped to specific parts of the body without having to obtain a tissue or other sample specific to those other parts of the body. For example, cfDNA that originated in the heart may be abundant in a blood sample after cardiovascular exercise. The cfDNA can be sequenced and mutations that are specifically localized to the heart may be identified. The specific mosaic variants can be used as biomarkers for those parts of the body, even if they are not causal for medical condition. These methods can facilitate the generation of a mutation map. Similarly, disease-causing mutations may be identified by sampling distal nucleic acid molecules during one or more transient events, and the origin of those mutations can be identified with a mutation map as described above or by relating the mutations to the one or more transient events (e.g., a mutation that originated in the heart is identified after cardiovascular exercise). Thus when a change in the amount, proportion, or other characteristics of these variants is seen, it can be tied to a change in a specific part of the body.

Disclosed herein is a method of using cfDNA and cell-bound DNA complementarily. Having used the time resolution of cfDNA to correlate specific mosaic variants with specific parts of the body, the methods can be used to detect, quantify and otherwise characterize changes in these variants via cell-bound DNA, at greater sensitivity than may be possible with cfDNA from an equivalent specimen. The method, for example, can detect, quantify and otherwise characterize changes in these variants via cell-bound DNA with a specificity or sensitivity of about or greater than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5% as compared to cfDNA from an equivalent specimen. Since the changes on the time scale of blood cell turnover (a few days) or longer, the cell-bound DNA in blood may be more sensitive for detecting changes in sources of DNA. In one case, mosaic variations in the DNA may initially be characterized as from a particular part of the body by stimulating that part of the body (e.g. by exercise) and observing the corresponding transient in the cfDNA signal. Having thus associated a mosaic variant with a particular part of the body, a tumor or other disease growing in that same part of the body may be detected, by detection of that mosaic variant (e.g., biomarker) in cell-bound DNA. Because the growth of tumors may be slower than the time scale of red blood cell turnover, the cell-bound DNA may be a more sensitive detector and thus able to detect the tumor earlier.

The analysis of mosaic variants in distal nucleic acid sequences, even when those variants are not causal or predisposing for disease, can provide spatial and even organ-specificity not previously associated with assays based on them. The analysis of mosaic variation in distal nucleic acids can demultiplex otherwise combined DNA signals and can improve the sensitivity of such a test for the distal nucleic acid signal. For example, the identification of mosaic variants specific to blood cells and their precursors (e.g. bone marrow) can provide a mechanism to quantify the fraction of a cfDNA (or other distal nucleic acid) which is from blood (e.g., naturally or by rupture of blood cells in the process of obtaining the sample or conducting the assay). By subtracting out the potentially varying baseline, testing of distal nucleic acids can be more specific and/or more sensitive, for example, about or greater than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5% more specific and/or more sensitive than non-blood sources.

Samples, which are nearby on a developmental tree or a body spatial map, may be used to link specific mosaic variants to parts of the body which are difficult, expensive or invasive to assay directly. For example, because the bladder is close to the pancreas on the developmental tree (both are derived from the gut tube), mosaicism in bladder cells from urine (e.g., inexpensively and non-invasively obtainable) can be used as a surrogate marker for the pancreas (e.g., much more invasive to assay). In another case, because the spinal cord is close to the brain on the developmental tree, cells from the spinal cord, in cerebrospinal fluid, can be used as surrogate markers for the brain (e.g., expensive and much more invasive to assay.

The method may also be used to perform tumor vs normal analysis without a tissue specimen from the tumor, and thus can be used to identify specific variants in the tumor and to recommend specific anti-cancer drugs based on the mutation to be targeted. The normal analysis may be performed on white blood cells (i.e., leukocytes) prior to the development of the tumor. In some cases, the normal analysis and the tumor analysis are performed on a single blood sample. In this case, whole blood can be collected and centrifuged to separate the plasma which contains the cfDNA, the buffy coat which contains the white blood cells, and the red blood cells. Nucleic acids can be extracted from the plasma and the white blood cells and sequenced. In some cases, the cfDNA may contain distal nucleic acids that originated from a tumor. In these cases, tumor variants may be identified by identifying mosaic variants in the cfDNA that are not represented in the white blood cells ("normal"). In some cases, the tumor variants are causal variants (i.e., tumor-causing).

Sample Processing and Analysis

The methods disclosed herein may comprise providing individual sequence reads from individual distal nucleic acids. In some cases, the methods may comprise identifying mosaic mutations specific to at least one particular subset of patient's cells. The particular subset of patient's cells may comprise cells from a specific organ or set of organs. The particular subset of patient's cells may comprise cells from a spatial segment of the body (e.g., the left or right side of the body).

The methods may comprise counting the number of reads in each such subset. In some cases, counting the number of reads may be done by sequencing. In particular, counting the number of reads may be done by next-generation sequencing (NGS). For example, the individual sequence reads can be obtained using an Illumina HiSeq or MiSeq system. Alternatively, the individual sequence reads can be obtained using a digital genotyping system. In some cases, counting the number of reads may be done by monitoring one or several specific mosaic loci with assays that have analog readouts. In some cases, counting the number of reads may be done by oligo-directed single base extension. In some cases, counting the number of reads may be done by monitoring one or several specific mosaic loci with fluorescence assays. In some cases, counting the number of reads may be done by monitoring one or several specific mosaic loci with mass-spec assays. In some cases, counting the number of reads may be done by monitoring one or several specific mosaic loci with genotyping assays. In some cases, counting the number of reads may be done by monitoring one or several specific mosaic loci with arrays assays (e.g., microarray assays).

The methods may comprise normalizing the number of reads. In some cases, the number of reads exhibiting a specific mosaic variant may be normalized to the total number of reads. In some cases, the number of reads may be normalized to the time of day. In some cases, the number of reads may be normalized to the phase of menstrual cycle. In some cases, the number of reads may be normalized to the subject's body weight.

The methods may comprise comparing the number of reads, in some cases normalized, in each subset to a reference number. In some cases, the reference number is calculated from other subjects. In some cases, the reference number is calculated from the same subject.

The methods may comprise reporting the number of reads, localization, cell type, spatial position in the body, and/or other values based on the comparison. In one example, the values based on the comparison may be a statistically significant increase in read counts from a mosaic variant known to be in the patient's pancreas. The methods may comprise reporting the changes in the overall set of sequences. In some cases, the change is an increase or decrease in the overall amount of cfDNA. In some cases, the change is an increase or decrease in the ratio of certain sequences to others. For example, the certain sequences are sequences from regions frequently amplified in cancer (e.g., MET). The methods may comprise reporting the changes of mosaic and non-mosaic loci in other patient events. The patient events may be trauma, pregnancy, diagnosed diseases and/or organ transplantation.

The methods may comprise correlating results of mosaic loci with other changes in the overall set of sequences. The methods may comprise correlating results of mosaic loci with other patient events.

The methods as disclosed herein may comprise isolating cfDNA from a sample, in some cases a blood sample. In some cases, isolating cfDNA from a blood sample comprises avoiding rupture of blood cells. In some cases, isolating cfDNA from a blood sample comprises centrifuging blood first at a lower speed, and then later at a higher speed. In some cases, the blood cells contain more mosaic variants than other tissues. For example, the blood cells contain at least 110%, 120%, 130%, 140%, 150%, 160%, 170%, 180%, 190%, 200%, 250%, 300%, 350%, 400%, 450%, or 500% more mosaic variants than other tissues. In some cases, the blood-specific mosaic variants may be identified by sequencing DNA from the thin layer formed by centrifugation of blood (e.g., "Buffy Coat"). In some cases, the blood-specific mosaic variants may be identified by sequencing DNA from white blood cells. In some cases, the blood-specific signal may be identified by quantifying the signal with blood-specific mosaic variants.

The methods as disclosed herein may further comprise subtracting out the blood-specific signal from other signals. In some cases, the blood-specific signal may be monitored. For example, an increase of the blood-specific signal from the cfDNA component may indicate a disease in blood or other organs, such as liver. In some cases, subtracting out the blood-specific signal may reduce the background signal. In some cases, subtracting out the blood-specific signal may improve the sensitivity of signals from other parts of the body. In some cases, subtracting out the blood-specific signal involves subtracting out the quantity of blood-specific cfDNA from the overall quantity of cfDNA. In other cases, subtracting out the blood-specific signal involves only counting the non-blood signal at genomic loci with variants that are not identified in the blood-specific data.

The methods as disclosed herein may further comprise assaying a set of mosaic variants associated with specific parts of the body. In some cases, assaying the set of mosaic variants may detect the presence of the mosaic variants in the distal DNA at low concentrations, for example less than about 10%, 9%, 8%, 7%, 6%, 5%, 4%, 3%, 2%, or 1%. In some cases, assaying the set of mosaic variants may detect the presence of the mosaic variants in the distal DNA at even lower concentrations, for example less than about 0.9%, 0.8%, 0.7%, 0.6%, 0.5%, 0.4%, 0.3%, 0.2%, 0.1%, 0.08%, 0.06%, 0.04%, 0.02%, or 0.01%. In some cases, the methods may comprise PCR amplification of mosaic variants. In some cases, the PCR amplification of mosaic variants is more rapid than exome or whole genome sequencing. In some cases, the PCR amplification of mosaic variants takes less than 95%, 90%, 85%, 80%, 75%, 70%, 65%, 60%, 55%, or 50% of the time needed for completing an exome sequencing for the same sample. For example, the PCR amplification of mosaic variants takes less than 80% of the time needed for completing an exome sequencing for the same sample. In some cases, the PCR amplification of mosaic variants takes less than 95%, 90%, 85%, 80%, 75%, 70%, 65%, 60%, 55%, or 50% of the time needed for completing a whole genome sequencing for the same sample. For example, the PCR amplification of mosaic variants takes less than 80% of the time needed for completing a whole genome sequencing for the same sample. In some cases, the PCR amplification of mosaic variants is at least 95%, 90%, 85%, 80%, 75%, 70%, 65%, 60%, 55%, or 50% less expensive than exome or whole genome sequencing. For example, the PCR amplification of mosaic variants is at least 80% less expensive than exome or whole genome sequencing.

The methods as disclosed herein may comprise analog or digital assays. The methods as disclosed herein may comprise sequencing or genotyping. In some cases, the methods may comprise using one assay to find the mosaic variants specific to the individual first. In some cases, the methods may further comprise using a second assay once the mosaic variants specific to the individual have been identified. For example, the second assay may be specific to the individual. In some cases, the second assay may be used many times over the person's life. For example, the second assay may be used at least 1, 2, 3, 4, 5, 6, 7, 8, 9, 10, 20, 30, 40, 50 or more times over the person's life. In some cases, the second assay may use samples from many parts of the individual's body.

The methods as disclosed herein may be used to detect, monitor, diagnose, and/or treat neurologic diseases, such as amyotrophic lateral sclerosis (ALS), arteriovenous malformation, brain aneurysm, brain tumors, dural arteriovenous fistulae, epilepsy, headache, memory disorders, multiple sclerosis, Parkinson's disease, peripheral neuropathy, post-herpetic neuralgia, spinal cord tumor and stroke. In some cases, the methods may comprise taking a sample from cerebrospinal fluid.

The methods as disclosed herein may comprise identification of non-causal genetic variants. In some cases, the non-causal genetic variants occur at different proportions in different parts of the body. In some cases, the identification of the non-causal genetic variants comprises sequencing of samples from different parts of the body. In some cases, one or more samples may be obtained in the subject's life. In some cases, the methods may comprise using the one or more samples to improve the map connecting the mosaicism to the organs, cell types, and 3D physiology. In some cases, the samples are obtained by biopsy. For example, the samples can be obtained by non-invasive methods such as sampling the skin or hair. In some cases, the samples are obtained by surgery. For example, the samples can be obtained in a heart surgery to install a pacemaker. In another example, the samples can be obtained in a brain surgery to reduce the incidence of seizures. In another example, the samples can be obtained in a needle biopsy screening for breast cancer. In another example, the samples can be obtained in a surgery for hip replacement. In another example, the samples can be obtained in a surgery for cataract removal. In another example, the samples can be obtained in a surgery for caesarian section. In another example, the samples can be obtained in a surgery for colonoscopy. In another example, the samples can be obtained in a surgery for kidney transplant. In another example, the samples can be obtained in a surgery for root canal.

The methods as disclosed herein may comprise detecting structural variants (e.g., chromosomal-scale variants) in distal nucleic acids. The methods as disclosed herein may comprise detecting mosaic variants in distal nucleic acids. In some cases, the methods may comprise isolating individual cells from a sample. In some cases, the methods may comprise detecting a cell with structural variants. In some cases, the methods may comprise detecting mosaic variants in the same cell. In some cases, the methods may comprise identifying the source of the cell with structural variants by mapping the mosaic variants to the individual's mutation map.

The methods as disclosed herein may comprise detecting causal or predisposing genetic variants in distal nucleic acids. The methods may further comprise detecting non-causal variants. The methods may further comprise detecting both causal and non-causal variants. For example, the non-causal variant is a spatially mapped mosaic variant. In some cases, the methods may comprise searching for a causal variant first. Once the causal variant is detected, the methods may further comprise searching for a non-causal variant in the same cell that contains the causal variant. In some cases, searching for the non-causal variant may comprise a deep search for mosaic variants. In some cases, detecting causal and/or non-causal variants may comprise using a reverse emulsion droplet system. The reverse emulsion droplet system may be from Raindance, for example. Alternatively, detecting causal and/or non-causal variants may comprise doing a pullout from a population of large DNA molecules. The large DNA molecules may have the causal variant.

The methods as disclosed herein may comprise detecting measuring genetic mosaicism in Lynch syndrome patients. In some cases, the Lynch syndrome patient may have more mosaic mutations than healthy subjects. For example, the Lynch syndrome patient may have at least 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 120-fold, 140-fold, 160-fold, 180-fold, or 200-fold more mosaic mutations than healthy subjects. The methods may further comprise detecting, monitoring, and/or diagnosing cancer in Lynch syndrome patients. In some cases, the methods may comprise screening for colon cancer in Lynch syndrome patients. In some cases, the methods may comprise taking one or more biopsy samples during a colonoscopy. In some cases, the biopsy samples may be from locations spaced along the colon. In some cases, the methods may comprise taking biopsy samples using endometrial biopsy.

The methods as disclosed herein may comprise detecting mosaic variants using a next generation DNA sequencing technology. In some cases, detecting mosaic variants may comprise providing raw sequence reads from individual DNA. For example, the next generation DNA sequencing technology is Illumina's sequencing by synthesis technology.

The methods as disclosed herein may comprise detecting mosaic variant using a redundant sequencing technology. Next generation DNA sequencing to detect mosaic variants at low allele frequency (within a particular sample) may be limited by the error rate of the sequencing technology. This sequencing error can create a "noise floor", making it difficult to distinguish false positive variants from true positive variants at a low allelic frequency. Several techniques (including Duplex sequencing, Safe-SeqS and Circle Sequencing) have been developed to address this, each by creating multiple copies of an original DNA molecule, sequencing them separately and then combining them to create a high accuracy consensus. In some cases, a redundant sequencing technology is utilized to detect variants that occurred after gastrulation. In some cases, the variants are of allele frequencies below the "noise floor" of current next generation sequencing technologies. In these cases, the variants may be below an allele frequency in a sample of less than about 0.1%. These methods may improve the sensitivity and/or specificity of identifying mosaic variants as compared to next generation sequencing methods. In some cases, the sensitivity or specificity may be improved by at least 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5%.

The methods as disclosed herein may comprise using whole genome sequencing. In some cases, the whole genome sequencing is used to identify mosaic variants in a person. The methods may further comprise sequencing the mosaic variant using other methods. In some cases, sequencing the mosaic variant may comprise deep sequencing over a fraction of the genome. For example, the fraction of the genome may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some cases, the genome may be sequenced over 1 million, 2 million, 3 million, 4 million, 5 million, 6 million, 7 million, 8 million, 9 million, 10 million or more than 10 million bases or base pairs. In some cases, the genome may be sequenced over an entire exome (e.g., whole exome sequencing). In some cases, the deep sequencing may comprise acquiring multiple reads over the fraction of the genome. For example, acquiring multiple reads may comprise at least 2, 3, 4, 5, 6, 7, 8, 9, 10, 20, 30, 40, 50, 60, 70, 80, 90, 100, 200, 300, 400, 500, 600, 700, 800, 900, 1000, 10,000 reads or more than 10,000 reads over the fraction of the genome.

The methods as disclosed herein may comprise detecting mosaic variants in specific genomic regions. In some cases, detecting mosaic variants in specific genomic regions may comprise using methods such as PCR, Molecular Inversion Probes, or hybridization. In some cases, sequencing specific genomic regions may comprise using targeted genomic sequencing. In some cases, sequencing specific genomic regions may comprise using exome sequencing. In some cases, the specific genomic regions may comprise mutational spectra of specific human polymerases, mismatch repair genes or any combination thereof. In some cases, the specific genomic regions may comprise loci matching generic motifs inferred from the mutational spectra. In some cases, the specific genomic regions may comprise variants commonly seen somatically in cancer. In some cases, the specific genomic regions may comprise variants commonly seen de novo in other diseases, such as autism and schizophrenia. In some cases, the specific genomic regions may comprise somatic variants seen in other individuals. For example, the somatic variants seen in other individuals may be obtained from a database.

The methods as disclosed herein may comprise detecting low allelic fractions by deep sequencing. In some cases, the deep sequencing is done by next generation sequencing. In some cases, the deep sequencing is done by avoiding error-prone regions. In some cases, the error-prone regions may comprise regions of near sequence duplication, regions of unusually high or low % GC, regions of near homopolymers, di- and tri-nucleotide, and regions of near other short repeats. In some cases, the error-prone regions may comprise regions that lead to DNA sequencing errors (e.g., polymerase slippage in homopolymer sequences).

The methods as disclosed herein may comprise sequencing regions with high rates of somatic variations. The methods may comprise sequencing regions with low rates of DNA sequencing error. The methods may comprise sequencing regions with high rates of somatic variations and low rates of DNA sequencing error. By sequencing regions with high rates of somatic variations and low rates of DNA sequencing error, the amount of DNA needed per variant detected can be reduced relative to whole genome sequencing by a factor of 10 or more. In some cases, the amount of DNA needed per variant detected can be reduced relative to whole genome sequencing by a factor of 2, 3, 4, 5, 6, 7, 8, 9, 10, 20, 30, 40, 50, 60, 70, 80, 90, 100, 200, 300, 400, 500, or more.

Apoptosis is a process that involves a cascade of cellular events ultimately leading to chromosomal DNA fragmentation. Necrosis may also lead to chromosomal DNA fragmentation, however, there may be a difference in size of the DNA fragments. In some cases, the DNA fragments from necrosis may be longer than the DNA fragments from apoptosis, and in some cases, substantially longer. This difference in DNA size can be measured and used to distinguish cfDNA from apoptosis and cfDNA from necrosis. The methods as disclosed herein may comprise monitoring the genomic distribution of the cfDNA from necrosis. The methods may comprise monitoring the genomic distribution of the cfDNA from apoptosis. The methods may comprise monitoring the ratio of the cfDNA from necrosis to apoptosis. In some cases, the monitoring the genomic distribution of the cfDNA from apoptosis comprises identifying DNA in mononucleosomal and oligonucleosomal histone-DNA complexes. In some cases, monitoring the ratio of the cfDNA from necrosis to apoptosis comprises measuring the length of the cfDNA. In some cases, the average molecule length of the cfDNA from apoptosis is about 50, 75, 100, 110, 120, 130, 140, 150, 160, 170, 180, 200, 210, 220, 230, 240, 250, 300, 350, 400, 450, 500 or more base pairs. In some cases, the average molecule length of the cfDNA from necrosis is about 1000, 1500, 2000, 2500, 3000, 3500, 4000, 4500, 5000, 5500, 6000, 6500, 7000, 7500, 8000, 8500, 9000, 9500, 10000, or more base pairs. In some cases, the average molecule length of the cfDNA from necrosis is longer than the cfDNA from apoptosis. For example, the average molecule length of the cfDNA from necrosis is at least 1000, 1500, 2000, 2500, 3000, 3500, 4000, 4500, 5000, 5500, 6000, 6500, 7000, 7500, 8000, 8500, 9000, 9500, 10000 or more base pairs longer than the cfDNA from apoptosis. In some cases, the cfDNA from necrosis is distinguished from the cfDNA from apoptosis by the length of the cfDNA.

In some cases, the ratio of the cfDNA from necrosis to apoptosis can be measured using the methods described herein to identify a tumor. As a tumor grows, the core of the tumor may be starved for oxygen and nutrients which may lead to necrosis of the inner mass of tumor cells ("necrotic core"). DNA from the necrotic core may be released into the bloodstream and detected as cfDNA. The presence of cfDNA from necrosis in a blood sample may indicate the presence of tumor.

The methods as disclosed herein may comprise isolating cell-bound DNA from a sample. In some cases, the sample may be a blood sample. In some cases, isolating cell-bound DNA may further comprise isolating the red blood cell component from the blood sample first. In this case, as red blood cells do not have DNA, the DNA isolated from the red blood cell component is distal DNA that has bound to the surface of the red blood cells. In some cases, isolating the red blood cell component may comprise using centrifugation. In some cases, isolating the red blood cell component may comprise using flow cytometry. In some cases, isolating the red blood cell component may comprise using fluorescence-activated cell sorting (FACS). In some cases, the cell-bound DNA may be extracted from the red blood cell component of the blood sample. In some cases, the methods may comprise sequencing nucleic molecules in the cell-bound DNA. In some cases, the methods may comprise detecting mosaic variants in the cell-bound DNA. In some cases, the methods may comprise identifying the source of the cell-bound DNA. In some cases, the source of the cell-bound DNA may be bone marrow.

Assays

In some cases, the methods may comprise obtaining distal nucleic acids separated out from other components of the sample. For example, the methods may comprise obtaining cfDNA separated out from the DNA in the rest of the blood. In particular, cfDNA may be compared to DNA contained in the white blood cells (e.g., Leukocytes).

The methods disclosed herein may comprise isolating cfDNA from blood. In some cases, blood cells may be separated out and returned to circulation in the patient using dialysis. Alternatively, the cfDNA can be siphoned off from the blood stream without removing the blood cells using a membrane permeable to the cfDNA but not to the cells. For example, an expanded Teflon membrane may be used. In some cases, DNA may be motivated to move through the membrane electrophoretically. In some cases, methods may allow more frequent sampling of cfDNA than may normally be medically recommended if the loss of blood cells is required.

In some cases, the nucleic acid sample described herein can be subjected to a variety of assays. Assays may include, but are not limited to, sequencing, amplification, hybridization, enrichment, isolation, elution, fragmentation, detection, and quantification of one or more nucleic acid molecules. Assays may include methods for preparing one or more nucleic acid molecules.

In some cases, the nucleic acids in the nucleic acid sample described herein can be amplified. Amplification can be performed at any point during a multi reaction procedure using methods provided herein, e.g., before or after pooling of sequencing libraries from independent reaction volumes and may be used to amplify any suitable target molecule described herein.

Amplification can be performed by various methods or systems. The nucleic acids may be amplified by polymerase chain reaction (PCR), as described in, for example, U.S. Pat. Nos. 5,928,907 and 6,015,674, each of which is entirely incorporated herein by reference. Other methods of nucleic acid amplification may include, for example, ligase chain reaction, oligonucleotide ligations assay, and hybridization assay, as described in greater detail in U.S. Pat. Nos. 5,928,907 and 6,015,674, each of which is entirely incorporated herein by reference. Real-time optical detection systems may be employed, for example, as described in U.S. Pat. Nos. 5,928,907 and 6,015,674, each of which is entirely incorporated herein by reference. Other amplification methods that can be used herein include those described in U.S. Pat. Nos. 5,242,794; 5,494,810; 4,988,617; and 6,582,938, each of which is entirely incorporated herein by reference. Other amplification techniques that can be used with methods of the present disclosure can include, e.g., AFLP (amplified fragment length polymorphism) PCR (see e.g.: Vos et al. 1995. AFLP: a new technique for DNA fingerprinting. Nucleic Acids Research 23:4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324:163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164:49-53), asymmetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5(8):795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells (Methods Mol. Med. 132:65-85), long PCR, nested PCR, real-time PCR, duplex PCR, multiplex PCR, quantitative PCR, quantitative fluorescent PCR (QF-PCR), multiplex fluorescent PCR (MF-PCR), restriction fragment length polymorphism PCR (PCR-RFLP), PCK-RFLPIRT-PCR-IRFLP, polony PCR, in situ rolling circle amplification (RCA), bridge PCR, picotiter PCR, and emulsion PCR, or single cell PCR. Other suitable amplification methods can include transcription amplification, self-sustained sequence replication, selective amplification of target polynucleotide sequences, consensus sequence primed polymerase chain reaction (CP-PCR), arbitrarily primed polymerase chain reaction (AP-PCR), and degenerate oligonucleotide-primed PCR (DOP-PCR). Another method for achieving the result of an amplification of nucleic acids is ligase chain reaction (LCR), nucleic acid sequence based amplification (NASBA), Q-beta-replicase method, 3SR (see for example Fahy et al. PCR Methods Appl. 1:25-33 (1991)), or Transcription Mediated Amplification (TMA) used by Gen-Probe. TMA is similar to NASBA in utilizing two enzymes in a self-sustained sequence replication. See U.S. Pat. No. 5,299,491 herein incorporated by reference. Other methods for amplification of nucleic acids can include Strand Displacement Amplification (SDA) (Westin et al 2000, Nature Biotechnology, 18, 199-202; Walker et al 1992, Nucleic Acids Research, 20, 7, 1691-1696), or Rolling Circle Amplification (RCA) (Lizardi et al. 1998, Nature Genetics, 19:225-232).

In some cases, amplification methods can be solid-phase amplification, polony amplification, colony amplification, emulsion PCR, bead RCA, surface RCA, surface SDA, etc., as will be recognized by one of skill in the art. In some cases, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20):E87) can be used. A "polymerase colony technology" or "polony" may be used, referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

Amplification may be achieved through any process by which the copy number of a target sequence is increased, e.g., PCR. Conditions favorable to the amplification of target sequences by PCR can be optimized at a variety of operations in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the operations of denaturation of the target to be amplified (if double stranded), hybridization of one or more primers to the target, and extension of the primers by a DNA polymerase, with the operations repeated (or "cycled") in order to amplify the target sequence. Operations in this process can be optimized for various outcomes, such as to enhance yield, decrease the formation of spurious products, and/or increase or decrease specificity of primer annealing. Methods of optimization may include adjustments to the type or amount of elements in the amplification reaction and/or to the conditions of a given operation in the process, such as temperature at a particular operation, duration of a particular operation, and/or number of cycles. In some cases, an amplification reaction comprises at least 5, 10, 15, 20, 25, 30, 35, 50, or more cycles. In some cases, an amplification reaction comprises no more than 5, 10, 15, 20, 25, 35, 50, or more cycles. Cycles can contain any number of operations, such as 1, 2, 3, 4, 5, 6, 7, 8, 9, 10 or more operations. Operations can comprise any temperature or gradient of temperatures, suitable for achieving the purpose of the given operation, including but not limited to, 3' end extension (e.g., adaptor fill-in), primer annealing, primer extension, and strand denaturation. Operations can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different operations can be combined in any order. In some cases, different cycles comprising different operations are combined such that the total number of cycles in the combination is about, less that about, or more than about 5, 10, 15, 20, 25, 30, 35, 50, or more cycles.

The methods herein may further comprise conducting one or more hybridization reactions on one or more nucleic acid molecules in a sample. The hybridization reactions may comprise the hybridization of one or more capture probes to one or more nucleic acid molecules in a sample or subset of nucleic acid molecules. The hybridization reactions may comprise hybridizing one or more capture probe sets to one or more nucleic acid molecules in a sample or subset of nucleic acid molecules. The hybridization reactions may comprise one or more hybridization arrays, multiplex hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof. The hybridization reaction may comprise one or more capture probes, one or more beads, one or more labels, one or more subsets of nucleic acid molecules, one or more nucleic acid samples, one or more reagents, one or more wash buffers, one or more elution buffers, one or more hybridization buffers, one or more hybridization chambers, one or more incubators, one or more separators, or a combination thereof.

The methods disclosed herein may further comprise conducting one or more enrichment reactions on one or more nucleic acid molecules in a sample. The enrichment reactions may comprise contacting a sample with one or more beads or bead sets. The enrichment reaction may comprise differential amplification of two or more subsets of nucleic acid molecules based on one or more genomic region features. For example, the enrichment reaction comprises differential amplification of two or more subsets of nucleic acid molecules based on GC content. Alternatively, or additionally, the enrichment reaction comprises differential amplification of two or more subsets of nucleic acid molecules based on methylation state. The enrichment reactions may comprise one or more hybridization reactions. The enrichment reactions may further comprise isolation and/or purification of one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. Alternatively, or additionally, the enrichment reaction may comprise enriching for one or more cell types in the sample. The one or more cell types may be enriched by flow cytometry.

The methods disclosed herein may comprise enrichment reactions for different genomic or non-genomic regions and may comprise one or more different amplification operations to prepare libraries of nucleic acid molecules for assay. The one or more enrichment reactions may produce one or more enriched nucleic acid molecules. The enriched nucleic acid molecules may comprise a nucleic acid molecule or variant or derivative thereof. For example, the enriched nucleic acid molecules comprise one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. The enriched nucleic acid molecules may be differentiated from non-enriched nucleic acid molecules by GC content, molecular size, genomic regions, genomic region features, or a combination thereof. The enriched nucleic acid molecules may be derived from one or more assays, supernatants, eluants, or a combination thereof. The enriched nucleic acid molecules may differ from the non-enriched nucleic acid molecules by mean size, mean GC content, genomic regions, or a combination thereof.

The methods disclosed herein may further comprise conducting one or more isolation or purification reactions on one or more nucleic acid molecules in a sample. The isolation or purification reactions may comprise contacting a sample with one or more beads or bead sets. The isolation or purification reaction may comprise one or more hybridization reactions, enrichment reactions, amplification reactions, sequencing reactions, or a combination thereof. The isolation or purification reaction may comprise the use of one or more separators. The one or more separators may comprise a magnetic separator. The isolation or purification reaction may comprise separating bead bound nucleic acid molecules from bead free nucleic acid molecules. The isolation or purification reaction may comprise separating capture probe hybridized nucleic acid molecules from capture probe free nucleic acid molecules. The isolation or purification reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may further comprise conducting one or more elution reactions on one or more nucleic acid molecules in a sample. The elution reactions may comprise contacting a sample with one or more beads or bead sets. The elution reaction may comprise separating bead bound nucleic acid molecules from bead free nucleic acid molecules. The elution reaction may comprise separating capture probe hybridized nucleic acid molecules from capture probe free nucleic acid molecules. The elution reaction may comprise separating a first subset of nucleic acid molecules from a second subset of nucleic acid molecules, wherein the first subset of nucleic acid molecules differ from the second subset on nucleic acid molecules by mean size, mean GC content, genomic regions, or a combination thereof.

The methods disclosed herein may further comprise one or more fragmentation reactions. The fragmentation reactions may comprise fragmenting one or more nucleic acid molecules in a sample or subset of nucleic acid molecules to produce one or more fragmented nucleic acid molecules. The one or more nucleic acid molecules may be fragmented by sonication, needle shear, nebulisation, shearing (e.g., acoustic shearing, mechanical shearing, point-sink shearing), passage through a French pressure cell, or enzymatic digestion. Enzymatic digestion may occur by nuclease digestion (e.g., micrococcal nuclease digestion, endonucleases, exonucleases, RNAse H or DNase I). Fragmentation of the one or more nucleic acid molecules may result in fragment sized of about 100 base pairs to about 2000 base pairs, about 200 base pairs to about 1500 base pairs, about 200 base pairs to about 1000 base pairs, about 200 base pairs to about 500 base pairs, about 500 base pairs to about 1500 base pairs, and about 500 base pairs to about 1000 base pairs. The one or more fragmentation reactions may result in fragment sized of about 50 base pairs to about 1000 base pairs. The one or more fragmentation reactions may result in fragment sized of about 100 base pairs, 150 base pairs, 200 base pairs, 250 base pairs, 300 base pairs, 350 base pairs, 400 base pairs, 450 base pairs, 500 base pairs, 550 base pairs, 600 base pairs, 650 base pairs, 700 base pairs, 750 base pairs, 800 base pairs, 850 base pairs, 900 base pairs, 950 base pairs, 1000 base pairs or more.

Fragmenting the one or more nucleic acid molecules may comprise mechanical shearing of the one or more nucleic acid molecules in the sample for a period of time. The fragmentation reaction may occur for at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more seconds.

Fragmenting the one or more nucleic acid molecules may comprise contacting a nucleic acid sample with one or more beads. Fragmenting the one or more nucleic acid molecules may comprise contacting the nucleic acid sample with a plurality of beads, wherein the ratio of the volume of the plurality of beads to the volume of nucleic acid sample is about 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00 or more. Fragmenting the one or more nucleic acid molecules may comprise contacting the nucleic acid sample with a plurality of beads, wherein the ratio of the volume of the plurality of beads to the volume of nucleic acid is about 2.00, 1.90, 1.80, 1.70, 1.60, 1.50, 1.40, 1.30, 1.20, 1.10, 1.00, 0.90, 0.80, 0.70, 0.60, 0.50, 0.40, 0.30, 0.20, 0.10, 0.05, 0.04, 0.03, 0.02, 0.01 or less.

The methods disclosed herein may further comprise conducting one or more detection reactions on one or more nucleic acid molecules in a sample. Detection reactions may comprise one or more sequencing reactions. Alternatively, conducting a detection reaction comprises optical sensing, electrical sensing, or a combination thereof. Optical sensing may comprise optical sensing of a photoilluminscence photon emission, fluorescence photon emission, pyrophosphate photon emission, chemiluminescence photon emission, or a combination thereof. Electrical sensing may comprise electrical sensing of an ion concentration, ion current modulation, nucleotide electrical field, nucleotide tunneling current, or a combination thereof.

The methods disclosed herein may further comprise conducting one or more quantification reactions on one or more nucleic acid molecules in a sample. Quantification reactions may comprise sequencing, PCR, qPCR, digital PCR, or a combination thereof.

The methods disclosed herein may further comprise conducting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, or 50 or more assays on a sample comprising one or more nucleic acid molecules. The two or more assays may be different, similar, identical, or a combination thereof. For example, the methods disclosed herein comprise conducting two or more sequencing reactions. In another example, the methods disclosed herein comprise conducting two or more assays, wherein at least one of the two or more assays comprises a sequencing reaction. In yet another example, the methods disclosed herein comprise conducting two or more assays, wherein at least two of the two or more assays comprises a sequencing reaction and a hybridization reaction. The two or more assays may be performed sequentially, simultaneously, or a combination thereof. For example, the two or more sequencing reactions may be performed simultaneously. In another example, the methods disclosed herein comprise conducting a hybridization reaction, followed by a sequencing reaction. In yet another example, the methods disclosed herein comprise conducting two or more hybridization reactions simultaneously, followed by conducting two or more sequencing reactions simultaneously. The two or more assays may be performed by one or more devices. For example, two or more amplification reactions may be performed by a PCR machine. In another example, two or more sequencing reactions may be performed by two or more sequencers.

The methods disclosed herein may further comprise providing individual sequence reads from individual distal nucleic acids. For example, the individual sequence reads can be obtained using an Illumina HiSeq or MiSeq system. In another example, the individual sequence reads can be obtained using a digital genotyping system.

Performance

The methods disclosed herein can detect one or more genomic regions (i.e., copy number variation, or one or more polymorphisms) with a specificity or sensitivity of about or greater than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5%, or a positive predictive value or negative predictive value of about or at least about 80%, 85%, 90%, 95%, 95.5%, 96%, 96.5%, 97%, 97.5%, 98%, 98.5%, 99%, 99.5% or more. The methods disclosed herein can detect one or more genomic regions (i.e., copy number variation, or one or more polymorphisms) with a specificity or sensitivity of about or greater than about 50%. The methods disclosed herein can diagnose a specific condition based on the detected genomic regions such as copy number variation. The methods can diagnose a specific condition with a specificity or sensitivity of greater than 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, or 99.5%, or a positive predictive value or negative predictive value of at least 80%, 85%, 90%, 95%, 95.5%, 96%, 96.5%, 97%, 97.5%, 98%, 98.5%, 99%, 99.5% or more.

The methods disclosed herein may increase the sensitivity or specificity when compared to the sensitivity or specificity of current sequencing methods. For example without limitation, in some cases, the combined whole exome sequencing and a whole genome sequencing reactions may increase the sensitivity or specificity in detecting one or more copy number variations or diagnosing a specific condition when compared to the sensitivity or specificity of whole exome sequencing alone. The sensitivity or specificity of the methods as described herein may increase by at least about 1%, 2%, 3%, 4%, 5%, 5.5%, 6%, 6.5%, 7%, 7.5%, 8%, 8.5%, 9%, 9.5%, 10%, 10.5%, 11%, 12%, 13%, 14%, 15%, 16%, 17%, 18%, 19%, 20%, 25%, 30%, 35%, 40%, 45%, 50%, 55%, 60%, 70%, 80%, 90%, 95%., 97% or more. The sensitivity or specificity of the methods as described herein may increase by at least about 4.5-20%, about 5-15%, about 7%-12%, or about 8%-10%. In some cases, the methods disclosed herein may have a similar sensitivity or specificity when compared to the sensitivity or specificity of a high coverage whole genome sequencing alone.

In some cases, the methods as described herein comprise combining an untargeted sequencing data (e.g., low coverage whole genome sequencing data) and one or more target-specific sequencing data. The methods and system disclosed herein may have a sensitivity, specificity, positive predictive value or negative predictive value that is similar to a high coverage whole genome sequencing data alone. The sensitivity, specificity, positive predictive value or negative predictive value may be for the detection of one or more haplotypes, SNV, CNV or one or more polymorphisms. In some cases, the methods as disclosed herein comprise untargeted sequencing data (e.g., a low coverage whole genome sequencing data) that may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more SNV. In some cases, the methods as disclosed herein may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more polymorphisms, specific genes or genomic regions. In some cases, the untargeted sequencing (e.g., whole genome sequencing) in the methods as disclosed herein may have a sensitivity, specificity, positive predictive value or negative predictive value that is less than 5%, 10%, 15%, 20%, 25%, 30%, 35%, 40%, 45%, 50%, 55%, 60%, 65%, 70%, 75%, 80%, 85% or 90% for one or more SNV, one or more polymorphisms or one or more specific genes or genomic regions. In some cases, the target-specific sequencing data may have a sensitivity, specificity, positive predictive value or negative predictive value that is about, at least about or less than about 50%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98%, 99%, 99.5% or 100%. In some cases, the untargeted sequencing can have a sensitivity, specificity, positive predictive value or negative predictive value that is between about 50% to 80%.

The methods disclosed herein can detect one or more genomic regions (i.e., copy number variation, or one or more polymorphisms) with an error rate of less than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% or less. The methods disclosed herein can diagnose a specific condition based on the detected genomic regions such as copy number variation. The methods can diagnose a specific condition with an error rate of less than 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10% or less.

The percent error of the methods as described herein may be similar to current sequencing methods. For example, without limitation, in some cases, the combined whole exome sequencing and a whole genome sequencing reactions may have a percent error rate in detecting one or more copy number variations or diagnosing a specific condition when compared to the sensitivity of whole exome sequencing alone. The current sequencing methods may be a high coverage whole genome sequencing alone. The percent error rate of the methods as described herein may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%., 1.2%, 1.3%, 1.4%, 1.5%, 1.6%, 1.7%, 1.8%, 1.9%, or 2% of the current sequencing methods. The percent error rate of the methods as described herein may be less than the percent error rate of current sequencing methods. The percent error rate of the methods as described herein may be at least about 10%, 9,%, 8%, 7%, 6%, 5%, 4%, 3%, 2%, 1.75%, 1.5%, 1.25%, 1%, 0.9%, 0.8%, 0.7%, 0.6%, 0.5%, 0.4%, 0.3%, 0.2%, 0.1% less than the percent error rate of current sequencing methods. The percent error rate of the methods as described herein may be less than about 2%, 1.75%, 1.5%, 1.25%, 1%, 0.75%, 0.50%, 0.25%, 0.10%, 0.075%, 0.050%, 0.025%, or 0.001%. In some cases, the methods disclosed herein may have a similar percent error rate when compared to the sensitivity or specificity of a high coverage whole genome sequencing alone.

The error of the methods as described herein can be determined as a Phred quality score. The Phred quality score may be assigned to each base call in automated sequencer traces and may be used to compare the efficacy of different sequencing methods. The Phred quality score (Q) may be defined as a property which is logarithmically related to the base-calling error probabilities (P). The Phred quality score (Q) may be calculated as $Q=-10 \log 10P$. The Phred quality score of the methods as described herein may be similar to the Phred quality score of current sequencing methods. For example without limitation, in some cases, the combined whole exome sequencing and a low coverage whole genome sequencing reactions may have a similar Phred quality score in detecting one or more copy number variations or diagnosing a specific condition when compared to the Phred quality score of whole exome sequencing alone or a high coverage whole genome sequencing alone. The Phred quality score of the methods as described herein may be within 1, 2, 3, 4, 5, 6, 7, 8, 9, 10 of the Phred quality score of the methods as described herein. The Phred quality score of the methods as described herein may be less than the Phred quality score of the methods as described herein. The Phred quality score of the methods as described herein may be at least about 10, 9, 8, 7, 6, 5, 4, 3, 2, 1 less than the Phred quality score of the methods as described herein. The Phred quality score of the methods as described herein may be greater than 5, 6, 7, 8, 9, 10, 11, 12, 13, 14, 15, 16, 17, 18, 19, 20, 25, or 30. The Phred quality score of the methods as described herein may be greater than 35, 40, 41, 42, 43, 44, 45, 46, 47, 48, 49, 50, 51, 52, 53, 54, 55, 56, 57, 58, 59,or 60. The Phred quality score of the methods as described herein may be at least 35, 36, 37, 38, 39, 40, 41, 42, 43, 44, 45, 46, 47, 48, 49, 50, 51, 52, 53, 54, 55, 56, 57, 58, 59, 60 or more.

The accuracy of the one or more sequencing reactions may be similar to current sequencing methods in detecting and identifying one or more specific genomic regions. The current sequencing methods can be a whole exome sequencing alone or a high coverage whole genome sequencing alone. The accuracy of the methods as described herein may be within about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%., 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, or 4% of the current sequencing methods. The accuracy of the methods as described herein may be greater than the accuracy of current sequencing methods. The accuracy of the methods as described herein may be at least about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 1%, 1.1%., 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.5%, 5%, 6%, 7%, 8%, 9%, 10%, 11%, 12%, 15%, 17%, 20%, 25%, 30%, 35%, 40%, 50%, or 60% greater than the accuracy of current sequencing methods. The accuracy of the methods as described herein may be greater than about 70%, 75%, 80%, 85%, 90%, 91%, 92%, 93%, 94%, 95%, 96%, 97%, 98.25%, 98.5%, 98.75%, 99%, 99.25%, 99.5%, or 99.75%. The accuracy of the methods as described herein may be greater than about 99.1%, 99.2%, 99.3%, 99.4%, 99.5%, 99.6%, 99.7%, 99.8%, 99.9%, 99.99%, or 90.999%.

The methods disclosed herein can generate an output data identifying one or more specific genomic regions (i.e., copy number variation, or one or more polymorphisms) in a shorter time than a high coverage whole genome sequencing alone. In some cases, the methods as described herein can identify specific genomic regions in less than 1 month, 3.5 weeks, 3 weeks, 2.5 weeks, 2 weeks, 1.5 weeks or 1 week. In some cases, the methods as described herein can identify specific genomic regions in less than 6, 5, 4, 3, 2 or 1 days. In some cases, the methods as described herein can identify specific genomic regions in less than 24, 23, 22, 21, 20, 19, 18, 17, 16, 15, 14, 13, 12, 11, 10, 9, 8, 7, 6, 5, 4, 3, 2 or 1 hours. In some cases, the methods as described herein can identify specific genomic regions in less than 60, 59, 55, 50, 45, 40, 35, 30, 25, 20, 15, 10, 9, 8, 7, 6, 5, 4, 3, 2 or 1 minutes. In some cases, the methods as described herein can identify specific genomic regions in less than 10 minutes. In some cases, the methods as described herein can identify specific genomic regions in less than 5 minutes.

The methods disclosed herein can generate an output data identifying one or more specific genomic regions (i.e., copy number variation, or one or more polymorphisms) more economically or using less reagents than a high coverage whole genome sequencing alone. In some cases, the methods as described herein can identify specific genomic regions with 5%, 10%, 15%, 20%, 25%, 30%, 35%, 40%, 45%, 50%, 55%, 60%, 65%, 70%, 75%, 80%, 85%, 90% less financial charges to the customers or less reagents for sequencing reactions used.

Genomic Regions

The methods as disclosed herein may comprise, or comprise the use of, nucleic acid samples or subsets of nucleic acid molecules comprising one or more genomic regions. The methods as disclosed herein may comprise, or comprise the use of, nucleic acid samples or subsets of nucleic acid molecules comprising one or more sets of genomic regions. The one or more genomic regions may comprise one or more genomic region features. The genomic region features may comprise an entire genome or a portion thereof. The genomic region features may comprise an entire exome or a portion thereof. The genomic region features may comprise one or more sets of genes. The genomic region features may comprise one or more genes. The genomic region features may comprise one or more sets of regulatory elements. The genomic region features may comprise one or more regulatory elements. The genomic region features may comprise a set of polymorphisms. The genomic region features may comprise one or more polymorphisms. The genomic region feature may relate to the GC content, complexity, and/or mappablity of one or more nucleic acid molecules. The genomic region features may comprise one or more simple tandem repeats (STRs), unstable expanding repeats, segmental duplications, single and paired read degenerative mapping scores, GRCh37 patches, or a combination thereof. The genomic region features may comprise one or more low mean coverage regions from whole genome sequencing (WGS), zero mean coverage regions from WGS, validated compressions, or a combination thereof. The genomic region features may comprise one or more alternate or non-reference sequences. The genomic region features may comprise one or more gene phasing and reassembly genes. In some aspects of the disclosure, the one or more genomic region features are not mutually exclusive. For example, a genomic region feature comprising an entire genome or a portion thereof can overlap with an additional genomic region feature such as an entire exome or a portion thereof, one or more genes, one or more regulatory elements, etc. Alternatively, the one or more genomic region futures are mutually exclusive. For example, a genomic region comprising the noncoding portion of an entire genome may not overlap with a genomic region feature such as an exome or portion thereof or the coding portion of a gene. Alternatively, or additionally, the one or more genomic region features are partially exclusive or partially inclusive. For example, a genomic region comprising an entire exome or a portion thereof can partially overlap with a genomic region comprising an exon portion of a gene. However, the genomic region comprising the entire exome or portion thereof may not overlap with the genomic region comprising the intron portion of the gene. Thus, a genomic region feature comprising a gene or portion thereof may partially exclude and/or partially include a genomic region feature comprising an entire exome or portion thereof.

The methods as disclosed herein may comprise, or comprise the use of, nucleic acid samples or subsets of nucleic acid molecules comprising one or more genomic regions, wherein at least one of the one or more genomic regions comprises a genomic region feature comprising an entire genome or portion thereof. The entire genome or portion thereof may comprise one or more coding portions of the genome, one or more noncoding portions of the genome, or a combination thereof. The coding portion of the genome may comprise one or more coding portions of a gene encoding for one or more proteins. The one or more coding portions of the genome may comprise an entire exome or a portion thereof. Alternatively, or additionally, the one or more coding portions of the genome may comprise one or more exons. The one or more noncoding portions of the genome may comprise one or more noncoding molecules or a portion thereof. The noncoding molecules may comprise one or more noncoding RNA, one or more regulatory elements, one or more introns, one or more pseudogenes, one or more repeat sequences, one or more transposons, one or more viral elements, one or more telomeres, a portion thereof, or a combination thereof. The noncoding RNAs may be functional RNA molecules that are not translated into protein. Examples of noncoding RNAs include, but are not limited to, ribosomal RNA, transfer RNA, piwi-interacting RNA, microRNA, siRNA, shRNA, snoRNA, sncRNA, and IncRNA. Pseudogenes may be related to known genes and are typically no longer expressed. Repeat sequences may comprise one or more tandem repeats, one or more interspersed repeats, or a combination thereof. Tandem repeats may comprise one or more satellite DNA, one or more minisatellites, one or more microsatellites, or a combination thereof. Interspersed repeats may comprise one or more transposons. Transposons may be mobile genetic elements. Mobile genetic elements are often able to change their position within the genome. Transposons may be classified as class I transposable elements (class I TEs) or class II transposable elements (class II TEs). Class I TEs (e.g., retrotransposons) may often copy themselves in two stages, first from DNA to RNA by transcription, then from RNA back to DNA by reverse transcription. The DNA copy may then be inserted into the genome in a new position. Class I TEs may comprise one or more long terminal repeats (LTRs), one or more long interspersed nuclear elements (LINEs), one or more short interspersed nuclear elements (SINEs), or a combination thereof. Examples of LTRs include, but are not limited to, human endogenous retroviruses (HERVs), medium reiterated repeats 4 (MER4), and retrotransposon. Examples of LINEs include, but are not limited to, LINE1 and LINE2. SINEs may comprise one or more Alu sequences, one or more mammalian-wide interspersed repeat (MIR), or a combination thereof. Class II TEs (e.g., DNA transposons) often do not involve an RNA intermediate. The DNA transposon is often cut from one site and inserted into another site in the genome. Alternatively, the DNA transposon is replicated and inserted into the genome in a new position. Examples of DNA transposons include, but are not limited to, MER1, MER2, and mariners. Viral elements may comprise one or more endogenous retrovirus sequences. Telomeres are often regions of repetitive DNA at the end of a chromosome.

The methods as disclosed herein may comprise, or comprise the use of, nucleic acid samples or subsets of nucleic acid molecules comprising one or more genomic regions, wherein at least one of the one or more genomic regions comprises a genomic region feature comprising an entire exome or portion thereof. The exome is often the part of the genome formed by exons. The exome may be formed by untranslated regions (UTRs), splice sites and/or intronic regions. The entire exome or portion thereof may comprise one or more exons of a protein coding gene. The entire exome or portion thereof may comprise one or more untranslated regions (UTRs), splice sites, and introns.

The methods as disclosed herein may comprise, or comprise the use of, nucleic acid samples or subsets of nucleic acid molecules comprising one or more genomic regions, wherein at least one of the one or more genomic regions comprises a genomic region feature comprising a gene or portion thereof. Typically, a gene comprises stretches of nucleic acids that code for a polypeptide or a functional RNA. A gene may comprise one or more exons, one or more introns, one or more untranslated regions (UTRs), or a combination thereof. Exons are often coding sections of a gene, transcribed into a precursor mRNA sequence, and within the final mature RNA product of the gene. Introns are often noncoding sections of a gene, transcribed into a precursor mRNA sequence, and removed by RNA splicing. UTRs may refer to sections on each side of a coding sequence on a strand of mRNA. A UTR located on the 5' side of a coding sequence may be called the 5' UTR (or leader sequence). A UTR located on the 3' side of a coding sequence may be called the 3' UTR (or trailer sequence). The UTR may contain one or more elements for controlling gene expression. Elements, such as regulatory elements, may be located in the 5' UTR. Regulatory sequences, such as a polyadenylation signal, binding sites for proteins, and binding sites for miRNAs, may be located in the 3' UTR. Binding sites for proteins located in the 3' UTR may include, but are not limited to, selenocysteine insertion sequence (SECIS)

elements and AU-rich elements (AREs). SECIS elements may direct a ribosome to translate the codon UGA as selenocysteine rather than as a stop codon. AREs are often stretches consisting primarily of adenine and uracil nucleotides, which may affect the stability of an mRNA.

The methods as disclosed herein may comprise, or comprise the use of, nucleic acid samples or subsets of nucleic acid molecules comprising one or more genomic regions, wherein at least one of the one or more genomic regions comprises a genomic region feature comprising a set of genes. The sets of genes may include, but are not limited to, Mendel DB Genes, Human Gene Mutation Database (HGMD) Genes, Cancer Gene Census Genes, Online Mendelian Inheritance in Man (OMIM) Mendelian Genes, HGMD Mendelian Genes, and human leukocyte antigen (HLA) Genes. The set of genes may have one or more known Mendelian traits, one or more known disease traits, one or more known drug traits, one or more known biomedically interpretable variants, or a combination thereof. A Mendelian trait may be controlled by a single locus and may show a Mendelian inheritance pattern. A set of genes with known Mendelian traits may comprise one or more genes encoding Mendelian traits including, but are not limited to, ability to taste phenylthiocarbamide (dominant), ability to smell (bitter almond-like) hydrogen cyanide (recessive), albinism (recessive), brachydactyly (shortness of fingers and toes), and wet (dominant) or dry (recessive) earwax. A disease trait cause or increase risk of disease may be inherited in a Mendelian or complex pattern. A set of genes with known disease traits may comprise one or more genes encoding disease traits including, but are not limited to, Cystic Fibrosis, Hemophilia, and Lynch Syndrome. A drug trait may alter metabolism, optimal dose, adverse reactions and side effects of one or more drugs or family of drugs. A set of genes with known drug traits may comprise one or more genes encoding drug traits including, but are not limited to, CYP2D6, UGT1 A1 and ADRB1. A biomedically interpretable variant may be a polymorphism in a gene that is associated with a disease or indication. A set of genes with known biomedically interpretable variants may comprise one or more genes encoding biomedically interpretable variants including, but are not limited to, cystic fibrosis (CF) mutations, muscular dystrophy mutations, p53 mutations, Rb mutations, cell cycle regulators, receptors, and kinases. Alternatively, or additionally, a set of genes with known biomedically interpretable variants may comprise one or more genes associated with Huntington's disease, cancer, cystic fibrosis, muscular dystrophy (e.g., Duchenne muscular dystrophy).

The methods as disclosed herein may comprise, or comprise the use of, nucleic acid samples or subsets of nucleic acid molecules comprising one or more genomic regions, wherein at least one of the one or more genomic regions comprises a genomic region feature comprising a regulatory element or a portion thereof. Regulatory elements may be cis-regulatory elements or trans-regulatory elements. Cis-regulatory elements may be sequences that control transcription of a nearby gene. Cis-regulatory elements may be located in the 5' or 3' untranslated regions (UTRs) or within introns. Trans-regulatory elements may control transcription of a distant gene. Regulatory elements may comprise one or more promoters, one or more enhancers, or a combination thereof. Promoters may facilitate transcription of a particular gene and may be found upstream of a coding region. Enhancers may exert distant effects on the transcription level of a gene.

The methods as disclosed herein may comprise, or comprise the use of, nucleic acid samples or subsets of nucleic acid molecules comprising one or more genomic regions, wherein at least one of the one or more genomic regions comprises a genomic region feature comprising a polymorphism or a portion thereof. Generally, a polymorphism refers to a mutation in a genotype. A polymorphism may comprise one or more base changes, an insertion, a repeat, or a deletion of one or more bases. Copy number variants (CNVs), transversions, and other rearrangements are also forms of genetic variation. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are a form of polymorphisms. In some aspects of the disclosure, one or more polymorphisms comprise one or more single nucleotide variations, inDels, small insertions, small deletions, structural variant junctions, variable length tandem repeats, flanking sequences, or a combination thereof. The one or more polymorphisms may be located within a coding and/or non-coding region. The one or more polymorphisms may be located within, around, or near a gene, exon, intron, splice site, untranslated region, or a combination thereof. The one or more polymorphisms may span at least a portion of a gene, exon, intron, untranslated region.

The methods as disclosed herein may comprise, or comprise the use of, nucleic acid samples or subsets of nucleic acid molecules comprising one or more genomic regions, wherein at least one of the one or more genomic regions comprises a genomic region feature comprising one or more simple tandem repeats (STRs), unstable expanding repeats, segmental duplications, single and paired read degenerative mapping scores, GRCh37 patches, or a combination thereof. The one or more STRs may comprise one or more homopolymers, one or more dinucleotide repeats, one or more trinucleotide repeats, or a combination thereof. The one or more homopolymers may be about 7, 8, 9, 10, 11, 12, 13, 14, 15, 16, 17, 18, 19, 20 or more bases or base pairs. The dinucleotide repeats and/or trinucleotide repeats may be about 15, 16, 17, 18, 19, 20, 21, 22, 23, 24, 25, 26, 27, 28, 29, 30, 35, 40, 45, 50 or more bases or base pairs. The single and paired read degenerative mapping scores may be based on or derived from alignability of 100 mers by GEM from ENCODE/CRG (Guigo), alignability of 75 mers by GEM from ENCODE/CRG (Guigo), 100 base pair box car average for signal mappability, max of locus and possible pairs for paired read score, or a combination thereof. The genomic region features may comprise one or more low mean coverage regions from whole genome sequencing (WGS), zero mean coverage regions from WGS, validated compressions, or a combination thereof. The low mean coverage regions from WGS may comprise regions generated from Illumina v3 chemistry, regions below the first percentile of Poission distribution based on mean coverage, or a combination thereof. The Zero mean coverage regions from WGS may comprise regions generated from Illumina v3 chemistry. The validated compressions may comprise regions of high mapped depth, regions with two or more observed haplotypes, regions expected to be missing repeats in a reference, or a combination thereof. The genomic region features may comprise one or more alternate or non-reference sequences. The one or more alternate or non-reference sequences may comprise known structural variant junctions, known insertions, known deletions, alternate haplotypes, or a combination thereof. The genomic region features may comprise one or more gene phasing and reassembly genes. Examples of phasing and reassembly genes include, but are not limited to, one or more major histocompatibility complexes, blood typing, and amylase gene family. The one or more major histocompatibility complexes may comprise one or more HLA Class I, HLA Class II, or a combination thereof. The one or more HLA class I may comprise HLA-A, HLA-B, HLA-C, or a combination thereof. The one or more HLA class II may comprise HLA-DP, HLA-DM, HLA-DOA, HLA-DOB, HLA-DQ, HLA-DR, or a combination thereof. The blood typing genes may comprise ABO, RHD, RHCE, or a combination thereof.

The methods as disclosed herein may comprise, or comprise the use of, nucleic acid samples or subsets of nucleic acid molecules comprising one or more genomic regions, wherein at least one of the one or more genomic regions comprises a genomic region feature related to the GC content of one or more nucleic acid molecules. The GC content may refer to the GC content of a nucleic acid molecule. Alternatively, the GC content may refer to the GC content of one or more nucleic acid molecules and may be referred to as the mean GC content. As used herein, the terms "GC content" and "mean GC content" may be used interchangeably. The GC content of a genomic region may be a high GC content. Typically, a high GC content refers to a GC content of greater than or equal to about 65%, 70%, 75%, 80%, 85%, 90%, 95%, 97%, or more. In some aspects of the disclosure, a high GC content may refer to a GC content of greater than or equal to about 70%. The GC content of a genomic region may be a low GC content. Typically, a low GC content refers to a GC content of less than or equal to about 65%, 60%, 55%, 50%, 45%, 40%, 35%, 30%, 25%, 20%, 15%, 10%, 5%, 2%, or less.

The difference in GC content may be used to differentiate two or more genomic regions or two or more subsets of nucleic acid molecules. The difference in GC content may refer to the difference in GC content of one nucleic acid molecule and another nucleic acid molecule.

Alternatively, the difference in GC content may refer to the difference in mean GC content of two or more nucleic acid molecules in a genomic region from the mean GC content of two or more nucleic acid molecules in another genomic region. In some aspects of the disclosure, the difference in GC content refers to the difference in mean GC content of two or more nucleic acid molecules in a subset of nucleic acid molecules from the mean GC content of two or more nucleic acid molecules in another subset of nucleic acid molecules. The difference in GC content may be about 5%, 6%, 7%, 8%, 9%, 10%, 15%, 20%, 25%, 30%, 35%, 40%, or more. In some aspects of the disclosure, the difference in GC content is at least about 5%. The difference in GC content may be at least about 10%.

The methods as disclosed herein may comprise, or comprise the use of, nucleic acid samples or subsets of nucleic acid molecules comprising one or more genomic regions, wherein at least one of the one or more genomic regions comprises a genomic region feature related to the complexity of one or more nucleic acid molecules. The complexity of a nucleic acid molecule may refer to the randomness of a nucleotide sequence. Low complexity may refer to patterns, repeats and/or depletion of one or more species of nucleotide in the sequence.

The methods as disclosed herein may comprise, or comprise the use of, nucleic acid samples or subsets of nucleic acid molecules comprising one or more genomic regions, wherein at least one of the one or more genomic regions comprises a genomic region feature related to the mappablity of one or more nucleic acid molecules. The mappability of a nucleic acid molecule may refer to uniqueness of its alignment to a reference sequence. A nucleic acid molecule with low mappability may have poor alignment to a reference sequence.

The methods as disclosed herein may comprise, or comprise the use of, nucleic acid samples or subsets of nucleic acid molecules comprising one or more genomic regions comprising one or more genomic region features. In some aspects of the disclosure, a single genomic region comprises 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The two or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. In some aspects of the disclosure, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic region features. Alternatively, or additionally, two or more genomic regions comprise 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic region features.

The methods as disclosed herein may comprise, or comprise the use of, nucleic acid samples or subsets of nucleic acid molecules comprising two or more genomic regions, wherein the two or more genomic regions are differentiateable by one or more genomic region features. The methods as disclosed herein may comprise, or comprise the use of, nucleic acid samples or subsets of nucleic acid molecules comprising two or more subsets of nucleic acid molecules, wherein the two or more subsets of nucleic acid molecules are differentiateable by one or more genomic region features. The two or more genomic regions and/or the two or more subsets of nucleic acid molecules may be differentiateable by 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more genomic region features. The one or more genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, or 30 or more genomic region features.

The methods as disclosed herein may comprise, or comprise the use of, nucleic acid samples or subsets of nucleic acid molecules comprising one or more sets of genomic regions. For example, The methods as disclosed herein may, or comprise the use of, comprise nucleic acid samples or subsets of nucleic acid molecules comprising, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more sets of genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more different genomic regions. The one or more sets of genomic regions may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more identical or similar genomic regions. The one or more sets of genomic regions may comprise a combination of one or more different genomic regions and one or more identical or similar genomic regions.

The methods as disclosed herein may comprise, or comprise the use of, nucleic acid samples or subsets of nucleic acid molecules comprising one or more genomic regions, wherein at least one of the one or more genomic regions comprises a genomic region with higher mutation rates. In some cases, the methods may comprise sequencing one or more genomic mutation hot spots. For example, the mutation rates in the genomic mutation hot spots are 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more times than the average mutation rates across the genome.

Capture Probes

The methods disclosed herein may comprise, or comprise the use of, one or more capture probes, a plurality of capture probes, or one or more capture probe sets. Typically, the capture probe comprises a nucleic acid binding site. The capture probe may further comprise one or more linkers. The capture probes may further comprise one or more labels. The one or more linkers may attach the one or more labels to the nucleic acid binding site.

The methods disclosed herein may comprise, or comprise the use of, 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more capture probes or capture probe sets. The one or more capture probes or capture probe sets may be different, similar, identical, or a combination thereof.

The one or more capture probe may comprise a nucleic acid binding site that hybridizes to at least a portion of the one or more nucleic acid molecules or variant or derivative thereof in the sample or subset of nucleic acid molecules. The capture probes may comprise a nucleic acid binding site that hybridizes to one or more genomic regions. The capture probes may hybridize to different, similar, and/or identical genomic regions. The one or more capture probes may be at least about 50%, 55%, 60%, 65%, 70%, 75%, 80%, 85%, 90%, 95%, 97%, 99% or more complementary to the one or more nucleic acid molecules or variants or derivatives thereof.

The capture probes may comprise one or more nucleotides. The capture probes may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The capture probes may comprise about 100 nucleotides. The capture probes may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the capture probes comprise between about 80 nucleotides to about 100 nucleotides.

The plurality of capture probes or the capture probe sets may comprise two or more capture probes with identical, similar, and/or different nucleic acid binding site sequences, linkers, and/or labels. For example, two or more capture probes comprise identical nucleic acid binding sites. In another example, two or more capture probes comprise similar nucleic acid binding sites. In yet another example, two or more capture probes comprise different nucleic acid binding sites. The two or more capture probes may further comprise one or more linkers. The two or more capture probes may further comprise different linkers. The two or more capture probes may further comprise similar linkers. The two or more capture probes may further comprise identical linkers. The two or more capture probes may further comprise one or more labels. The two or more capture probes may further comprise different labels. The two or more capture probes may further comprise similar labels. The two or more capture probes may further comprise identical labels.

Diseases or Conditions

The methods as disclosed herein may comprise, or comprise the use of, predicting, diagnosing, and/or prognosing a status or outcome of a disease or condition in a subject based on one or more biomedical outputs. Predicting, diagnosing, and/or prognosing a status or outcome of a disease in a subject may comprise diagnosing a disease or condition, identifying a disease or condition, determining the stage of a disease or condition, assessing the risk of a disease or condition, assessing the risk of disease recurrence, assessing reproductive risk, assessing genetic risk to a fetus, assessing the efficacy of a drug, assessing risk of an adverse drug reaction, predicting optimal drug dosage, predicting drug resistance, or a combination thereof.

The samples disclosed herein may be from a subject suffering from a cancer. The sample may comprise malignant tissue, benign tissue, or a mixture thereof. The cancer may be a recurrent and/or refractory cancer. Examples of cancers include, but are not limited to, sarcomas, carcinomas, lymphomas or leukemias.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. The cancer may be a skin cancer, such as a basal cell carcinoma, squamous, melanoma, nonmelanoma, or actinic (solar) keratosis.

The cancer may be a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesothelioma. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astrocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. The cancer may be a meningioma.

The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Additional diseases and/or conditions include, but are not limited to, atherosclerosis, inflammatory diseases, autoimmune diseases, rheumatic heart disease. Examples of inflammatory diseases include, but are not limited to, acne vulgaris, Alzheimer's, ankylosing spondylitis, arthritis (osteoarthritis, rheumatoid arthritis (RA), psoriatic arthritis), asthma, atherosclerosis, celiac disease, chronic prostatitis, Crohn's disease, colitis, dermatitis, diverticulitis, fibromyalgia, glomerulonephritis, hepatitis, irritable bowel syndrome (IBS), systemic lupus erythematous (SLE), nephritis, Parkinson's disease, pelvic inflammatory disease, sarcoidosis, ulcerative colitis, and vasculitis.

Examples of autoimmune diseases include, but are not limited to, acute disseminated encephalomyelitis (ADEM), Addison's disease, agammaglobulinemia, alopecia areata, amyotrophic Lateral Sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenia purpura, autoimmune urticaria, autoimmune uveitis, Balo disease/Balo concentric sclerosis, Behçet's disease, Berger's disease, Bickerstaff's encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritisvepidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, giant cell arteritis, glomerulonephritis, Goodpasture's syndrome, Graves'disease, Guillain-Barré syndrome (GBS), Hashimoto's encephalopathy, Hashimoto's thyroiditis, Henoch-Schonlein purpura, herpes gestationis aka gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathyvinterstitial cystitis, juvenile idiopathic arthritis aka juvenile rheumatoid arthritis, Kawasaki's disease, Lambert-Eaton myasthenic syndrome, leukocytoclastic vasculitis, Lichen planus, Lichen sclerosus, linear IgA disease (LAD), Lou Gehrig's disease (Also Amyotrophic lateral sclerosis), lupoid hepatitis aka autoimmune hepatitis, lupus erythematosus, Majeed syndrome, Ménière's disease, microscopic polyangiitis, mixed connective tissue disease, morphea, Mucha-Habermann disease, multiple sclerosis, myasthenia gravis, myositis, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, Pars planitis, pemphigus vulgaris, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, Schmidt syndrome another form of APS, Schnitzler syndrome, scleritis, scleroderma, serum sickness, Sjögren's syndrome, spondyloarthropathy, Stiff person syndrome, subacute bacterial endocarditis (SBE), Susac's syndrome, Sweet's syndrome, sympathetic ophthalmia, Takayasu's arteritis, temporal arteritis (also known as "giant cell arteritis"), thrombocytopenia, Tolosa-Hunt syndrome, transverse myelitis, ulcerative colitis, undifferentiated connective tissue disease different from mixed connective tissue disease, undifferentiated spondyloarthropathy, urticarial vasculitis, vasculitis, vitiligo, and Wegener's granulomatosis.

The methods as provided herein may also be useful for detecting, monitoring, diagnosing and/or predicting a subject's response to an implanted device. Exemplary medical devices include but are not limited to stents, replacement heart valves, implanted cerebella stimulators, hip replacement joints, breast implants, and knee implants.

The methods as disclosed herein may be used for monitoring the health of a fetus using whole or partial genome analysis of nucleic acids derived from a fetus, as compared to the maternal genome. For example, nucleic acids can be useful in pregnant subjects for fetal diagnostics, with fetal nucleic acids serving as a marker for gender, rhesus D status, fetal aneuploidy, and sex-linked disorders. The methods as disclosed herein may identify fetal mutations or genetic abnormalities. The methods as disclosed herein can enable detection of extra or missing chromosomes, particularly those typically associated with birth defects or miscarriage. The methods as disclosed herein may comprise, or comprise the use of, the diagnosis, prediction or monitoring of autosomal trisomies (e.g., Trisomy 13, 15, 16, 18, 21, or 22) and may be based on the detection of foreign molecules. The trisomy may be associated with an increased chance of miscarriage (e.g., Trisomy 15, 16, or 22). Alternatively, the trisomy that is detected is a liveborn trisomy that may indicate that an infant will be born with birth defects (e.g., Trisomy 13 (Patau Syndrome), Trisomy 18 (Edwards Syndrome), and Trisomy 21 (Down Syndrome)). The abnormality may also be of a sex chromosome (e.g., XXY (Klinefelter's Syndrome), XYY (Jacobs Syndrome), or XXX (Trisomy X). The methods disclosed herein may comprise one or more genomic regions on the following chromosomes: 13, 18, 21, X, or Y. For example, the foreign molecule may be on chromosome 21 and/or on chromosome 18, and/or on chromosome 13. The one or more genomic regions may comprise multiple sites on multiple chromosomes.

Further fetal conditions that can be determined based on the methods herein include monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g., XXXX, XXYY, XXXY, XYYY, XXXXX, XX. XY, XXXYY, XYYYY and XXYYY), monoploidy, triploidy (three of every chromosome, e.g., 69 chromosomes in humans), tetraploidy (four of every chromosome, e.g., 92 chromosomes in humans), pentaploidy and multiploidy.

The methods as disclosed may comprise detecting, monitoring, quantitating, or evaluating one or more pathogen-derived nucleic acid molecules or one or more diseases or conditions caused by one or more pathogens. Exemplary pathogens include, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, or *Yersinia*. Additional pathogens include, but are not limited to, *Mycobacterium tuberculosis, Streptococcus, Pseudomonas, Shigella, Campylobacter*, and *Salmonella*.

The disease or conditions caused by one or more pathogens may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyogenes*; erysipelas which may be caused by a streptococcus bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis*, and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g, *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Devices

The methods disclosed herein may comprise the use of one or more devices. The methods disclosed herein may comprise the use of one or more devices to perform one or more operations or assays comprised therein. The methods disclosed herein may comprise one or more devices and the use thereof in one or more operations or assays. In particular, the methods disclosed herein may comprise one or more devices to provide individual sequence reads from individual molecules of distal nucleic acids. For example, conducting a sequencing reaction may comprise one or more sequencers. In another example, combining a plurality of data inputs and generating a combined data may comprise the use of one or more computer processors. In yet another example, one or more processors may be used in the generating and displaying electronically at least a portion of the data output. Exemplary devices include, but are not limited to, sequencers, computer processors, computer display, monitors, hard drives, thermocyclers, real-time PCR instruments, magnetic separators, transmission devices, hybridization chambers, electrophoresis apparatus, centrifuges, microscopes, imagers, fluorometers, luminometers, plate readers, computers, processors, and bioanalyzers.

The methods disclosed herein may comprise one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

The methods disclosed herein may comprise one or more thermocyclers. The one or more thermocyclers may be used to amplify one or more nucleic acid molecules. The methods disclosed herein may comprise one or more real-time PCR instruments. The one or more real-time PCR instruments may comprise a thermal cycler and a fluorimeter. The one or more thermocyclers may be used to amplify and detect one or more nucleic acid molecules.

The methods disclosed herein may comprise one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

The methods disclosed herein may comprise one or more bioanalyzers. Generally, a bioanalyzer is a chip-based capillary electrophoresis machine that can analyze RNA, DNA, and proteins. The one or more bioanalyzers may comprise Agilent's 2100 Bioanalyzer. The methods disclosed herein may comprise one or more genotyping systems, for example, a digital genotyping system.

Computer Control Systems

Figure 6:
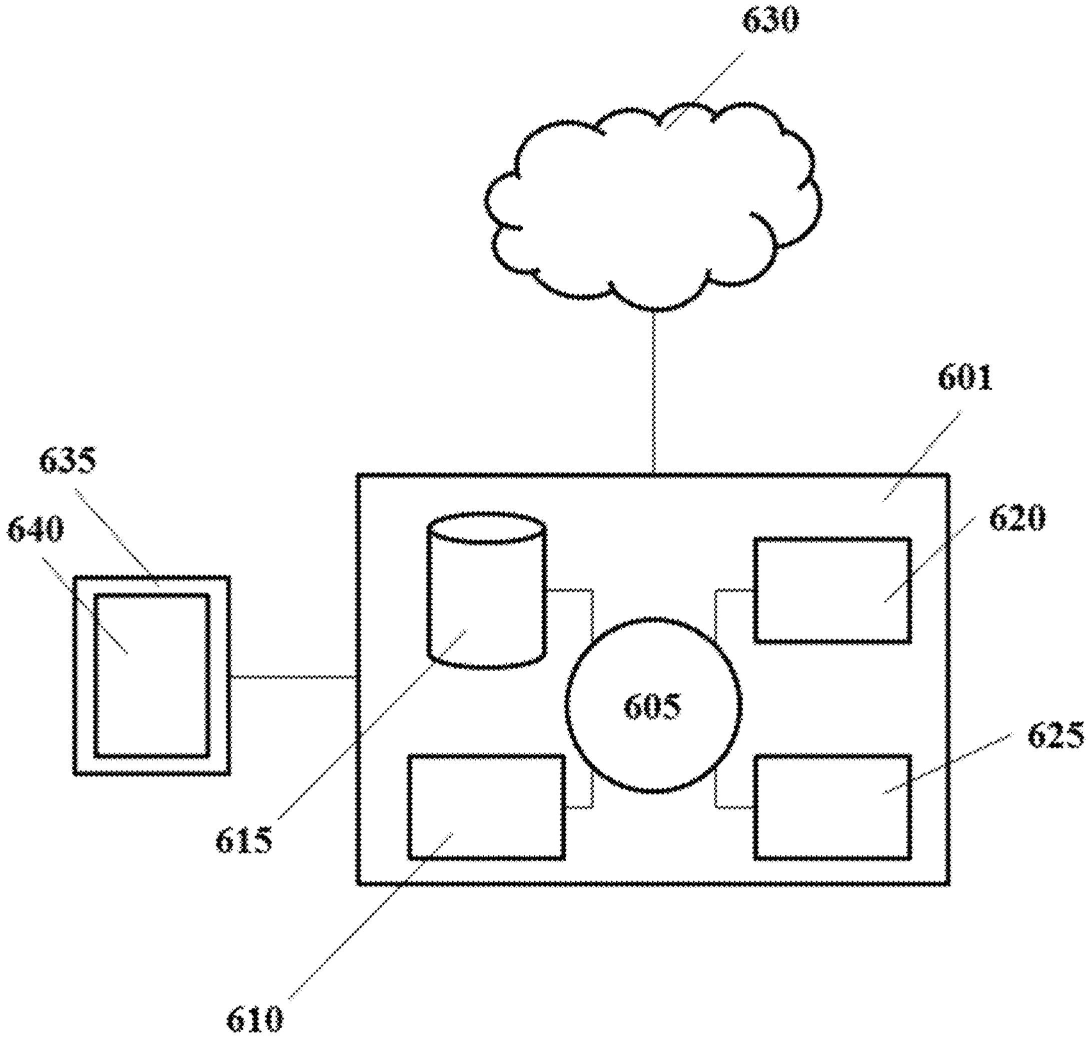
FIG. 6 shows a computer control system that is programmed or otherwise configured to implement any of the methods provided herein.

The present disclosure provides computer control systems that are programmed to implement methods of the disclosure. FIG. 6 shows a computer system 601 that is programmed or otherwise configured to implement the methods and systems disclosed herein. The computer system 601 can implement various aspects of the present disclosure, such as, for example, generating of a mutation map, sequencing a nucleic acid sequence, identifying a differential mutation and/or generating a report. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., a patient or a physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, a sequencing result, a report about health state and/or a mutation map. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, generate a mutation map.

Subjects

Often, the methods are used on a subject, in some cases human. The subject may be a male or a female. The subject may be a fetus, infant, child, adolescent, teenager or adult. The subject may be patients of any age. For example, the subject may be a patient of less than about 10 years old. For example, the subject may be a patient of at least about 0, 5, 10, 20, 30, 40, 50, 60, 70, 80, 90, or 100 years old. The subject may be in utero. Often, the subject is a patient or other individual undergoing a treatment regimen, or being evaluated for a treatment regimen (e.g., immunosuppressive therapy). However, in some instances, the subject is not undergoing a treatment regimen. For example, the subject may be a healthy subject.

In some cases, the subjects may be mammals or non-mammals. In some cases, the subjects are a mammal, such as, a human, non-human primate (e.g., apes, monkeys, chimpanzees), cat, dog, rabbit, goat, horse, cow, pig, rodent, mouse, SCID mouse, rat, guinea pig, or sheep. In some methods, species variants or homologs of these genes can be used in a non-human animal model. Species variants may be the genes in different species having greatest sequence identity and similarity in functional properties to one another. Many of such species variants human genes may be listed in the Swiss-Prot database.

The methods disclosed herein may be used on a transplant recipient who is a recipient of a solid organ or a fragment of a solid organ. The solid organ may be a lung, kidney, heart, liver, pancreas, large intestine, small intestine, gall bladder, reproductive organ or a combination thereof. In some instances, the transplant recipient may be a recipient of a tissue or cell. The tissue or cell may be amnion, skin, bone, blood, marrow, blood stem cells, platelets, umbilical cord blood, cornea, middle ear, heart valve, vein, cartilage, tendon, ligament, nerve tissue, embryonic stem(ES) cells, induced pluripotent stem cells (IPSCs), stem cells, adult stem cells, hematopoietic stem cells, or a combination thereof.

Samples

The methods disclosed herein may comprise obtaining a sample from a subject, such as a human subject. In particular, the methods may comprise obtaining a clinical specimen from a patient. For example, blood may be drawn from a patient. In some cases, the methods may comprise obtaining distal nucleic acids from multiple sources. The methods disclosed herein may comprise specifically detecting, profiling, or quantitating molecules (e.g., nucleic acids, DNA, RNA, etc.) that are within the biological samples.

One or more nucleic acids may be isolated from one or more sources. For example, DNA is isolated from one or more sources. In some cases, the sample may be distal nucleic acids obtained from intact cells being transported from their original location. By physiological processes, and disease, the nucleic acids of intact cells can end up in bodily fluids. For example, intact cells of a fetus can be detected in maternal blood. In another example, circulating tumor cells can lead to metastases in cancer.

In some cases, the sample may be distal nucleic acids obtained from dead cells. When cells die, their membranes become porous and eventually disintegrate the contents of the cell, including the nucleic acids. In some cases, cell death can be a part of normal healthy turnover of cell populations. Alternatively, the cell death can be due to disease, environmental exposure (e.g., chemicals, radiation, viruses, etc.), injury, apoptosis, necrosis or other factors. For example, apoptosis may occur locally in muscle fibers due to exercise. In other cases, apoptosis may occur in human uterine endometrium in certain portions of the menstrual cycle. These nucleic acids may be transported in the bodily fluids. For example, the sample may be distal nucleic acids transported in the form of cell-free DNA (cfDNA). In other cases, the sample may be distal nucleic acids transported in the form of cell-surface-bound DNA (csbDNA). The sample may be distal nucleic acids found in bodily fluids.

In some cases, the sample may be distal nucleic acids obtained from exosomes. Exosomes are cell-derived vesicles that can be present in many bodily fluids (e.g., blood, urine). Exosomes can be secreted from one cell then absorbed by other cells. In some cases, obtaining distal nucleic acids from exosomes may comprise isolating the exosomes from bodily fluids. Obtaining distal nucleic acids from exosomes may further comprise purifying nucleic acids from the isolated exosomes.

The sample may be a tissue sample or a bodily fluid. In some instances, the sample is a tissue sample or an organ sample, such as a biopsy. The bodily fluid may be sweat, saliva, tears, urine, blood, menses, semen, and/or spinal fluid. In some cases, the sample is a blood sample. The sample may comprise one or more peripheral blood lymphocytes. The sample may be a whole blood sample. The blood sample may be a peripheral blood sample. In some cases, the sample comprises peripheral blood mononuclear cells (PBMCs); in some cases, the sample comprises peripheral blood lymphocytes (PBLs). The sample may be a serum sample.

The sample may be obtained using any method that can provide a sample suitable for the analytical methods described herein. The sample may be obtained by a non-invasive method such as a throat swab, buccal swab, bronchial lavage, urine collection, scraping of the skin or cervix, swabbing of the cheek, saliva collection, feces collection, menses collection, or semen collection. The sample may be obtained by a minimally-invasive method such as a blood draw. The sample may be obtained by venipuncture. In other instances, the sample is obtained by an invasive procedure including but not limited to: biopsy, alveolar or pulmonary lavage, or needle aspiration. The method of biopsy may include surgical biopsy, incisional biopsy, excisional biopsy, punch biopsy, shave biopsy, or skin biopsy. The sample may be formalin fixed sections. The method of needle aspiration may further include fine needle aspiration, core needle biopsy, vacuum assisted biopsy, or large core biopsy. In some cases, multiple samples may be obtained by the methods herein to ensure a sufficient amount of biological material. In some instances, the sample is not obtained by biopsy. In some instances, the sample is not a kidney biopsy.

Nucleic Acid Samples

Methods of the present disclosure can be applied to any type of nucleic acid sample. In some cases, the nucleic acid samples can be fragmented double stranded DNA including but not limited to, for example, free DNA isolated from plasma, serum, and/or urine; DNA from apoptotic cells and/or tissues; DNA fragmented enzymatically in vitro (for example, by DNase I and/or restriction endonuclease); and/or DNA fragmented by mechanical forces (hydro-shear, sonication, nebulization, etc.). Additional suitable methods and compositions of producing nucleic acid molecules comprising stem-loop oligonucleotides are further described in detail in U.S. Pat. No. 7,803,550, which is herein incorporated by reference in its entirety.

In other cases, methods provided herein can be easily applied to any high molecular weight double stranded DNA including, for example, DNA isolated from tissues, cell culture, bodily fluids, animal tissue, plant, bacteria, fungi, viruses, etc.

Nucleic acid obtained from biological samples typically is fragmented to produce suitable fragments for analysis. Template nucleic acids may be fragmented or sheared to desired length, using a variety of mechanical, chemical and/or enzymatic methods. DNA may be randomly sheared via sonication, e.g., Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one case, nucleic acid from a biological sample is fragmented by sonication. In another case, nucleic acid is fragmented by a hydroshear instrument. Generally, individual nucleic acid template molecules can be from about 100 bases to 100 kilobases (kb), 100 bases to 90 kb, 100 bases to 80 kb, 100 bases to 70 kb, 100 bases to 60 kb, 100 bases to 50 kb, or 100 bases to about 40 kb.

Individual nucleic acid template molecules can be at least about 100 bases, 200 bases, 300 bases, 400 bases, 500 bases, 1 kb, 10 kb, 20 kb, 30 kb, 40 kb, 50 kb, 60 kb, 70 kb, 80 kb, 90 kb, 100 kb, 200 kb, 300 kb, 400 kb, or 500 kb. In some cases, nucleic acids are about 100-300, about 200-300, or about 100-500 base fragments. Nucleic acid molecules may be single-stranded, double-stranded, or double-stranded with single-stranded regions (for example, double-stranded DNA with single-stranded overhangs on one or both ends). A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In one case, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-C6H4-(OCH2-CH2)xOH, x=9-10, Triton® X-100R, Triton® X-114 x=7-8), octyl glucoside, polyoxyethylene(9)dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present disclosure, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cystamine, tricarboxyethyl phosphine (TCEP), or salts of sulfurous acid.

The methods as disclosed herein may comprise, or comprise the use of, one or more subsets of nucleic acid molecules. The subsets of nucleic acid molecules may be derived from a nucleic acid sample. The subsets of nucleic acid molecules may be derived from the same nucleic acid sample. Alternatively, or additionally, the subsets of nucleic acid molecules are derived from two or more different nucleic acid samples. Two or more subsets of nucleic acid molecules may be differentiated by their nucleic acid content. The one or more subsets of nucleic acid molecules may comprise one or more nucleic acid molecules or a variant or derivative thereof. For example, the two or more subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more subsets of nucleic acid molecules may be differentiated by GC content, nucleic acid size, genomic regions, capture probes, beads, labels, or a combination thereof.

The methods as disclosed herein may comprise, or comprise the use of, combining two or more subsets of nucleic acid molecules to produce a combined subset of nucleic acid molecules. The combined subsets of nucleic acid molecules may be derived from a nucleic acid sample. The combined subsets of nucleic acid molecules may be derived from the same nucleic acid sample. Alternatively, or additionally, the combined subsets of nucleic acid molecules are derived from two or more different nucleic acid samples. Two or more combined subsets of nucleic acid molecules may be differentiated by their nucleic acid content. The one or more combined subsets of nucleic acid molecules may comprise one or more nucleic acid molecules or a variant or derivative thereof. For example, the two or more combined subsets of nucleic acid molecules may comprise nucleic acids comprising different GC content, nucleic acid size, genomic regions, genomic region features, eluted nucleic acid molecules, hybridized nucleic acid molecules, non-hybridized nucleic acid molecules, amplified nucleic acid molecules, non-amplified nucleic acid molecules, supernatant-derived nucleic acid molecules, eluant-derived nucleic acid molecules, labeled nucleic acid molecules, non-labeled nucleic acid molecules, capture probe hybridized nucleic acid molecules, capture probe free nucleic acid molecules, bead bound nucleic acid molecules, bead free nucleic acid molecules, or a combination thereof. The two or more combined subsets of nucleic acid molecules may be differentiated by GC content, nucleic acid size, genomic regions, capture probes, beads, labels, or a combination thereof.

Subsets of nucleic acid molecules may comprise one or more genomic regions as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic regions. The one or more genomic regions may be identical, similar, different, or a combination thereof.

Subsets of nucleic acid molecules may comprise one or more genomic region features as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomic region features. The one or more genomic region features may be identical, similar, different, or a combination thereof.

Subsets of nucleic acid molecules may comprise nucleic acid molecules of different sizes. The length of a nucleic acid molecule in a subset of nucleic acid molecules may be referred to as the size of the nucleic acid molecule. The average length of the nucleic acid molecules in a subset of nucleic acid molecules may be referred to as the mean size of nucleic acid molecules. As used herein, the terms "size of a nucleic acid molecule", "mean size of nucleic acid molecules", "molecular size" and "mean molecular size" may be used interchangeably. The size of a nucleic acid molecule may be used to differentiate two or more subsets of nucleic acid molecules. The difference in the mean size of nucleic acid molecules in a subset of nucleic acid molecules and the mean size of nucleic acid molecules in another subset of nucleic acid molecules may be used to differentiate the two subsets of nucleic acid molecules. The mean size of nucleic acid molecules in one subset of nucleic acid molecules may be greater than the mean size of nucleic acid molecules in at least one other subset of nucleic acid molecules. The mean size of nucleic acid molecules in one subset of nucleic acid molecules may be less than the mean size of nucleic acid molecules in at least one other subset of nucleic acid molecules. The difference in mean molecular size between two or more subsets of nucleic acid molecules may be at least about 50; 75; 100; 125; 150; 175; 200; 225; 250; 275;

300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular size between two or more subsets of nucleic acid molecules is at least about 200 bases or bases pairs. Alternatively, the difference in mean molecular size between two or more subsets of nucleic acid molecules is at least about 300 bases or bases pairs.

Subsets of nucleic acid molecules may comprise nucleic acid molecules of different sequencing sizes. The length of a nucleic acid molecule in a subset of nucleic acid molecules to be sequenced may be referred to as the sequencing size of the nucleic acid molecule. The average length of the nucleic acid molecules in a subset of nucleic acid molecules may be referred to as the mean sequencing size of nucleic acid molecules. As used herein, the terms "sequencing size of a nucleic acid molecule", "mean sequencing size of nucleic acid molecules", "molecular sequencing size" and "mean molecular sequencing size" may be used interchangeably. The mean molecular sequencing size of one or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. The sequencing size of a nucleic acid molecule may be used to differentiate two or more subsets of nucleic acid molecules. The difference in the mean sequencing size of nucleic acid molecules in a subset of nucleic acid molecules and the mean sequencing size of nucleic acid molecules in another subset of nucleic acid molecules may be used to differentiate the two subsets of nucleic acid molecules. The mean sequencing size of nucleic acid molecules in one subset of nucleic acid molecules may be greater than the mean sequencing size of nucleic acid molecules in at least one other subset of nucleic acid molecules. The mean sequencing size of nucleic acid molecules in one subset of nucleic acid molecules may be less than the mean sequencing size of nucleic acid molecules in at least one other subset of nucleic acid molecules. The difference in mean molecular sequencing size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular sequencing size between two or more subsets of nucleic acid molecules is at least about 200 bases or bases pairs. Alternatively, the difference in mean molecular sequencing size between two or more subsets of nucleic acid molecules is at least about 300 bases or bases pairs.

Two or more subsets of nucleic acid molecules may be at least partially complementary. For example, a first subset of nucleic acid molecules may comprise nucleic acid molecules comprising at least a first portion of the genome and a second subset of nucleic acid molecules may comprise nucleic acid molecules comprising at least a second portion of the genome, wherein the first and second portion of the genome differ by one or more nucleic acid molecules. Thus, the first subset and the second subset are at least partially complementary. The complementarity of two or more subsets of nucleic acid molecules may be at least about 10%, 15%, 20%, 25%, 30%, 35%, 40%, 45%, 50%, 55%, 60%, 65%, 70%, 75%, 80%, 85%, 90%, 95%, 97%, or more. As used herein, the term "complementarity of two or more subsets of nucleic acid molecules" generally refers to genomic content of the two or more subsets and the extent to which the two or more subsets encompass the content of one or more genomic regions. For example, a first subset of nucleic acid molecules comprises 50% of total high GC exomes and a second subset of nucleic acid molecules comprises 50% of the total low GC exomes, then the complementarity of the two subsets of nucleic acid molecules in reference to an entire exome is 50%. In another example, a first subset of nucleic acid molecules comprises 100% of the total bead bound nucleic acid molecules and the second subset of nucleic acid molecules comprises 100% of the total bead free nucleic acid molecules, the complementarity of the two subsets in reference to the total nucleic acid molecules is 100%.

Subsets of nucleic acid molecules may comprise bead bound nucleic acid molecules. Two or more subsets of nucleic acid molecules may be differentiated into bead bound nucleic acid molecules and bead free nucleic acid molecules. For example, a first subset of nucleic acid molecules may comprise one or more bead bound nucleic acid molecules and a second subset of nucleic acid molecules may comprise bead free nucleic acid molecules. Bead free nucleic acid molecules may refer to nucleic acid molecules that are not bound to one or more beads. Bead free nucleic acid molecules may refer to nucleic acid molecules that have been eluted from one or more beads. For example, the nucleic acid molecule from a bead bound nucleic acid molecule may be eluted to produce a bead free nucleic acid molecule.

Subsets of nucleic acid molecules may comprise capture probe hybridized nucleic acid molecules. Two or more subsets of nucleic acid molecules may be differentiated into capture probe hybridized nucleic acid molecules and capture probe free nucleic acid molecules. For example, a first subset of nucleic acid molecules may comprise one or more capture probe hybridized nucleic acid molecules and a second subset of nucleic acid molecules may comprise capture probe free nucleic acid molecules. Capture probe free nucleic acid molecules may refer to nucleic acid molecules that are not hybridized to one or more capture probes. Capture probe free nucleic acid molecules may refer to nucleic acid molecules that are dehybridized from one or more capture probes. For example, the capture probe from a capture probe hybridized nucleic acid molecule may be removed to produce a capture probe free nucleic acid molecule.

Capture probes may hybridize to one or more nucleic acid molecules in a sample or in a subset of nucleic acid molecules. Capture probes may hybridize to one or more genomic regions. Capture probes may hybridize to one or more genomic regions within, around, near, or spanning one or more genes, exons, introns, UTRs, or a combination thereof. Capture probes may hybridize to one or more genomic regions spanning one or more genes, exons, introns, UTRs, or a combination thereof. Capture probes may hybridize to one or more known inDels. Capture probes may hybridize to one or more known structural variants.

Subsets of nucleic acid molecules may comprise labeled nucleic acid molecules. Two or more subsets of nucleic acid molecules may be differentiated into labeled nucleic acid molecules and non-labeled nucleic acid molecules. For example, a first subset of nucleic acid molecules may comprise one or more labeled nucleic acid molecules and a second subset of nucleic acid molecules may comprise non-labeled nucleic acid molecules. Non-labeled nucleic acid molecules may refer to nucleic acid molecules that are not attached to one or more labels. Non-labeled nucleic acid molecules may refer to nucleic acid molecules that have been detached from one or more labels. For example, the label from a labeled nucleic acid molecule may be removed to produce a non-labeled nucleic acid molecule.

The methods as disclosed herein may comprise, or comprise the use of, one or more labels. The one or more labels may be attached to one or more capture probes, nucleic acid molecules, beads, primers, or a combination thereof. Examples of labels include, but are not limited to, detectable labels, such as radioisotopes, fluorophores, chemiluminophores, chromophore, lumiphore, enzymes, colloidal particles, and fluorescent microparticles, quantum dots, as well as antigens, antibodies, haptens, avidin/streptavidin, biotin, haptens, enzymes cofactors/substrates, one or more members of a quenching system, a chromogens, haptens, a magnetic particles, materials exhibiting nonlinear optics, semiconductor nanocrystals, metal nanoparticles, enzymes, aptamers, and one or more members of a binding pair.

The one or more subsets of nucleic acid molecules may be subjected to one or more assays. The one or more subsets of nucleic acid molecules may be subjected to one or more assays based on their biochemical features. The one or more subsets of nucleic acid molecules may be subjected to one or more assays based on their genomic region features. The one or more subsets of nucleic acid molecules may be subjected to 1, 2, 3, 4, 5, 6, 7, 8, 9, 10 or more assays. The one or more subsets of nucleic acid molecules may be subjected to 1, 2, 3, 4, 5, 6, 7, 8, 9, 10 or more assays based on their biochemical features. The one or more subsets of nucleic acid molecules may be subjected to 1, 2, 3, 4, 5, 6, 7, 8, 9, 10 or more assays based on their genomic region features. The one or more subsets of nucleic acid molecules may be subjected to 1, 2, 3, 4, 5, 6, 7, 8, 9, 10 or more identical assays. The one or more subsets of nucleic acid molecules may be subjected to 1, 2, 3, 4, 5, 6, 7, 8, 9, 10 or more identical assays based on their biochemical features. The one or more subsets of nucleic acid molecules may be subjected to 1, 2, 3, 4, 5, 6, 7, 8, 9, 10 or more identical assays based on their genomic region features. The one or more subsets of nucleic acid molecules may be subjected to 1, 2, 3, 4, 5, 6, 7, 8, 9, 10 or more similar assays. The one or more subsets of nucleic acid molecules may be subjected to 1, 2, 3, 4, 5, 6, 7, 8, 9, 10 or more similar assays based on their biochemical features. The one or more subsets of nucleic acid molecules may be subjected to 1, 2, 3, 4, 5, 6, 7, 8, 9, 10 or more similar assays based on their genomic region features. The one or more subsets of nucleic acid molecules may be subjected to 1, 2, 3, 4, 5, 6, 7, 8, 9, 10 or more different assays. The one or more subsets of nucleic acid molecules may be subjected to 1, 2, 3, 4, 5, 6, 7, 8, 9, 10 or more different assays based on their biochemical features. The one or more subsets of nucleic acid molecules may be subjected to 1, 2, 3, 4, 5, 6, 7, 8, 9, 10 or more different assays based on their genomic region features. The two or more subsets of nucleic acid molecules may be subjected to one or more identical processing operations based on their biochemical features. The two or more subsets of nucleic acid molecules may be subjected to one or more identical processing operations based on their genomic region features. The two or more subsets of nucleic acid molecules may be subjected to one or more similar processing operations based on their biochemical features. The two or more subsets of nucleic acid molecules may be subjected to one or more similar processing operations based on their genomic region features. The two or more subsets of nucleic acid molecules may be subjected to one or more different processing operations based on their biochemical features. The two or more subsets of nucleic acid molecules may be subjected to one or more different processing operations based on their genomic region features.

The methods as disclosed herein may comprise, or comprise the use of, producing two or more subsets of nucleic acid molecules. The two or more subsets of nucleic acid molecules may be separated fluidically, separated into two or more containers, separated into two or more locations, or a combination thereof. For example, a first subset of nucleic acid molecules and a second subset of nucleic acid molecules are fluidically separated. In another example, a first subset of nucleic acid molecules is in a first container and a second subset of nucleic acid molecules is in a second container. In yet another example, a first subset of nucleic acid molecules and a second subset of nucleic acid molecules are assigned to two or more locations on a first container, and a third subset of nucleic acid molecules is in a second container.

As used herein and in the appended claims, the singular forms “a”, “an”, and “the” include plural referents unless the context clearly dictates otherwise. Thus, for example, reference to “a cell” can include one or a plurality of such cells, and reference to “the peptide” can include reference to one or more peptides and equivalents thereof, e.g., polypeptides, and so forth.

Where a range of values is provided, it is understood that each intervening value between the upper and lower limits of that range, to the tenth of the unit of the lower limit, unless the context clearly dictates otherwise, is also specifically disclosed. Each smaller range between any stated value or intervening value in a stated range, and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

EXAMPLES

The following examples are given for the purpose of illustrating various embodiments of the present disclosure and are not meant to limit the present disclosure. The present examples, along with the methods described herein, are exemplary and are not intended as limitations on the scope of the present disclosure.

Example 1. Generation of a Developmental Mutation Map

The following illustrates an example of generating a developmental mutation map utilizing the methods disclosed herein. A developmental tree, for example of the kind depicted in FIG. 1, is used to map differential mutations to various tissues. The developmental tree depicts a developmental relationship between the tissues of an organism. To generate the developmental mutation map, various tissue samples are obtained from an individual. These samples are obtained from all over the individual's body and can include samples from blood, a skin biopsy, a hair sample, and the like. Nucleic acids are extracted from the samples and are sequenced by whole genome sequencing (WGS) to identify differential mutations between the various tissue samples. At some time in the future, the individual undergoes a procedure (e.g., a colonoscopy). A biopsy of the tissue (e.g., a biopsy of the colon) is taken during the procedure, nucleic acids are extracted from the biopsy, and the nucleic acids are sequenced to identify additional differential mutations. The differential mutations are mapped onto the developmental tree by associating the tissue source on the tree to the differential mutation. For example, a mutation is identified in the sample obtained from the pancreas, but not in lungs. This suggests that the mutation occurred sometime during branching of the primitive gut to the lungs and the digestive tube. All of the identified mutations are mapped in this fashion generating a comprehensive developmental mutation map.

Example 2. Diagnosis of Pancreatic Cancer in a Patient by Sampling Nucleic Acids Distal to their Origin The following illustrates an example of identifying the origin of a distal nucleic acid utilizing the methods disclosed herein. A blood sample is obtained from a patient during a routine visit to the clinic. Cell-free DNA (cfDNA) is extracted from the blood sample and is sequenced. Sequence reads are aligned to a reference sequence and mosaic variants are identified. A mutation is identified that is represented more frequently in the cfDNA than may be expected under ordinary conditions. The mutation is mapped to a developmental mutation map that was previously generated for the patient using the methods of Example 1. The mutation is identified as a mutation that was previously determined to be associated with the pancreas. This mutation, as depicted on the developmental mutation map, is previously identified in the pancreas and the stomach, but not in the intestine or the bile duct, suggesting the mutation occurred after division of the primitive gut to the foregut, the midgut and the hindgut. This information suggests that a tissue of the foregut may be under stress. A biopsy of the pancreas and the stomach are taken. The sample from the stomach is negative but the sample from the pancreas indicates the presence of a small tumor. The patient is diagnosed with pancreatic cancer far earlier than may otherwise be detected.

Example 3. Identification of the Tissue of Origin of a Tumor Metastasis

The following illustrates an example of identifying the tissue of origin of a tumor metastasis. A metastatic tumor is distal to its origin. In some cancer cases, a primary tumor may no longer exist (e.g., if it has been destroyed by the immune system), but metastases may still exist in other places in the body. Because the cells of such a metastasis are derived from the primary tumor, which was itself derived from a cell of the tissue of origin, the metastatic cells may still carry the mosaic variants of the original tissue. This may be important because the treatment for a metastatic tumor can depend on the tissue of origin. In this example, a biopsy of a metastatic tumor is taken from a subject. The nucleic acid molecules are extracted from the tumor, sequenced and mosaic variants are identified. The mosaic variants are mapped to a developmental mutation map of the subject. In this example, a variant is identified in the metastatic tumor that maps to the pancreas on the mutation map. It is determined that the origin of the tumor is the pancreas. The subject is treated with an anti-cancer agent that is commonly used to treat pancreatic cancer (e.g., gemcitabine).

Example 4. Detecting Variants in Leukemia by Tumor Versus Normal Analysis

In this example, a tumor versus normal analysis using the methods described herein is illustrated. In this example, the tumor is a leukemia and may be detected from a nucleic acid sample taken from a leukocyte. A blood sample is taken from a patient during a routine visit to the clinic. The blood sample is centrifuged to separate the blood into plasma, buffy coat, and red blood cells. The plasma contains cfDNA and the buffy coat contains leukocytes (i.e., some of which may be leukemia cells). Nucleic acids are extracted from both the plasma and the leukocytes, the nucleic acids are sequenced, and variants are detected in the samples. In this example, the sequence identified in the cfDNA is the "normal" sample and the leukocytes are the "tumor" sample. The sequences are compared and variants that occur only in the leukemia are identified.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting a presence or recurrence of a solid tumor in a human subject, comprising:

(a) generating a first set of sequence reads and a second set of sequence reads by independently performing whole genome sequencing on:

(i) nucleic acid molecules extracted from a cell-free portion of a first blood sample of a human subject, wherein the nucleic acid molecules extracted from the cell-free portion of the first blood sample are derived from a tissue of origin, wherein the tissue of origin comprises a benign tissue, a malignant tissue, or a mixed tissue, and (ii) nucleic acid molecules extracted from leukocytes from the first blood sample, wherein the leukocytes are a normal sample;

(b) comparing with a programmed computer processor the first set of sequence reads and the second set of sequence reads to identify mosaic variants, wherein the mosaic variants are present in the first set of sequence reads and are not present in the second set of sequence reads;

(c) obtaining one or more blood samples from the human subject at a time point that is subsequent to when the first blood sample was obtained;

(d) extracting non-amplified nucleic acid molecules from the one or more blood samples obtained in step (c);

(e) enriching nucleic acid molecules extracted from the one or more blood samples obtained in step (c) using a plurality of biotin-labeled capture probes in solution, wherein individual instances of the plurality of biotin-labeled capture probes are configured to hybridize to individual instances of the mosaic variants identified in step (b);

(f) performing a sequencing assay on the nucleic acid molecules enriched in step (e) to identify the presence or absence of individual instances of the mosaic variants identified in step (b) one or more times over the life of the human subject; and (g) providing a report based on the presence or absence of the individual instances of mosaic variants in the one or more blood samples, thereby detecting the presence or recurrence of the solid tumor in the human subject.

2. The method of claim 1, further comprising, subsequent to the extracting of step (d) but prior to the enriching of step (e), amplifying the non-amplified nucleic acid molecules from the one or more blood samples from the human subject.

3. The method of claim 1, wherein the mosaic variants are selected from the group consisting of: (i) copy number variation, (ii) small insertions and deletions (inDels), (iii) single nucleotide polymorphisms (SNPs), (iv) multiple nucleotide polymorphisms (MNPs), and (v) any combination thereof.

4. The method of claim 1, wherein the mosaic variants identified comprise somatic mosaicism.

5. The method of claim 1, wherein the mosaic variants are causal or predisposing for a solid tumor.

6. The method of claim 1, wherein the mosaic variants are non-causal for a solid tumor.

7. The method of claim 1, wherein the sequencing assay of step (f) comprises next generation sequencing, duplex sequencing, or redundant sequencing.

8. The method of claim 1, wherein the one or more blood samples are separated into at least a first component that includes cell-free or surface-bound nucleic acid molecules and a second component that includes leukocytes.

9. The method of claim 8, wherein the sequencing assay of step (f) is performed on the first component that includes cell-free or surface-bound nucleic acid molecules.

10. The method of claim 9, wherein the cell-free nucleic acid molecules comprise cell-free DNA.

11. The method of claim 1, wherein the report further comprises predicting, diagnosing, and/or prognosing a status or outcome of the solid tumor in the human subject.

12. The method of claim 11, wherein the predicting, diagnosing, and/or prognosing the status or outcome of the solid tumor comprises: (i) diagnosing the solid tumor, (ii) identifying the solid tumor, (iii) determining the stage of the solid tumor, (iv) assessing the risk of the solid tumor, (v) assessing the risk of recurrence of the solid tumor, (vi) assessing the efficacy of a drug, (vii) assessing risk of an adverse drug reaction, (viii) predicting optimal drug dosage, (ix) predicting drug resistance, or (x) a combination thereof.

13. The method of claim 12, wherein the solid tumor comprises a sarcoma, a carcinoma, or a lymphoma.

14. The method of claim 1, wherein the report further comprises a determination of state of health of the tissue of origin.

15. The method of claim 14, wherein the state of health of the tissue of origin is determined by comparing a quantity of nucleic acid molecules from the tissue of origin against a reference to identify a relative abundance of the nucleic acid molecules from the tissue of origin.

16. The method of claim 14, wherein the state of health of the tissue of origin is determined by aligning one or more nucleic acid sequences or portions thereof from the tissue of origin to a genome or exome of the human subject to identify a location of the one or more nucleic acid sequences or portions thereof from the tissue of origin, which location is indicative of the state of health.

17. The method of claim 14, wherein the state of health of the tissue of origin is determined by comparing one or more nucleic acid sequences or portions thereof from the tissue of origin to a reference to determine an apoptotic pattern, necrotic pattern, or predetermined mutations.

18. The method of claim 14, wherein the state of health of the tissue of origin is classified as unhealthy or potentially unhealthy.

19. The method of claim 1, further comprising:

(h) obtaining an additional blood or plasma sample from the human subject at a time point later than the one or more blood samples;

(i) repeating steps (d)-(f) using nucleic acid molecules isolated from the additional blood or plasma sample; and (j) providing an additional report based on the presence or absence of the mosaic variants in the additional blood or plasma sample, thereby detecting the presence or recurrence of the solid tumor in the human subject.

20. The method of claim 1, wherein individual instances of the plurality of biotin-labeled capture probes each comprise different nucleic acid binding sites.

21. The method of claim 1, wherein individual instances of the plurality of biotin-labeled capture probes each comprise between about 10 to about 500 nucleotides.

22. The method of claim 1, wherein the enriching of step (e) comprises:

(i) hybridizing the non-amplified nucleic acid molecules from the one or more blood samples to the plurality of biotin-labeled capture probes in solution;

(ii) separating capture probe-hybridized non-amplified nucleic acid molecules from capture-probe free non-amplified nucleic acid molecules.

23. The method of claim 22, wherein the enriching of step (e) further comprises:

(iii) conducting one or more elution reactions on the capture probe-hybridized non-amplified nucleic acid molecules.

24. The method of claim 22, wherein, prior to the separating of step (e)(ii), the nucleic acid molecules extracted from the one or more blood samples are further hybridized to a plurality of beads, and the method further comprises fragmenting bead bound nucleic acid molecules, wherein the ratio of the volume of the beads to the volume of the nucleic acid sample is about 0.10 or more.

25. The method of claim 22, wherein, prior to the separating of step (e)(ii), the nucleic acid molecules extracted from the one or more blood samples are further hybridized to a plurality of beads, and the method further comprises fragmenting bead bound nucleic acid molecules, wherein the ratio of the volume of the beads to the volume of the nucleic acid sample is about 2.00 or less.

26. The method of claim 1, wherein at least a subset of the mosaic variants identified in step (f) are below an allele frequency in the one or more blood samples of less than about 0.1%.

27. The method of claim 1, wherein at least a subset of the non-amplified nucleic acid molecules extracted from the one or more blood samples are present at a concentration of about less than 1%.

28. The method of claim 1, wherein the mosaic variants identified in step (f) are detected with a specificity greater than about 90%.

29. The method of claim 1, wherein the mosaic variants identified in step (f) are detected with a sensitivity greater than about 90%.

30. The method of claim 1, wherein percent error rate of the sequencing assay of step (f) is less than about 0.001%.

* * * * *